(12) United States Patent
Frosch et al.

(10) Patent No.: US 12,412,652 B2
(45) Date of Patent: Sep. 9, 2025

(54) FEDERATED, CENTRALIZED, AND COLLABORATIVE MEDICAL DATA MANAGEMENT AND ORCHESTRATION PLATFORM TO FACILITATE HEALTHCARE IMAGE PROCESSING AND ANALYSIS

(71) Applicant: GE Precision Healthcare LLC, Waukesha, WI (US)

(72) Inventors: Travis R. Frosch, Orlando, FL (US); Sylvain Adam, Brookfield, WI (US); Garry M. Whitley, Clinton, TN (US); Heather McCombs Chait, Chicago, IL (US); Steve M. Lawson, Milwaukee, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/441,532

(22) Filed: Feb. 14, 2024

(65) Prior Publication Data
US 2024/0185989 A1 Jun. 6, 2024

Related U.S. Application Data

(63) Continuation of application No. 17/102,620, filed on Nov. 24, 2020, now Pat. No. 11,935,643.

(Continued)

(51) Int. Cl.
*G06K 9/00* (2022.01)
*G06T 7/00* (2017.01)
(Continued)

(52) U.S. Cl.
CPC ........... *G16H 30/20* (2018.01); *G06T 7/0012* (2013.01); *G16H 10/60* (2018.01); *G16H 30/40* (2018.01);

(Continued)

(58) Field of Classification Search
None
See application file for complete search history.

(56) References Cited

U.S. PATENT DOCUMENTS

| 10,127,621 B2 | 11/2018 | Cialdea et al. |
| 2009/0313368 A1 | 12/2009 | Hollebeek et al. |

(Continued)

FOREIGN PATENT DOCUMENTS

| CA | 2 637 574 C | 10/2017 |
| WO | 2011/159849 A1 | 12/2011 |

OTHER PUBLICATIONS

Non-Final Office Action received for U.S. Appl. No. 17/102,620, dated Jul. 19, 2023, 118 pages.
(Continued)

*Primary Examiner* — Wei Wen Yang

(57) ABSTRACT

A computer-implemented system is provided that includes a plurality of endpoint databases employed to store medical images and metadata that describes attributes of the respective medical images. A management and orchestration platform periodically scans the endpoint databases to determine an index of the recently acquired medical images and associated metadata and updates to metadata associated with previously stored medical images. A search engine executes the search function to retrieve at least one of the recently acquired medical images and associated metadata and the recent updates to metadata associated with the previously stored medical images. The platform can also provide project management services and various collaborative, social networking type services. For example, the platform can facilitate collaborative review of medical image data, allowing users to rate and review the medical image data, annotate the medical image data, edit and augment the medical image data, and the like.

20 Claims, 50 Drawing Sheets

Related U.S. Application Data

(60) Provisional application No. 62/941,193, filed on Nov. 27, 2019.

(51) Int. Cl.
　　　*G16H 10/60*　　　(2018.01)
　　　*G16H 30/20*　　　(2018.01)
　　　*G16H 30/40*　　　(2018.01)
　　　*G16H 40/67*　　　(2018.01)
　　　*G16H 70/00*　　　(2018.01)

(52) U.S. Cl.
　　　CPC ............. *G16H 40/67* (2018.01); *G16H 70/00* (2018.01); *G06T 2207/20084* (2013.01); *G06T 2207/30004* (2013.01)

(56) References Cited

U.S. PATENT DOCUMENTS

| | | |
|---|---|---|
| 2011/0246239 A1 | 10/2011 | Vdovjak et al. |
| 2012/0131011 A1 | 5/2012 | Vdovjak et al. |
| 2014/0142984 A1 | 5/2014 | Wright et al. |
| 2016/0147971 A1 | 5/2016 | Kolowitz et al. |
| 2016/0154844 A1* | 6/2016 | Park .................... G06F 16/51 707/722 |
| 2021/0090694 A1 | 3/2021 | Colley et al. |

OTHER PUBLICATIONS

Notice of Allowance received for U.S. Appl. No. 17/102,620, dated Nov. 15, 2023, 37 pages.

\* cited by examiner

FIG. 8B

New search - In Exam

808

- Tag Name
- Modality
- Patient Name
- Patient ID
- Exam ID
- Exam Description
- Exam Date dd/mm/yyyy
- Accession
- Institution
- Only Exams with Clinical Stories

- Host Name
- Scanner name
- Manufacturer
- Uploaded by
- Operator name
- Data usage agreement
- Rating average
- Patient BMI
- Patient weight
- Patient age

810 Filter Anatomy Parts

Search Parts

- Head
- Neck
- UpperExtremities
- Chest
- Abdomen
- Spine
- Pelvis
- LowerExtremities
- Whole Body Parts Reset | Display Results

New search - In Series

Series Description

Tag Name · Average Rating · Software Version

○ CT  ● MR  PET  X-Ray — 812

Series MR Acquisition Parameters

814 Pulse Sequence Name
Coil Name
Imaging Options
· Field Strength
Multidrive
Distortion Correction

816 Slice Thickness
Pixel Size ·x·
Matrix ·x·
Recon Matrix ·Rows·x·Col
FOV ·

818 TE ·x·
TR ·x·
TI ·x·
ETL ·Min·Max
Acquisition Duration ·

820 Technique
Any
Acceleration ·Phase·Slice
HyberBand
HyberSeries

Reset   Display Results

— 831

★ 4.9 (347)   ☆ Awaiting your review

Exam ID – Hand Example
Scanner Name

| ID | Exam ID No. |
| | Exam date |
| | Exam location |
| | Scope |
| | Uploaded by |
| ACC | Accession No. |

Open Examination

| Number of Images | Series ID | Number of Ratings | |
|---|---|---|---|
| 3 | XXZ1 | 13 | ☆ |
| 4 | XXZ2 | 29 | ☆ |
| 5 | XXZ3 | 29 | ☆ |
| 6 | XXZ4 | 944 | ☆ |
| 7 | XXZ5 | 18 | ☆ |
| 800 | XXZ1 | 944 | ☆ |
| 801 | XXZ2 | 944 | ☆ |
| 802 | XXZ3 | 944 | ☆ |
| 803 | XXZ4 | 944 | ☆ |
| 804 | XXZ5 | 944 | ☆ |
| 805 | XXZ2 | 944 | ☆ |
| 806 | XXZ4 | 944 | ☆ |

Exam ID – Hand Example    ★ 4.9 (347)    ☆ Awaiting your review

Series    Exam Feed    Clinical Story

| Series ID | | Description | Type | Coil | Acquisition duration | Number of Images | Modality | Rating | Date | Time |
|---|---|---|---|---|---|---|---|---|---|---|
| 1 | | sagxx | Other | Sm | 02:08 | 12 | MR | ✦ | 11/2/21 | 10:08 AM |
| 4 | | AxT2 | Other | Sm | 04:33 | 29 | MR | ✦ | 10/4/18 | 4:33 PM |
| 5 | | ATtX | Other | Sm | 02:21 | 29 | MR | ✦ | 11/9/20 | 2:21 PM |
| 6 | | Example | Other | Sm | 02:39 | 944 | MR | ✦ | 4/7/17 | 12:39 PM |
| 7 | | Sag1 | Other | Sm | 02:22 | 18 | MR | ✦ | 6/7/19 | 3:22 PM |
| 600 | | sagxx | Other | Sm | 04:11 | 944 | MR | ✦ | 12/12/21 | 11:11 AM |
| 601 | | AxT2 | Other | Sm | 02:08 | 29 | MR | ✦ | 8/5/19 | 10:30 AM |
| 602 | | ATtX | Other | Sm | 04:33 | 77 | MR | ✦ | 9/18/22 | 11:33 AM |
| 603 | | sagxR | Other | Sm | 02:21 | 19 | MR | ✦ | 1/2/21 | 5:21 AM |

Series Image ID   ★ 4.9 (347)   ☆ Awaiting your review

Jpeg Preview   DICOM Preview   Mosaic View

Image Parameters

ET xxxx    TE xx     ACQ xx/xxx
PS xxxxx   FOV xx    MA xxxx
TR xx      ST xx/xxx NEX xxx
TE xx

Summary   Activity   Reviews   DICOM Tags   ● Detailed Info

Series Details

Protocol Name:       xxxxxxxxxxxx
Modality:            xxxxxx
Model Name:          xxxxxxxxxxx
Acquisition Type:    xxxx
Software Version:    xxxxxxxxxxxxxxxxx

MR Data

PSD Information:     xxxxxxxxxxxxxxxxx
Precision Values:    xxxxxx
Field Strength:      xxxxxxxxxxx
No Phase Wrap:       xxxx

Series Location

▨ Endpoint Workstation File xxxx1

▨ Endpoint Workstation File xxxx2

▨ Endpoint Database xxxx1

1200

Exam ID – Hand Example

★ 4.9 (347)  ☆ Awaiting your review

Series    Exam Feed    Clinical Story

★★★★★  3 Reviews

November 7, 2019

Adam S. added a tag

DICOM Tag xy

Adam S. added a tag

DICOM Tag xp

August 22, 2018

Mario L. posted a review

★★★★★

February 14, 2017

Lee C. posted a review

| | | | | | |
|---|---|---|---|---|---|
| Workstations | Projects | User Permissions | | | Create new request |
| Images Request | EMR Request | User Requests | | | |
| Up to 10k echo scans; divided among each region | 2D | Yes | 4 | 10k | Protocol single image per screen; B mode · 150 Exams · 5 Exams · 10236 Scans · 30 Scans |
| Up to 10k echo scans; divided among each region | 3D | No | 4 | 10k | Protocol single image per screen; C mode · 120 Exams · 4 Exams · 9236 Scans · 18 Scans |

Workstations | Projects | User Permissions | Requests

Images Request | EMR Request | User Requests

[PHI Request] [Edit Request] [Compare Request] [Find Similar Images Request] [Image Processing Request] [Feedback Request] [Create Request]

Your Content Requests

8 Requests — Display: All Requests

1. Headache... images contain patient data, cell, MS, 65 — 45 min ago
2. Pain... images contain patient data, cell, MS, 65 — 49 min ago
3. Symptom... images contain patient data, Cell Cubes Head 07 — 2 hours ago
4. Patient... images contain patient data, cell, MS, 65 — 7 hours ago 10. One or more series contain patient data

FIG. 14D

LOCAL DEVICE DEPLOYMENT

FEDERATED, CENTRALIZED, AND COLLABORATIVE MEDICAL DATA MANAGEMENT AND ORCHESTRATION PLATFORM TO FACILITATE HEALTHCARE IMAGE PROCESSING AND ANALYSIS

CROSS-REFERENCE TO RELATED APPLICATIONS

This application is a continuation of and claims priority to each of U.S. application Ser. No. 17/102,620 filed Nov. 24, 2020 and titled "FEDERATED, CENTRALIZED, AND COLLABORATIVE MEDICAL DATA MANAGEMENT AND ORCHESTRATION PLATFORM TO FACILITATE HEALTHCARE IMAGE PROCESSING AND ANALYSIS," which claims priority to U.S. Provisional Application Ser. No. 62/941,193 filed Nov. 27, 2019 and titled "FEDERATED, CENTRALIZED, AND COLLABORATIVE MEDICAL DATA MANAGEMENT AND ORCHESTRATION PLATFORM TO FACILITATE HEALTHCARE IMAGE PROCESSING AND ANALYSIS," the entireties of which applications are incorporated herein by reference.

TECHNICAL FIELD

This application relates to a web-based medical image data platform that provides various services related to accessing, managing, and sharing anonymized medical image data to facilitate healthcare image processing and analysis.

BACKGROUND

The healthcare industry has innumerable opportunities to leverage artificial intelligence (AI), machine learning (ML), and other analytical models to achieve more accurate, proactive, and comprehensive patient care. From reducing administrative burdens to supporting precision medicine, these analytical tools are showing promise across clinical, financial, and operational domains. Learning algorithms, for instance, can become more precise and accurate as they interact with training data, allowing humans to gain unprecedented insights into diagnostics, care processes, treatment variability, and patient outcomes. However, even organizations with industry-leading analytics competencies in hand are facing complex challenges when it comes to applying various analytics to clinical care. Moreover, due to the vast array of distributed network processing modalities and storage databases for respective medical images, relevant data (e.g., metadata, studies, AI analysis, other physician analysis) for a given image may not be linked or retrieved in order for the most comprehensive analysis of a given image. Also, collaboration and data sharing among professionals is often lost due to the inadequacies of current systems.

SUMMARY

The following presents a summary to provide a basic understanding of one or more examples of the invention. This summary is not intended to identify key or critical elements or delineate any scope of the different examples or any scope of the claims. Its sole purpose is to present concepts in a simplified form as a prelude to the more detailed description that is presented later. In one or more examples, systems, computer-implemented methods, apparatus and/or computer program products are described herein that facilitate integrating informatics into healthcare systems using a web-based medical image data platform that provides various services related to accessing, managing, and sharing anonymized medical image data to facilitate healthcare image processing and analysis.

According to an example, a system is provided that includes a memory that stores computer executable components. The system includes a processor that executes the computer executable components stored in the memory. The computer executable components include a plurality of endpoint databases employed to store medical images and metadata that describes attributes of the respective medical images, and a crawler component that periodically scans the endpoint databases to determine an index of recently acquired medical images and associated metadata to be searched in response to a search function. The crawler component also determines recent updates to metadata associated with previously stored medical images that is employed in current searches of the endpoint databases in response to the search function. The computer executable components further include a search component that executes the search function to retrieve at least one of the recently acquired medical images and associated metadata and the recent updates to metadata associated with the previously stored medical images.

In another example, a method includes scanning, by a system operatively coupled to a processor, a plurality of medical images and metadata from endpoint databases that describes attributes of the respective medical images. The method includes determining, by the system, an index of recently acquired medical images and associated metadata to be searched in response to a search function. The method includes determining, by the system, recent updates to metadata associated with previously stored medical images that is employed in current searches of the endpoint databases in response to the search function. The method includes retrieving, by the system, at least one of the recently acquired medical images and associated metadata and the recent updates to metadata associated with the previously stored medical images.

In another example, a non-transitory machine-readable storage medium comprising executable instructions that, when executed by a processor cause the processor to scan a plurality of medical images and metadata from endpoint databases that describes attributes of the respective medical images. The instructions determine an index of recently acquired medical images and associated metadata to be searched in response to a search function. The instructions determine recent updates to metadata associated with previously stored medical images that is employed in current searches of the endpoint databases in response to the search function. The instructions retrieve at least one of the recently acquired medical images and associated metadata and the recent updates to metadata associated with the previously stored medical images.

In another example, a system is provided that includes a memory that stores computer executable components. The system includes a processor that executes the computer executable components stored in the memory. The computer executable components include a plurality of storage endpoints that store medical images and an indexing component that generates a global data index that identifies the medical images respectively stored in the storage endpoints and associates metadata with the medical images that describes attributes of the medical images. The computer executable components further include an access component that provides access to the medical images via a web-platform, and a search component that employs the global data index to identify one or more of the medical images that satisfy one or more search criterion and generates search result data identifying the one or more medical images. The computer executable components further include a user interface component that presents the search result data via a graphical user interface of the web-platform.

In another example, a method is provided that includes providing, by a system operatively coupled to at least one processor, access via a web-platform to a plurality of storage endpoints that store medical images and generating, by the system, a global data index that identifies the medical images respectively stored in the storage endpoints and associates metadata with the medical images that describes attributes of the medical images. The method further includes employing, by the system, the global data index to identify one or more of the medical images that satisfy one or more search criterion, and providing, by the system, interactive search result data via user interface of the web-platform identifying the one or more medical images.

In some examples, elements described in connection with the disclosed systems can be embodied in different forms such as a computer-implemented method, a computer program product, or another form.

DESCRIPTION OF THE DRAWINGS

FIGS. 8A-8K present example search function user interfaces (UIs) in accordance with one or more embodiments of the disclosed subject matter.

FIGS. 9A-9C provide example search result UIs in accordance with one or more embodiments of the disclosed subject matter.

FIGS. 10A-10F present example medical image data viewer UIs in accordance with one or more embodiments of the disclosed subject matter.

FIG. 12 presents an example exam feed UI in accordance with one or more embodiments of the disclosed subject matter.

FIGS. 14A-14D present an example account management UIs in accordance with one or more embodiments of the disclosed subject matter.

DETAILED DESCRIPTION

Figure 1:
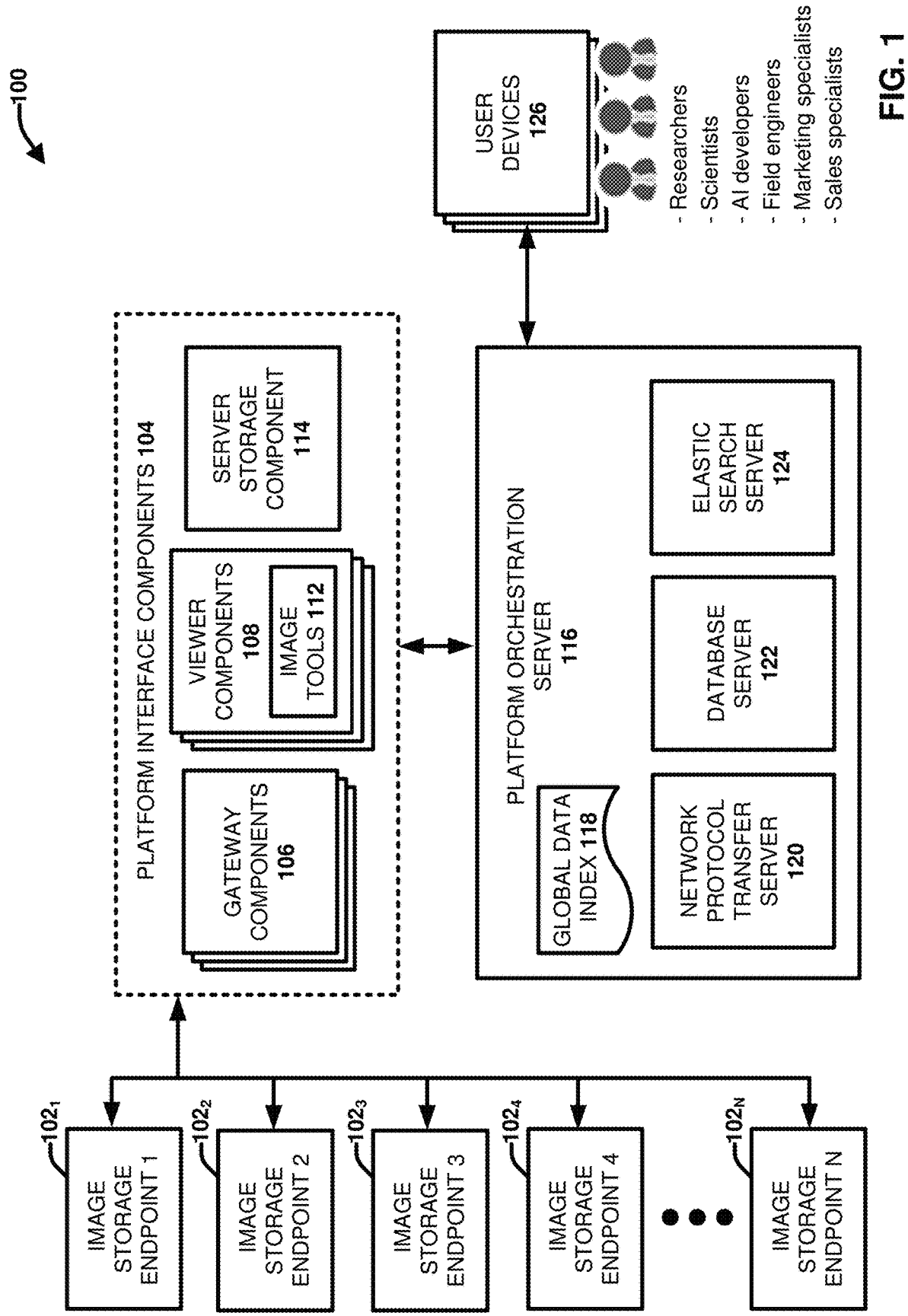
FIG. 1 illustrates a block diagram of an example system that provides various services related to accessing, managing, and sharing anonymized medical image data using a web platform in accordance with one or more embodiments of the disclosed subject matter.

The following detailed description is merely illustrative and is not intended to limit examples illustrated and described herein and/or application or uses of such examples. Furthermore, there is no intention to be bound by any expressed or implied information presented in the preceding Summary section or in the Detailed Description section.

The disclosed subject matter is directed to a web-based medical image data platform (hereinafter "the platform") that provides various services related to accessing, managing, and sharing anonymized medical image data to facilitate healthcare image processing and analysis and other applications. In various embodiments, the platform can be used by an organization to manage their medical images located at various disparate databases internally, as well as customers and research sites to manage their data across many different systems. In this regard, the platform can be used by content owners to access and retrieve their data stored at the various disparate databases as well as data suppliers to upload their data to a centralized, cloud-based repository. The platform can also serve as portal for people to shop for medical image data, share medical image data and exchange medical image. For example, the platform can be used to researchers, marketers, AI model developers and the like, to find and retrieve the specific type of medical image data they need for a particular project. The platform can also provide project management services and various collaborative, social networking type services. For example, the platform can facilitate collaborative review of medical image data, allowing users to rate and review the medical image data, annotate the medical image data, edit and augment the medical image data, and the like. The platform can also provide a forum for users to collaborate on projects, follow other users' activity related to usage of the platform, share information, and other social networking type features related to medical image data processing and analysis.

To facilitate this end, the platform employs a federated model to connect to many different types of medial image data storage endpoints such as for example, internal databases, third party databases, workstations, Picture Archiving and Communication Systems (PACS) and consoles, and so forth. These storage endpoints can be located on the same network, across multiple networks and regions around the world. The image data can be centrally represented while providing the ability to move across the organization between various types of endpoints and storages that can be implemented in a seamless manner. In particular, the platform indexes medial image data located at the disparate endpoints based on metadata tags (or simply metadata) respectively associated with the medical images describing highly detailed attributes of the medical images that makes them searchable in a standard and anonymized way across the disparate endpoints.

For example, each image can be associated with up to hundreds (or more) of metadata tags describing various attributes about the image that may be relevant to finding and/or using the image for research purposes, AI model development purposes, and various other non-clinical purposes. In this regard, the metadata tags can include image classifiers that provide a much higher level of granularity than those generally associated with medical images as used in clinical practice. For example, the metadata tags can include information regarding (but not limited to), image acquisition protocols, image quality, signal noise, image index size, matrix size, resolution, orientation, capture modality, type and dimensions of anatomical features depicted in the image data, image rating, image quality, image storage location (or locations), image capture time, and other features. The metadata tags can also include (but are not limited to) information describing the image type, the anatomical part depicted in the image data, the medical condition/pathology reflected in the image data, patient demographics, and relevant patient medical history factors. The platform can further structure the metadata into a standardized format (e.g., a Digital Imaging and Communications in Medicine (DICOM) standard format) to facilitate searchable results.

The platform provides various services including allowing content owners and third parties to search for, view, review, collect and share medical image data. In this regard, the platform allows medical image data content owners (e.g., an integrated medical system, a hospital, an individual) to manage and orchestrate a centralized and federated representation of their medical images and associated data and reports. The platform further allows content owners and third parties to upload, download, push, pull, review and collaborate on the federated data. The platform further provides advanced search features that allow users to efficiently find medial image data stored across their organization, networks, and/or different environments. The platform can further allow users to save advanced and expert searches and include a crawler function that monitors and finds new added data that satisfies their saved search criteria. The platform can further notify users regarding the newly identified data.

The platform can also provide a project creation function that allows users to create projects (e.g., a project involving a subset of the medical image data) and request medical image data they desire for their projects, including medical image data not yet available on the platform. In this regard, the platform includes executable instructions to at least one of enable AI developers and 3rd parties to create a project with specifics of the data related to their development and save searches in real time and periodically. This includes executable instructions to at least one of generate a global data index of a plurality of medical exams across globally deployed federated set of DICOM end points and automatically return data meeting specified criteria that can be accepted or declined.

The platform can further automate data finding, such as with respect to finding medical image data in various databases that satisfy defined criteria. For example, the platform can find protected health information (PHI) stored in the connected medical image data stores and edit the DICOM tags as needed to re-anonymize the data.

The platform further provides a collaborative environment in which users can review, discuss and annotate (e.g., with additional metadata tags) the medical image data accessible via the platform. In some embodiments, the platform can provide a rating feature that allows users to rate (or apply a score to) medical images in one or more categories, such as overall quality, resolution quality, artifact disturbances, signal noise, contrast ratio, acquisition quality, pathology clarity, and the like. This rating information can further be associated with respective images as metadata and used to find images of a desired rating (e.g., to find high quality images with a rating of X or higher). The platform can further provide a collaborative way for users to favorite, share, and store collections of medical image data/datasets. The platform can further provide analytics regarding collaboration.

In some embodiments, the platform can also provide an image dataset comparison function that compares datasets at the exam/series/instance level. The platform can also employ one or more intelligent algorithms that finds similar exams, series and/or images (e.g., by image quality, similar pathology or artifacts, and various other searchable attributes). The comparison function can also provide for finding and group duplicates by fingerprinting pixel data. The platform can further assign/manage permissions applied for each endpoint. The platform can further include executable instructions to at least one of share data, export data in large input and output formats and platforms (e.g., hypertext transfer protocol (HTTP) format, secure file transfer protocol (sFTP) format, Box format, DICOM format, and so forth), initiate smart searches (e.g., Google-like Advanced image viewing), synchronize workstations with PACS or other systems automatically, backup workstation, and display difference between at least two endpoints. In some embodiments, the platform can also include executable instructions to apply automated AI models to create new indexable data based on the images, recognize the anatomy on each image, recognize image type, and recognize artifacts. The platform can also include executable instructions to recognize whether there's pathology, automatically rate series/exams, assign criteria finding duplicates and fingerprinting data, and execute intelligent algorithms to find similar series (and exams) based on user preferences. The platform further includes instructions to assign acquisition parameters (similar resolution, timings, dose, and so forth), by image quality (similar SNR, similar resolution, similar CNR).

The platform can further execute intelligent algorithms where users can upload an image with a pathology or artifacts, find similar images, and view feedback via a Dashboard. The platform can include instructions to provides user and data feeds that follow one user or a group of users, see their activity, watch for data activity (e.g., new data landed, when, where with a calendar view), and so forth, and provide mobile application and interfaces to the platform. The platform further includes executable instructions to at least one of review, preview, add to a cart, and/or download the medical images and/or metadata. The platform includes executable instructions to move data to a dedicated workstation for AI development.

The term "web platform" as used herein refers to any platform that enables delivery of content and services over a network (web (i.e., the web/Internet) using a network transfer protocol, such as HTTP, sFTP, or another network transfer protocol. For example, a web platform can include, but is not limited to, a web-application (i.e., an interactive website), a mobile website, a mobile application or the like. The terms "web platform," "web-based platform," "network platform," "platform," and the like are used herein. interchangeably unless context warrants particular distinction amongst the terms.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 illustrates a block diagram of an example system 100 that provides various services related to accessing, managing, and sharing anonymized medical image data using a web platform in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

System 100 includes a plurality of image storage endpoints 102, platform interface components 104, platform orchestration server 116 and user devices 126. The image storage endpoints can include essentially any data source that stores medical images and/or information related to the medical images, such as metadata describing various attributes of the medical images, radiology reports associated with the medical images, relevant patient information, and the like. These image storage endpoints 102 can comprise different types of data sources that are provided by the same entity/organization that owns/operates the platform orchestration server 116 and/or the platform interface component 104, as well as provided by various different third party or external entities/organizations. For example, the image storage endpoints 102 can include internal databases, external databases, internal and external workstations, internal and external PACS and consoles, and so forth. These image storage endpoints 102 can be located on the same network as well as across multiple networks and regions around the world. The number N of image storage endpoints 102 is unlimited.

In this regard, the term "internal" as applied to an image storage endpoint 102 or another data source is used herein to refer to a proprietary data source/system associated with a single enterprise that owns, provides, manages and/or controls the features and functionalities of the platform orchestration server 116 and/or the platform interface component 104. For example, in some implementations, the single enterprise can be a health information technology (HIT) company (such as General Electric (GE) Healthcare Corporation) that provides a range of products and services that include medical imaging and information technologies, electronic medical records, medical diagnostics, patient monitoring systems, drug discovery, biopharmaceutical manufacturing technologies and the like. According to this example, the HIT company can also provide, manage, and/or control the platform orchestration server 116 and/or the platform interface component 104 in addition to the provision of their internal healthcare data for used in developing or training healthcare AI models. In another implementation, the single enterprise can comprise a hospital organization that provides medical services to patients via one or more hospitals, outpatient medical facilities, and the like. Regardless of the nature, operations and/or services provided by the enterprise, the image storage endpoints 102 can comprise internal data sources/systems that are owned and/or operated by that enterprise.

The image storage endpoints 102 can also include one or more external data sources/systems. The term "external" as applied to an image storage endpoints 102 or another data sources is used herein to refer a data source or system that is owned and/or operated by a third party entity that does not provide, manage, and/or control the platform orchestration server 116 and/or the platform interface component 104. In this regard, the image storage endpoints 102 can amass various healthcare data sources and systems provided by same and different enterprises/entities at various locations around the world (and/or in the cloud) to enable access to medical image data via the web platform provided by the platform orchestration server 116 for various purposes.

In various embodiments, the image storage endpoints 102 can store medical images formatted according to the DICOM standard. DICOM is the worldwide standard for handling, storing, printing, and transmitting information in medical imaging. It includes a file format definition and a network communications protocol. DICOM is used worldwide to store, exchange, and transmit medical images. For example, DICOM incorporates standards for the various imaging modalities such as radiography, ultrasonography, computed tomography, magnetic resonance, mammograph, and the like. DICOM includes protocols for image exchange (e.g., via portable media such as DVDs), image compression, 3D visualization, image presentation, and results reporting. Working with imaging data sets of size and complexity scales needed to develop sophisticated AI imaging diagnostic models can be somewhat easier than with other types of datasets due to the wide adoption of DICOM, a standard that has been in place for medical imaging for more than twenty years. For imaging, DICOM fills the role of connecting all the modalities in the hospital. The printers, displays, MRI machines, and other acquisition devices all communicate using DICOM standards. In some embodiments, the image storage endpoints 102 can additionally or alternatively store native medical images. As used herein, a "native medical image" or "native medical image data" refers to any image data captured by a medical imaging capture device or medical imaging acquisition device that is not necessarily formatted according to DICOM standards.

The medical images provided by the image storage endpoints 102 can include images captured using essentially any medical imaging modality. For example, the medical images can include but are not limited to: conventional X-ray (XR) images, digital radiography (DX) X-ray images, X-ray angiography (XA) device, panoramic X-ray (PX) images, computerized tomography (CT) images, mammography (MG) images, (including a tomosynthesis device), magnetic resonance imaging (MRI) images, ultrasound (US) images, color flow doppler (CD) images, position emission tomography (PET) images, single-photon emissions computed tomography (SPECT) images, nuclear medicine (NM) images, and other types of medical images. The medical images can also include or be associated with (e.g., as metadata) raw pixel data, waveform data, three-dimensional or depth data, point cloud data and the like.

In some embodiments, the medical images provided by the image storage endpoints 102 can include annotated medical images. Annotated images can include DICOM images and/or native images with some form of annotation or mark-up applied thereto and/or associated therewith (e.g., as metadata, as a separate file, etc.). The annotation or mark-up can include graphical marks, tags, textual tags, text data, symbol data, audio data, and the like, applied to defined points, areas or volumes of interest in an image.

In some implementations, the image storage endpoints 102 can comprise one or more PACSs. A PACS provides economical storage and convenient access to images from multiple modalities (source machine types). Electronic images and reports can be transmitted digitally via a PACS, which eliminates the need to manually file, retrieve, or transport film jackets, the folders used to store and protect X-ray film. The universal format for PACS image storage and transfer is DICOM. Non-image data, such as scanned documents, may be incorporated using consumer industry standard formats like PDF (Portable Document Format), once encapsulated in DICOM.

The image storage endpoints 102 can also include one or more a vendor neutral archive (VNA) systems. A VNA is a medical imaging technology in which images and documents (and potentially any file of clinical relevance) are stored (archived) in a standard format with a standard interface, such that they can be accessed in a vendor-neutral manner by other systems. In this regard, VNAs can collect and store images from multiple modalities and departments (e.g., radiology, cardiology, orthopedic, etc.) and pull everything into one big archive. In addition to DICOM images, VNAs can store data objects not directly related to images or DICOM data, such as human-generated requests and reports, health level 23 clinical document architecture (HL23-CDA) documents, and the like. The VNAs can also employ non-DICOM access protocols, such as Cross-Enterprise Document Sharing (XDS and XDS-I). VNAs can also provide cross-domain identity and code resolution (patient ID, accession number, procedure codes), dynamic DICOM tag morphing, and other adaptable features. The image storage endpoints 102 can also include workstations (e.g., deployed at one or more computing devices) where medical images are viewed and/or processed for various purposes (e.g., AI model development workstations, radiologist viewer workstations, annotation workstations, etc.).

The platform orchestration server 116 employs a web-based platform to provide various services to users related to accessing, managing, and sharing medical images and associated data stored at the image storage endpoints 102. For example, the web-based platform can allow users to access, browse, view, search for, collect, review, edit, and download medical image data stored at the image storage endpoints 102 using their respective user devices 126. To facilitate this end, platform orchestration sever 116 employs a global data index 118 that indexes the medial image data located at the disparate endpoints based on metadata tags (or simply metadata) respectively associated with the medical images describing highly detailed attributes of the medical images that makes them searchable in a standard and anonymized way across the disparate endpoints.

For example, the medical images stored located at the one or more image storage endpoints 102 can be associated with up to hundreds (or more) of metadata tags describing various attributes about the image that may be relevant to finding and/or using the image for research purposes, AI model development purposes, and various other non-clinical purposes. In this regard, the metadata tags can include image classifiers that provide a much higher level of granularity than those generally associated with medical images as used in clinical practice. For example, the metadata tags can include information regarding (but not limited to), image acquisition protocols, image quality, signal noise, image index size, matrix size, resolution, orientation, capture modality, type and dimensions of anatomical features depicted in the image data, image rating, image quality, image storage location (or locations), image capture time, and other features. In another example, the metadata tags can include information describing annotations applied to the medical images. The metadata tags can also include (but are not limited to), information describing the image type, the anatomical part depicted in the image data, the medical condition/pathology reflected in the image data, patient demographics, and relevant patient medical history factors. In this regard, the metadata tags associated with the respective images can include essentially any definable attribute or characteristic associated with the image itself (e.g., imaging parameters/features, acquisition parameters, pixel data, capture modality, capture location, rating, etc.), the anatomical part depicted in the image, the clinical pathology represented in the image, and the patient.

In one or more embodiments, the global data index 118 can provide indexed information that identifies the images stored in the image storage endpoints via one or more unique DICOM identifiers. In various embodiments, the identifiers can anonymize the images (e.g., replacing patient names with alternative identifiers). The global data index 118 can further identify the image storage endpoint or endpoints 102 where each image is store and identify the various metadata tags associated with each (or in some implementations one or more) image in accordance with a standardized format (e.g., the DICOM format), thereby making them searchable in a standard and anonymized way across the image storage endpoints 102. As described in greater detail infra with reference to FIG. 6, in various embodiments the platform orchestration server 116 can generate and/or continuously update the global data index 118 based reception of new medical images at the image storage endpoints 102 and/or new information about the medical images. Accordingly, the indexed metadata provides for a powerful repository (e.g., data lake) that can serve as a portal to source clinical data across the planet. There are numerous applications (e.g., product development, diagnostics, teaching, presentation, marketing, insurance claims, documenting, prognostics . . . ), and a platform providing such functionality can be utilized by numerous associated practitioners that utilize clinical data The platform orchestration server 116 can also employ the web-based platform to also allow users to upload (e.g., using their respective user devices 126) medical image data for storing by the platform orchestration server 116 (e.g., using storage server component 114) and/or pushing to one or more of the image storage endpoints 102. For example, the web-based platform can be used by researchers, scientists, AI developers, field engineers, marking specialists, sales specialists and the like to find and retrieve medical image data stored at one or more of the image storage endpoints 102 that they need for a particular project (e.g., a research project, an AI model development project, etc.). The web-based platform can be used by data suppliers to upload their data to one or more of the image storage endpoints 102. The web-based platform can also be used by researchers, scientists, AI developers, and the like to share data and collaborate on projects. These operations and additional operations the platform orchestration server 116 are described in greater detail infra with reference to FIG. 6.

In various embodiments, the web-based platform can be or correspond to an interactive web application that can be accessed by users using a suitable computing device including a browser (e.g., user devices 126). Additionally, or alternatively, the web-based platform can be or correspond to a mobile application such as a thin client application, a thick client application, a native client application, a hybrid client application, or the like. In either of these embodiments, the platform orchestration server 116 can be or include one or more server devices/machines to execute and/or facilitate execution of the various operations of the web-based platform. For example, in the embodiment shown, the platform orchestration server 116 can include a network protocol transfer server 120, a database server 122 and an elastic search server 124. The network protocol transfer server 118 can facilitate data communication between the platform orchestration server 116 and other systems, sources, components, devise, etc. in accordance with a standard network transfer protocol (e.g., HTTP, sFTP, and similar protocols). The database server 120 can facilitate transferring data (e.g., medical images) between data sources, including between image storage endpoints 102 and one or more databases of the platform orchestration server 116 (e.g., the server storage component 114). The elastic search server 122 can provide an elastic search function to facilitate efficient searching for medical images stored in the image storage endpoints 102 based on highly granular search criteria and the plethora (e.g., hundreds or more) of metadata tags that can be associated with the medical images.

The platform interface components 104 can provide various intermediary functions that support and/or enable one or more features and functionalities of the platform orchestration server 116. For example, the platform interface components 104 can include one or more gateway component 106 that facilitate connecting the platform orchestration server 116 to the image storage endpoints 102. The platform interface component 104 can also include at least one server storage component 114 that can be or correspond to a server database that can store information used by the platform orchestration server 116. For example, in some embodiments the server storage component 114 can server as local cache that stores instances of images retrieved from one or more of the image storage endpoints 102 in association with viewing and interacting with the images using the view components 108. In another example, the server storage component 114 can store any data generated by and/or used by the platform orchestration server 116.

The platform interface components 104 can also include one or more viewer components 108 that provide the image tools 112 needed for viewing and interacting with medical image data stored at the image storage endpoints 102 and/or the server storage component 114. For example, in various embodiments, the viewer components 108 can respectively be or correspond to medical image view applications/programs that can be accessed using the web-based platform employed by the platform orchestration server 116 (e.g., as a plug-in application or the like). The viewer components 108 can include software and/or hardware components that facilitate viewing the medical images stored at the images storage endpoints and can optionally provide various interactive features for interacting with the images (e.g., changing perspectives, editing the images, applying annotations, etc.). For example, in some implementations, the viewer components 108 can provide annotation tools for annotating medical images, tools for applying and/or editing DICOM tags, and tools for reviewing/rating the medical images.

In some examples, the viewer components 108 can be configured to generate and/or provide reconstructed medical images. As used herein, reconstructed medical images refers to a computer-generated medical image generated based on one or more native medical images. A reconstructed medical image generally refers to a 3D model or volumetric rendering (VR) generated based on several combined native medical images.

The deployment architecture system 100 and other system described herein can vary. In some embodiments, the system can be deployed in a cloud architecture, a virtualized enterprise architecture, or an enterprise architecture wherein one or more features and functionalities of the platform orchestration server 116 and/or the platform interface components 104 are accessed by the user devices 126 using a server/client relationship.

In this regard, the image storage endpoints 102, the platform interface component 104, the platform orchestration server 116, and the user devices 126 can be communicatively coupled directly and/or via one or more networks (not shown). For example, the one or more network can include wired and wireless networks, including but not limited to, a cellular network, a wide area network (WAD, e.g., the Internet), a virtual private network (VPN), a local area network (LAN), or the like. The one or more networks can enable communication between the respective components and devices of system 100 (e.g., the image storage endpoints 102, the platform interface component 104, the platform orchestration server 116, and the user devices 126) using virtually any desired wired or wireless technology, including but not limited to: wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), fourth generation partnership project (4GPP), fifth generation partnership project (4GPP), ultra mobile broadband (UMB), high speed packet access (HSPA), Zigbee and other 802.XX wireless technologies and/or legacy telecommunication technologies, BLUETOOTH®, Session Initiation Protocol (SIP), ZIGBEE®, RF4CE protocol, WirelessHART protocol, 6LoWPAN (IPv6 over Low power Wireless Area Networks), Z-Wave, an ANT, an ultra-wideband (UWB) standard protocol, and/or other proprietary and non-proprietary communication protocols.

The respective components and devices of system 100 can thus include or be operatively coupled to hardware (e.g., a central processing unit (CPU), a transceiver, a decoder), software (e.g., a set of threads, a set of processes, software in execution) or a combination of hardware and software that facilitates wired and/or wireless communication using one or more communication technologies. The user devices 126 can include any suitable computing device (or group of computing devices) configured to receive user input and interface with the platform orchestration server 126 to employ the features and functionalities thereof. For example, the user devices 126 can be or include a desktop computer, a laptop computer, a kiosk, a television, an Internet enabled television, a mobile phone, a smartphone, a tablet personal computer (PC), or a personal digital assistant (PDA), a heads-up display (HUD), an augmented reality (AR) device, a virtual reality (VR) device, a wearable device, and the like.

Figure 2:
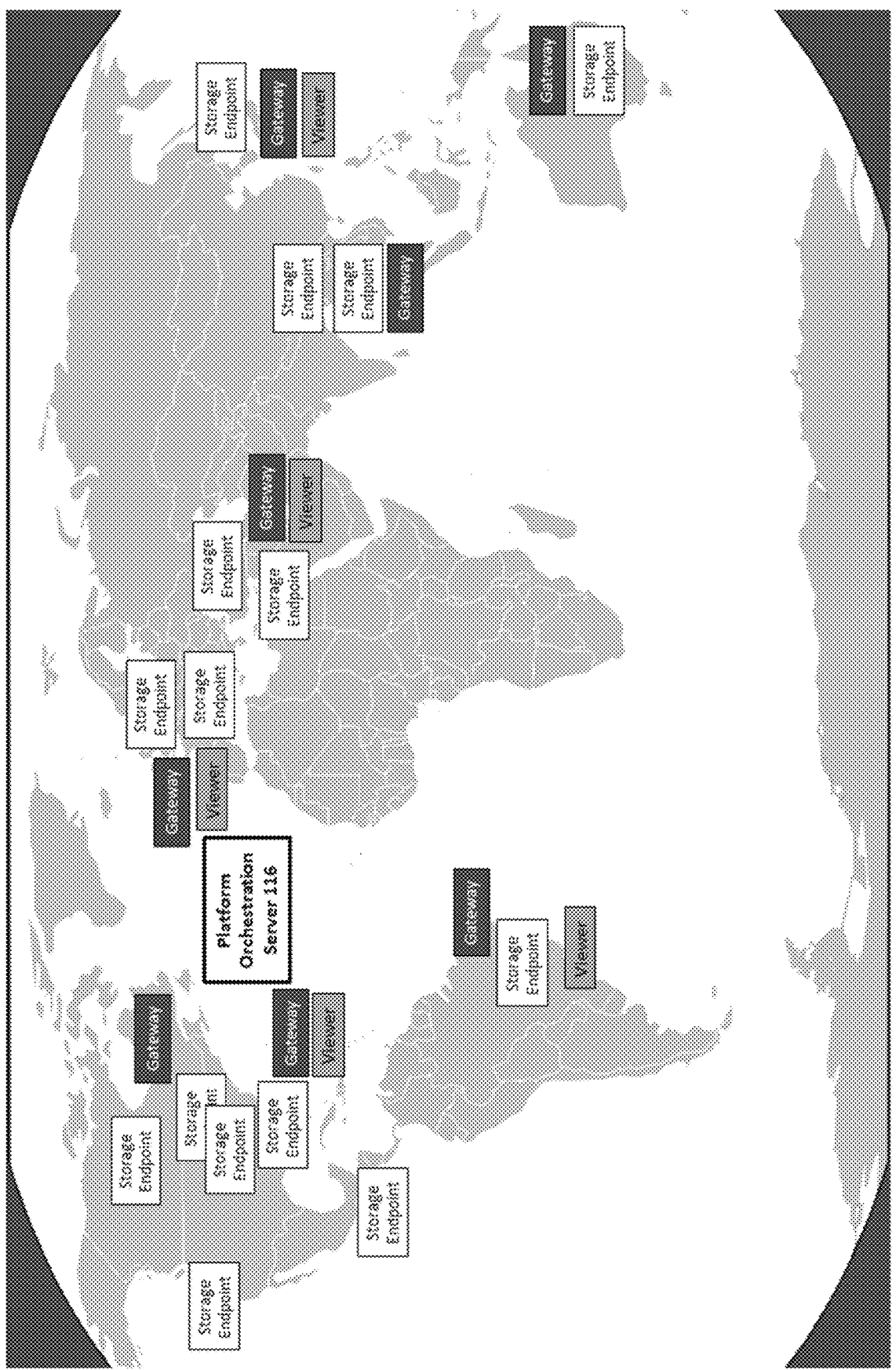
FIG. 2 illustrates an example worldwide infrastructure view of an example system that provides various services related to accessing, managing, and sharing anonymized medical image data using a web platform in accordance with one or more embodiments of the disclosed subject matter.

FIG. 2 illustrates an example worldwide infrastructure view of an example system (e.g., system 100) that provides various services related to accessing, managing, and sharing anonymized medical image data using a web platform in accordance with one or more embodiments of the disclosed subject matter. With reference to FIG. 2 in view of FIG. 1, in the embodiment shown in FIG. 2, the storage endpoints can respectively be or correspond to the image storage endpoints 102, the gateways can respectively be or correspond to the gateway components 106, and the viewers can respectively be or correspond to the view components 108. With this example, architecture, the platform orchestration server 116 can be or correspond to a cloud-based server that operates as a centralized server to manage and control access to the storage endpoints and the viewers via the gateways.

Figure 3:
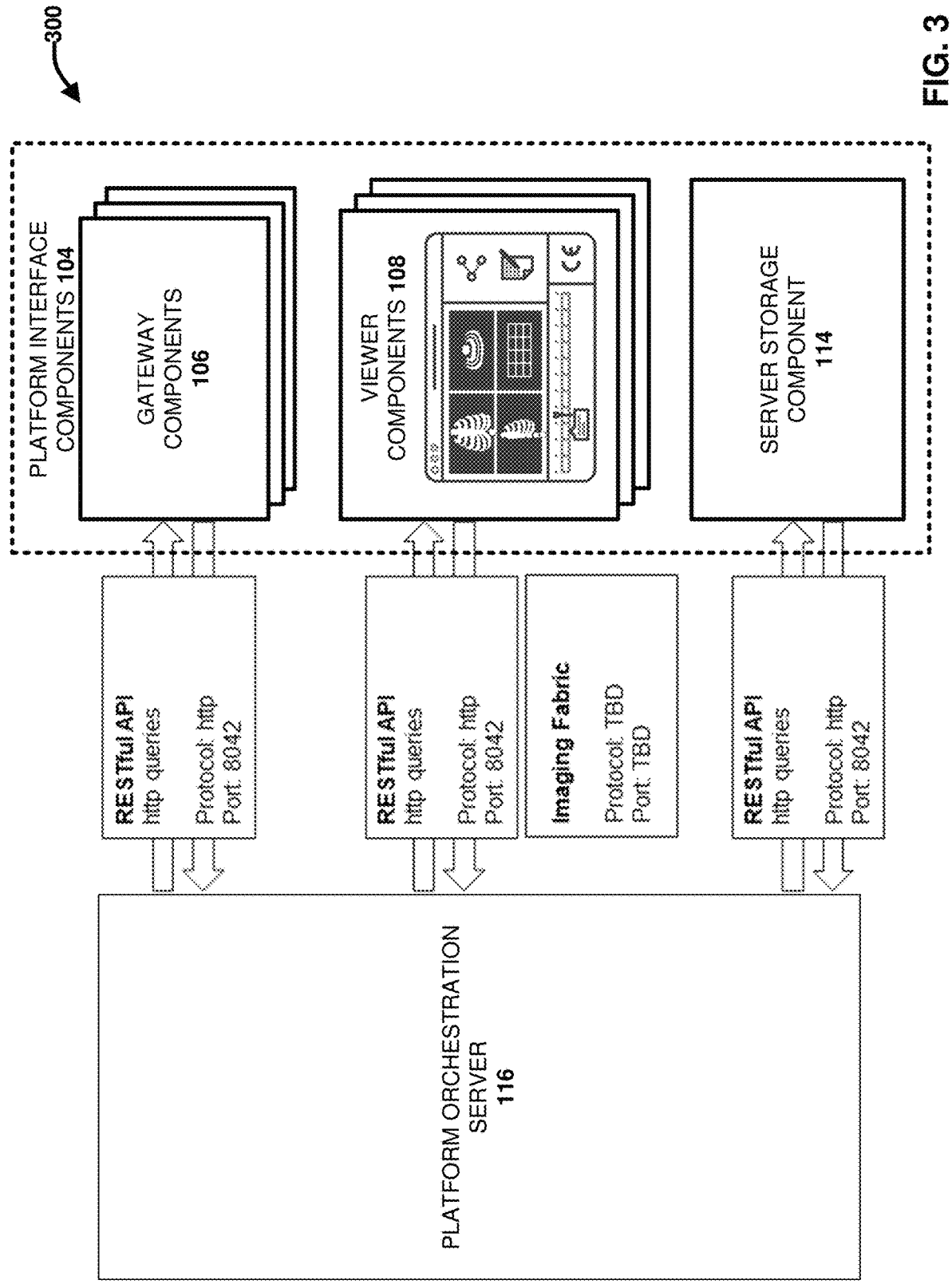
FIG. 3 presents a diagram illustrating interaction of the platform orchestration server with the platform interface components in accordance with one or more embodiments of the disclosed subject matter.

FIG. 3 presents a diagram 300 illustrating interaction of the platform orchestration server 116 with the platform interface components 104 in accordance with one or more embodiments of the disclosed subject matter. In this example, the representational state transfer (REST) application program interface (API) calls can be employed to transfer data to and from the gateway component 106, the viewer component 108, and the at least one server storage component 114.

Figure 4:
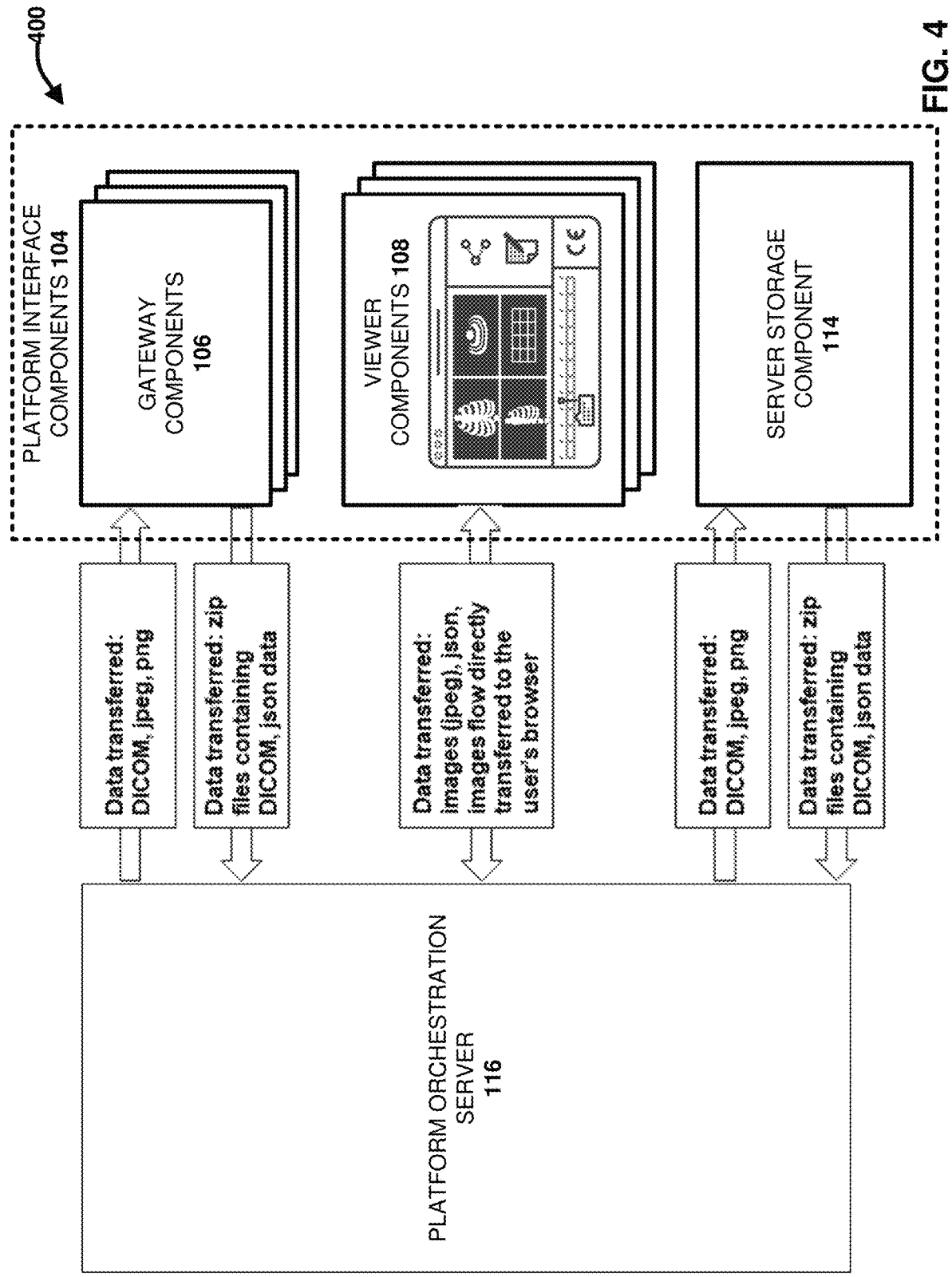
FIG. 4 presents a diagram illustrating data flow between the platform orchestration server and the platform interface components in accordance with one or more embodiments of the disclosed subject matter.

FIG. 4 presents a diagram 400 illustrating data flow between the platform orchestration server 116 and the platform interface components 104 in accordance with one or more embodiments of the disclosed subject matter. In this example, the platform orchestration server 116 generally transfers DICOM, JPEG, and PNG data to the gateway components 106 and the server storages components 114 and receives zip files containing such data and JSON data from these components. The platform orchestration server and the viewer components 106 further facilitate the flow of images (e.g., including JPEG and JSON images) directly to the user's browser.

Figure 5:
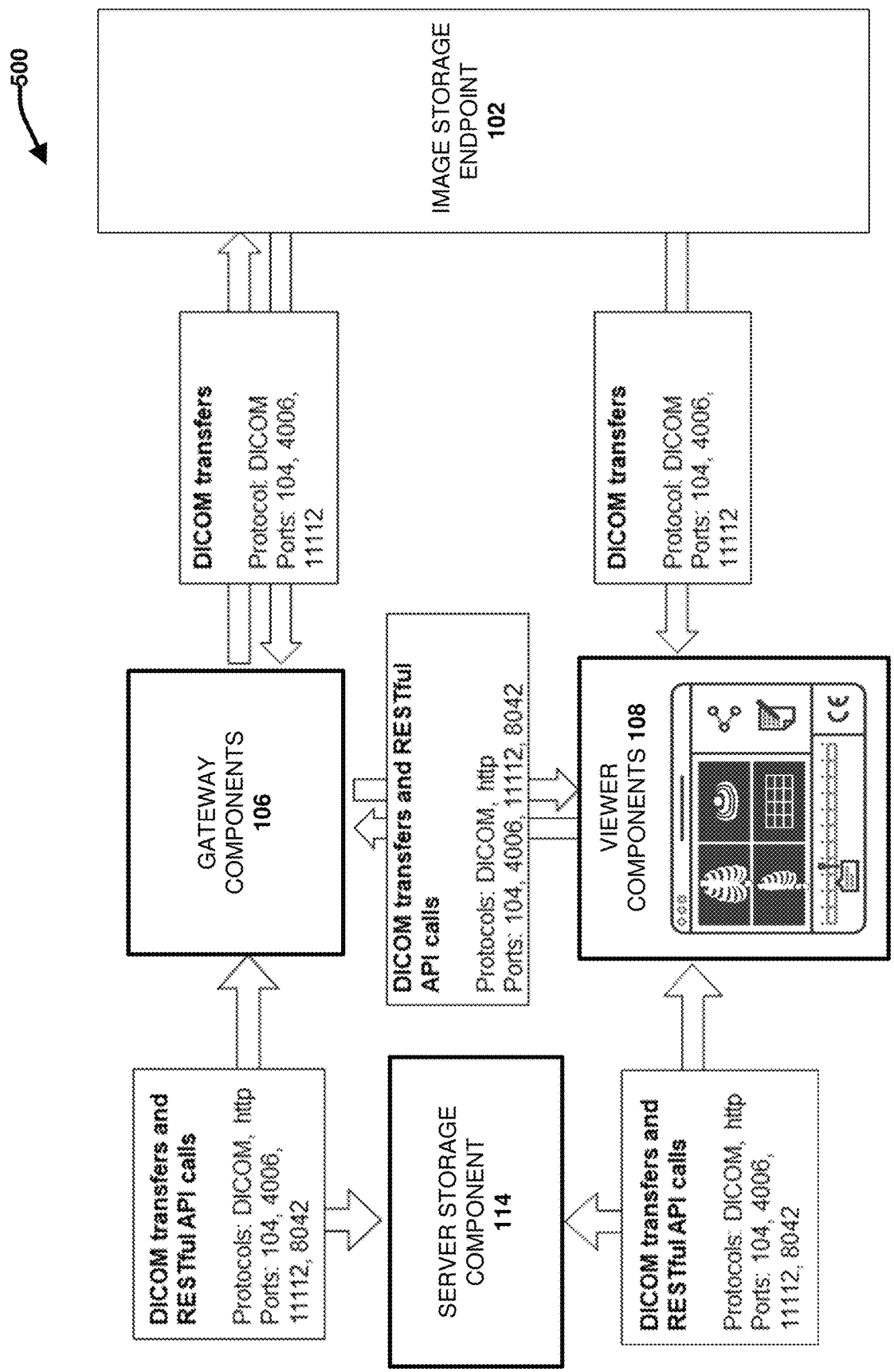
FIG. 5 presents a diagram illustrating data flow between the platform interface components and an image storage endpoint in accordance with one or more embodiments of the disclosed subject matter.

FIG. 5 presents a diagram 500 illustrating data flow between the platform interface components and an image storage endpoint 102 in accordance with one or more embodiments of the disclosed subject matter. In this example, various DICOM data transfers are executed between the image storage endpoint 102, the gateway components 106, the viewer components 108 and the server storage component 114 using REST API calls.

Figure 6:
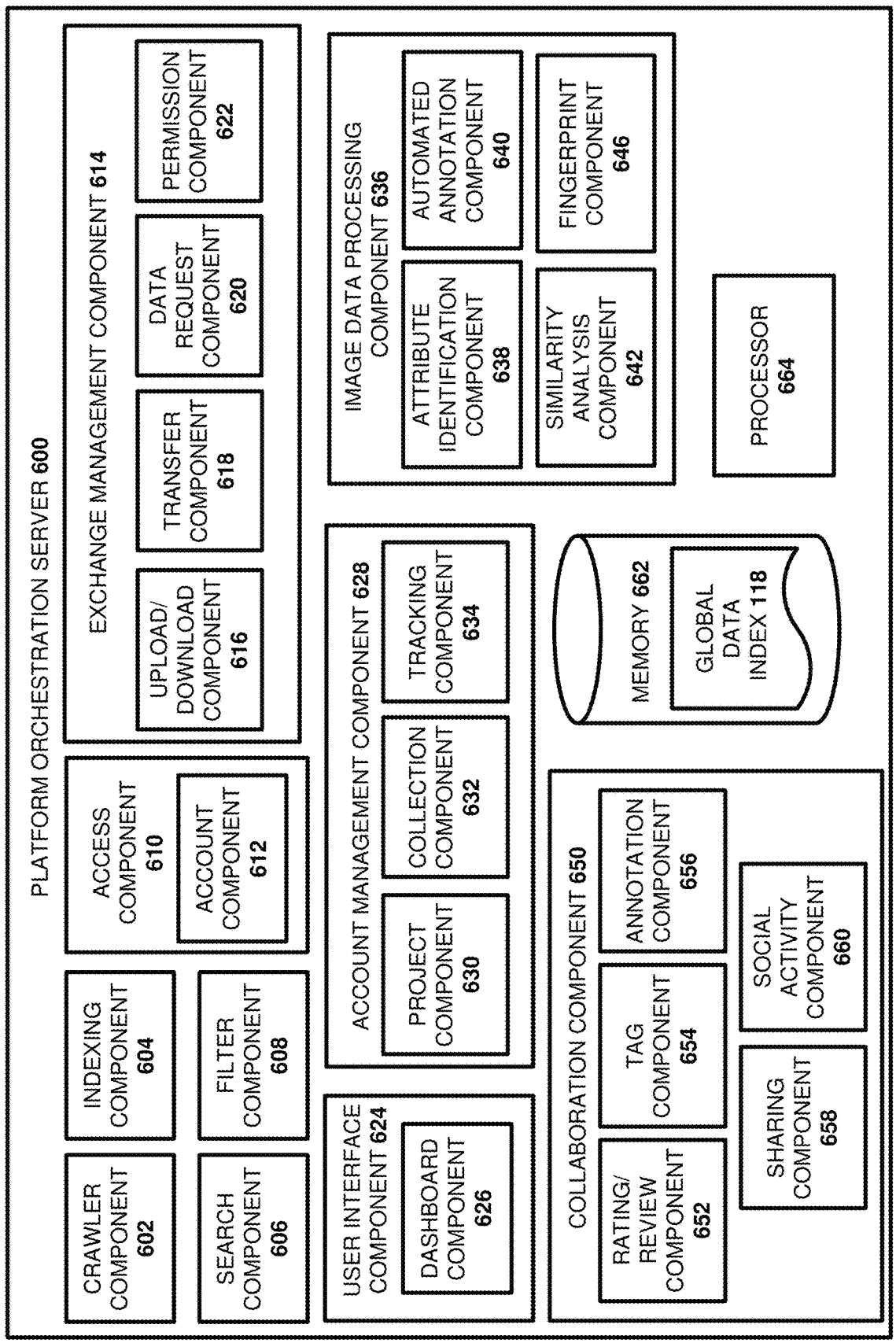
FIG. 6 illustrates a block diagram of an example platform orchestration server in accordance with one or more embodiments of the disclosed subject matter.

FIG. 6 illustrates a block diagram of an example platform orchestration server 600 in accordance with one or more embodiments of the disclosed subject matter. In various embodiments, platform orchestration server 600 can be or correspond to platform orchestration server 116. In this regard, platform orchestration server 600 can provide one or more of the features and functionalities of platform orchestration server 116, or vice versa. Repetitive description of like elements employed in respective embodiments is omitted for sake of brevity.

Platform orchestration server 600 includes several computer executable components that respectively provide various computer executable functions of the disclosed web platform for accessing, managing, and sharing anonymized medical image data to facilitate healthcare image processing and analysis. In the embodiment shown, these computer executable components include crawler component 602, indexing component 604, search component 606, filter component 606, access component 610, exchange management component 614, user interface component 624, account management component 628, image data processing component 636 and collaboration component 650. The platform orchestration server 600 further includes at least one memory 662 that stores computer executable components as described herein, and at least one processor 664 that executes the computer executable components stored in the memory. In the embodiment shown, the at least one memory 662 can store the global data index 118. However, the global data index 118 or an instance of the global data index 118 can be located in any datastore accessible to the platform orchestration server 600. Examples of said and memory 662 and processor 664 can be found with reference to FIG. 22, as well as other suitable computer or computing-based elements that can be used in connection with implementing one or more of the systems or components shown and described in connection with FIG. 6 or other figures disclosed herein.

It should be appreciated that various embodiments of the platform orchestration server 600 can include subsets of these components. In addition, the platform orchestration server 600 employ a plurality of devices/machines to execute different subsets of the components in a distributed and/or parallel computing environment. For example, in some embodiments, the platform orchestration server 600 can employ a plurality of sub-servers (e.g., network protocol transfer server 118, database server 120, elastic search server 122, and the like), wherein the respective sub-servers execute different subsets or groupings of these components.

With reference to FIGS. 1 and 6, in various embodiments, the indexing component 604 can generate the global data index 118 based on extraction of information identifying the images and the metadata associated therewith as included in the image storage endpoints 102. In some implementations of these embodiments, the crawler component 602 can scan the image storage endpoints 102 to identify medical images included therein. For example, the crawler component 602 can identify medical exam data sets, medical image series data sets, and individual medical images stored in the respective image storage endpoints. The crawler component 602 can further identify and extract the metadata tags associated with each exam, series, and/or individual image as stored in the image storage endpoints 102 describing attributes of the image data. For example, a DICOM file typically contains metadata with patient, exam/study, series and image information as well as image pixel data. In this regard, the crawler component 602 can identify and extract metadata tags associated with each exam, series, and/or image describing various attributes associated therewith.

The indexing component 604 can further generate the global data index 118 based on the information identified/extracted from the crawler component 602. For example, the global data index 118 can identify each exam, series, and/or individual image stored in the respective image storage endpoints 102, its storage location or locations (e.g., the image storage endpoint or endpoints 102 where they are stored), and the various metadata tags extracted for each exam, series and/or individual image. In some embodiments, the indexing component 604 can employ unique identifiers for each exam, series and/or individual image in accordance with a defined and standardized naming ontology, such as the DICOM standard or a similar standard. In this regard, in some embodiments, the unique identifier for an exam, series and/or image can correspond to the same name of the image file as it was stored at an image storage endpoint (e.g., in implementations in which it was stored in the correct format). In other embodiments, the indexing component 604 can change the file name in the global data index 118 in accordance with the standardized naming ontology employed by the system. In some implementations of these embodiments, the indexing component 604 can anonymize the image data in the global data index 118, removing any PHI that associates the image data with a particular patient (e.g., removing patient identifying information).

In this regard, protected health information (PHI) is the term given to health data created, received, stored, or transmitted by entities and their business associates that is protected under the Health Insurance portability and Accountability Act (HIPAA) privacy rule. Under HIPAA, PHI includes individually identifiable health information used to identify a patient. The HIPAA compliant way to de-identify PHI is to remove specific PHI identifiers from the data set, which include:

- Names
- Geographic subdivisions smaller than a state
- All elements of dates (except year) related to an individual (including admission and discharge dates, birthdate, date of death, all ages over 89 years old, and elements of dates (including year) that are indicative of age)
- Telephone, cellphone, and fax numbers
- Email addresses
- IP addresses
- Social Security numbers
- Medical record numbers
- Health plan beneficiary numbers
- Device identifiers and serial numbers
- Certificate/license numbers
- Account numbers
- Vehicle identifiers and serial numbers including license plates
- Website URLs
- Full face photos and comparable images
- Biometric identifiers (including finger and voice prints)
- Any unique identifying numbers, characteristics or codes In one or more embodiments, the crawler component 602 can identify medical image exam files, series files, and/or individual images that are stored at an image storage endpoint 102 with PHI associated therewith (e.g., stored one or more PHI identifiers). The crawler component 602 can employ various techniques to identify PHI, including usage of one or more explicitly trained or implicitly trained ML models/algorithms, one or more heuristic-based models/algorithms, and/or one or more external databases and search tools that can be used to screen potential PHI against. The crawler component 602 can further direct the indexing component 604 to remove any identified PHI from an image or image data set (e.g., an exam or series) to anonymize the data in the global data index 118 (e.g., remove any PHI metadata tags and/or PHI identifiers for the image data in the global data index 118). In some implementations, the crawler component 602 can further propagate changes to tags and/or file names removing PHI to the data file at is storage location (e.g., at one or more of the image data endpoints 102). In other implementations, the crawler component 602 can also notify the image file provider/owner and/or one or more system administrators regarding the identified image data file with the PHI associated therewith so that they may manually remove the PHI from where the data file is stored (e.g., at one or more of the image storage endpoints 102). Additionally, or alternatively, the indexing component 604 can be configured to prevent inclusion of image data references with PHI associated therewith in the global data index 118 so that they are not searchable and accessible to users via the platform. Still in other embodiments, the indexing component 604 can include an anonymized representation of the image data in the global index 118 so that it can be searched in an anonymized way, yet flag the image data as containing PHI in the global data index. With these embodiments, the exchange management component 614 can prevent certain actions for PHI flagged medical image data, such as but not limited to, viewing the medical image data, accessing the PHI information associated with the medical image data, downloading the medical image data, sharing the medical image data and the like.

The crawler component 602 can further regularly or periodically scan the image storage endpoints 102 to identify newly added images (e.g., new exams, studies, and/or individual images added to the image storage endpoints 102) and/or to identify updates to the metadata associated with previously indexed medical image data. In this regard, the indexing component 604 can regularly or continuously update the global data index 118 as new medical images are received and/or as new metadata is applied to the previously indexed medical images. Accordingly, as new input and new data is gathered (from human input and/or model input) by the crawler component 602, the indexing component 604 can update the global data index to further increase the collective knowledge of the system 100.

The search component 606 can employ the global data index 118 to provide one or more search functions for finding medical images stored in the image storage endpoints 102 that satisfy one or more defined search criterion. For example, the search component 606 can be or correspond to a search engine that receives a search request identifying one or more criterion for images that a user would like to find for a particular project. The one or more criterion can include for example, one or more desired attributes of the images, key words included in the image name, key words included in the image description or the like. In various embodiments, the search request can be received via a search UI of the web platform generated by the user interface component 624. The search component 606 can further employ the metadata tags associated with the images in the global data index 118 to identify any images stored in the image storage endpoints 102 that satisfy the search criteria. The search component 606 can further generate search result information identifying the images found which satisfy the search criteria which can be presented to the user via a search results UI generated by the user interface component 624.

In some implementations, the search component 606 can perform keyword searches based on free form user input. In other embodiments, the search component 606 can provide predefined, selectable search criteria that can be used to generate a search request. For example, the predefined search criteria can be based on the different metadata tags associated with the respective images represented in the global data index 118. In some embodiments, the search component 606 can provide an elastic search function. With these embodiments, the search component 606 can provide an advance search function via which users can build an advanced search query using an adaptable query building UI provided by the user interface component 624. The adaptable query building UI can allow a user to select/input specific search criterion and term operators in a guided manner that facilitates forming an elastic search on the back end. With these embodiments, the search component 106 can employ the elastic search server 124 to form and/or execute the elastic search based on the received user input. This searching mechanism increases the efficiency of the search component 606 on big data sets such as that provided by the image storage endpoints 102. For example, a single image storage endpoint 102 could store thousands of exams (or more), wherein each exam could contain up to 20 series (or more), wherein each series can contain up to around 10,000 images (or more) and wherein each image can contain more than 350 metadata tags.

In some embodiments, the search component 606 can regularly and/or continuously run saved search requests to find new results over time. For example, the search component 606 can allow a user to save a search that can be regularly run by the search component 606 according to defined schedule (e.g., once an hour, once a day, once a week, etc.) as new image data is received at the image storage endpoints 102, and/or as new metadata tags are received for previously indexed images. The search component 606 can further provide the user with the updated search results as the are received and/or notify the user of the updated search results.

The filter component 608 can provide one or more filter functions to filter search results based on one or more criterion. For example, in some embodiments, the filter component 608 can provide defined filter criteria that can be selected and used to further filter search results returned by the search component 606.

The platform orchestration server 600 can include user interface component 624 to facilitate generating and providing various user interfaces of the web-based platform (e.g., a web application, a mobile application, or the like) in association usage of the features and functionalities of the web-based platform. For example, the user interface component 624 can generate one or more search user interfaces that facilitate receiving user input defining a search request and associated search criteria. The user interface component 624 can also generate one or more search result user interfaces that organizes and present the search results and allows the user to select/apply additional filters to the search results. The user interface component 624 can also connect a user/user device 126 to a viewer component 108 to view medical image data accessed via the platform orchestration server 116 and to employ the various features and functionalities of the viewer component 108.

In various embodiments, the search result user interface can provide selectable information identifying the exams, series and/or individual images that satisfy the search results that can be interacted with to perform various actions. In particular, as described in greater detail infra with reference to 8A-17D, the platform orchestration server 116 can provide various interactive features and functionalities in response to selection of an entry in the search results information, including functions related to viewing the image data using a viewer component 108 and associated image tools 112, editing the image data, editing metadata tags associated with the image data (e.g., adding, removing and/or editing), rating and reviewing the image data, sharing the image data, pushing the image data to desired image storage endpoint, adding the image data to a project, adding the image data to a collection, and downloading the image data. The dashboard component 626 can further provide a dashboard user interface that facilitates organizing and accessing these various features and functionalities of the platform orchestration server.

The exchange management component 614 can provide various image data exchange management features of the platform orchestration server 600 that can be accessed and used via the web-based platform. For example, the exchange management component 614 can include upload/download component 616 that can control/manage uploading and downloading data to and from the platform orchestration server 600. In this regard, the upload/download component 616 can allow users to upload medical image data as well as reports, reviews, related studies, and the like for association with the medical image data to the platform orchestration server 600. In some implementations, the uploaded data can be stored by the platform orchestration server via the server storage component 114, and/or in memory 662, associated with user account and/or made accessible to other users via the platform. Additionally, or alternatively, the uploaded data can be pushed to one or more of the image storage endpoints 102. For example, in some embodiments, the upload/download component can allow medical image providers to upload exams, series and/or individual images to the platform orchestration server for storing at one or more of the image storage endpoints 102.

The upload/download component 616 can also provide for downloading medical image data sets from the image storage endpoints 102 onto a user device 126. For example, in some embodiments, the upload/download component 616 can provide for downloading the images included in search results, images included in a user collection, images associated with a group project, and the like. The transfer component 618 can provide for transferring image data accessed via the platform orchestration server 600 from one location to another. For example, the transfer component 618 can provide for selecting an image data set (e.g., including one or more images) stored at first image data storage endpoint and pushing the image data set to one or more second image data storage endpoints. With these embodiments, the transfer component 618 can transfer the image data set based on the received user request.

In some embodiments, the data request component 620 can provide for requesting image data that satisfies defined criteria. In this regard, the data request component 620 can provide a saved search function wherein the search component 606 regularly searches for new image data meeting the defined criteria and returns the new search results. Additionally, or alternatively, the data request component 620 can post or otherwise provide image data requests to image data providers for potentially fulfillment. For example, the data request component 620 can allow a user to generate an image data request that describes the criteria for a requested image data set and the scope of the desired usage (e.g., for AI model development, for research, for marketing, etc.). The data request component 620 can further post the image data request to a content provider forum where content providers can review and respond to the requests. In this regard, the data request component 620 can facilitate connecting customers/project creators with image data content providers that can provide the image data that meets their demands.

The permission component 622 can assign and mange usage permissions/restrictions associated with using medical image data accessed via the platform orchestration server 600. For example, in some embodiments, a content owner/provider can authorize any user to use their medical image data for any purpose. In other implementations, the content owner/provider can place restrictions on usage, including restrictions regarding who can use the image data and the scope of the usage (e.g., for research, product development, marketing, etc.). With these embodiments, the permission component 622 can prevent users from accessing, downloading, transferring, editing, and/or other actions related to usage of medical image data based on any usage restrictions associated with the image data. The permission component 622 can also be used by a content owner/provide to apply/assign usage restrictions to their data sets. In some embodiments, prior to allowing a user to perform an action relative to an image data set (e.g., download, add to a project, annotate, etc.), the permission component 622 can facilitate generating a usage agreement for the action between the content owner the entity requesting to perform the action. For example, the permission component 622 can send a usage request notification to the content owner informing the content owner of the requested usage and the relevant details of the usage request (e.g., user identity, usage scope, etc.). For example, the usage request notification can present a usage agreement with the details of the requested usage. The permission component 622 can further authorize the usage in response to acceptance of the agreement by the content owner and the requestor.

In various embodiments, one or more features and functionalities of the platform orchestration server 600 can be accessed by any user (e.g., search functions). In other embodiments, the account access component 610 can control access to some or all of the features and functionalities of the platform orchestration server 600 based on establishment and authorized usage (e.g., authorized login) of a user account. With these embodiments, the account access component 610 can include an account component 612 that can facilitate establishing user accounts for users with the platform orchestration server 600. For example, the account component 612 can set up a user account with the system and assign the user with a unique account/username that can be accessed using one or more entity verification/authentication mechanism (e.g., username and password and the like). With these embodiments, the account access component 610 can restrict access to some or all of the features and functionalities of the platform orchestration server 600 to registered users in association with authorized usage of their account. The platform orchestration server 600 can apply usage restrictions regarding usage of certain features and functionalities of the system based on individual permissions granted to certain user accounts based on their identity, role, account status, authority, and the like. For example, in some embodiments, the account access component 610 can manage and/or control image data exchange and sharing permissions based on authorizations/restrictions associated with respective user accounts.

The account management component 628 can provide various features and functionalities associated with usage of the web-platform with an established user account, including project creation features, collection features and tracking features. In this regard, the account management component 628 can include project component 630 to facilitate managing and collaborating on projects that involve usage of image data provided by the image storage endpoints 102. For example, the project component 630 can provide a project creation function to enable creation of a project file (or files) for a given set of analytics applied to a respective medical image and metadata. In particular, the project creation component 630 can allow a user to define a project, such as a research project, a product development product, a marketing project and the like. For example, the project creation component 630 can receive information defining the title of the project, the scope of the project, the image data needed or being used for the project, the other users involved in the project, and the like. The project creation component 630 can further generate project groups with the users included in the projects and facilitate collaboration between users on the project. For example, in some embodiments, the project component 630 can allow a user to post a new project and/or otherwise share information identifying the new project to other users. The project component 630 can also allow other users to connect with project creators, invite users to joint a projects and request to join projects. Information identifying the projects a particular user has created/established, as well as information identifying the projects the particular user has joined can be associated with their user account/profile.

The collection component 632 can provide for generating medical image data collections with the medical images provided by the image storage endpoints 102. A medical image data collection can be or correspond to a list medical image exams, series, and/or individual images selected for collection in a group by a user and associated with their user account/profile. In various embodiments, a collection list can include information identifying the medial images included therein that can be interacted with to perform various actions regarding the medical images included in the collection (e.g., viewed, downloaded, shared, reviewed, rated, edited, added to a project, pushed, assigned a usage agreement, etc.).

The tracking component 634 can track individual user account activity associated with usage of their account and provide historical activity information to the account user regarding their tracked account usage activity. For example, the tracking component 634 can track usage including past searches conducted, past images rated, past projects created, past collections generated, and the like.

The collaboration component 650 can provide variety of features and functionalities of the platform orchestration server 600 that involve user collaboration related to medical image data provided by the image storage endpoints 102. In various embodiments, the collaboration component 650 can include rating/review component 652 to facilitate generating crowed sourced rating and review information for the medical image data. For example, in various embodiments, the rating/review component 652 can provide a rating function that allows a user to provide feedback rating or scoring an exam, series and/or individual image in one or more categories. For instance, the one or more categories can include overall image quality as well as sub-categories pertaining to signal noise, contrast, artifacts, acquisition duration, resolution, pathology and the like. In another example, the one or more categories can include usefulness of data relating to the medical images and metadata. The rating/review component 652 can further generate a rating or score for an exam, series and/or individual image based on the collective received feedback. In various embodiments, feedback received for an exam, series and/or image can be associated therewith in the global data index 118 as additional metadata. Image rating can further be employed as a search and/or filter criterion for finding desired medical images.

The rating/review component 652 can also allow users to provide additional feedback for an exam, series and/or image in the form of a descriptive review (e.g., using free form text). In some embodiments, the rating/review component 652 can provide a mechanism for users to flag or tag images that contain PHI data and request actions related to certain images or image data sets. For example, the rating/review component 652 can provide a mechanism for user to request removal of exams, series, and/or individual images, to request additional information about an exam, series and/or individual image (e.g., regarding capture context, regarding the patient, etc.), to request annotation of the exam, series and/or individual image, and the like. The rating/review component 652 can further post requests pertaining to medical images to a community forum which can then be selected and responded to. Additionally, or alternatively, the rating/review component 652 can post or otherwise provide requests pertaining to medical images to selected user groups, and/or selected users.

The tag component 654 can facilitate applying metadata tags to medical images, removing metadata tags, and editing metadata tags by authorized users and/or by multiple users in a crowd-sourced collaborative manner, directly via the web-platform UI. The tag component 654 can further update the global data index 118 accordingly. In this regard, the tag component 654 can provide a crowd source mechanism for enriching the medical image dataset provided by the image storage endpoints. In various embodiments, the tag component 654 can facilitate applying metadata tags describing essentially any user identified attribute of an exam, series and/or individual image. The tag component 654 can further format the metadata tags according to a defined format (e.g., the DICOM format or the like). In some implementations, the tag component 654 can receive free form text describing an attribute of a medical exam, series, or image for application thereto as a metadata tag and convert the free form text into a DICOM format in association with generating and applying the metadata tag thereto.

The annotation component 656 can similarly provide for applying annotations to medical exams, series and/or individual images by multiple users. For example, the annotations can include image markups and/or text descriptions applied to a medical image regarding the pathology of medical condition depicted in the medical image, measurement data, segmentation masks, disease region markers and the like. In some embodiments, the annotation component 656 can generate an annotation file for an exam, series, or image that can be added to by multiple users based on their applied annotation. The annotation file can be associated with the exam, series or image and stored by the server storage component 114, in one or more of the image storage endpoints 102 and/or another suitable data storage element accessible by the platform orchestration server 116.

The sharing component 658 can provide a data sharing function that allows users to share information with one another regarding medical image data. For example, the sharing component 658 can allow a user to share individual images, share search results, share image data collections, share projects, share feedback, and the like. The sharing component 658 can provide various avenues for sharing data with other users. In some embodiments, the sharing component 658 can allow users to select individual users and/or user groups to share data with. The sharing component 658 can further post the shared data to the accounts of the selected users/user groups in response to a request to share the data.

The social activity component 660 can track information regarding all user activity in association with usage of the web-based platform and generate tailored data feeds for individual users regarding relevant activity based on their preferences. For example, the social activity component 660 can allow users to identify other users they would like to follow, image data that are interested in, projects they are interested in, and the like. For instance, one user may identify other scientists, researchers, AI model developers, etc., that are users of the platform that the user is interested in receiving information regarding their projects created and/or managed using the project component 630. The social activity component 660 can further track social activity information relevant to a user's interests and provide the social activity information to the user via their account in the form of a social activity feed or the like.

The image data processing component 636 can provide various automated and/or semi-automated functions for processing the medical image data stored at the image storage endpoints 102 and/or the server storage component 114. To facilitate this end, the image data processing component 636 can include attribute identification component 636, automated annotation component 640, similarity analysis component, fingerprint component 646 and data formatting component.

In various embodiments, the attribute identification component 636 can employ one or more image processing algorithms or models to analyze medical images stored at the image storage endpoints 102 and automatically determine or infer attributes of the images. For example, the attributes can include image features related to image quality, pixel density, dimensions, orientation, signal noise, contrast, artifacts present as well as attributes regarding anatomical features included in the images, pathology, and the like. In some embodiments, the one or more image processing algorithms or models can include a feature extraction model configured to identify and extract image features from the images. In another example, the one or more image processing algorithms or models can include classification models, object recognition models, segmentation models, and the like. For example, the one or more algorism/models can include models configured to perform a disease/condition classification task, disease region segmentation task, an organ segmentation task, a disease quantification task, a disease/condition staging task, a risk prediction, temporal analysis, anomaly detection, anatomical feature characterization, medical image reconstruction, and the like. The image processing model can employ various types of AI/ML algorithms, including (but not limited to): deep learning models, neural network models, deep neural network models (DNNs), convolutional neural network models (CNNs), generative adversarial neural network models (GANs) and the like.

In some embodiments, attributes determined and/or inferred by the attribute identification component 638 can be associated with the image as metadata in the global data index. In this regard, the attribute identification component 638 can provide for automatically identifying and applying metadata tags to images the can be accessed by the platform orchestration server. Additionally, or alternatively, the automated annotation component 640 can associate one or more of the determined or inferred attributes with the image data as annotation data in a separate annotation file. In some embodiments, the project component 630 can further provide for requesting the image data processing component 636 to perform one or more image processing functions on an individual image or collection of images at a user's request.

The similarity analysis component 642 can compare exams, series and individual images stored in the image storage endpoints using various similarity scoring metrics and the attributes associated therewith. The similarity analysis component 642 can further identify similar exams, series and/or individual images based on the similarity scoring metrics. In some embodiments, the similarity analysis component 642 can group similar exams, series and/or individual images and generate collections of similar exams, series and/or individual images. Information grouping similar exams, series, and/or individual images can further be included in the global data index 118.

In some embodiments, the platform orchestration server 600 can further provide functions for finding comparing images and/or finding similar images in response to user requests. For example, the search component 606 can provide a similar image search function wherein a user can select an exam, series or image and request to find other similar exams, series or images. The search component 606 can further employ the similarity analysis component 642 to facilitate finding the similar image data based on the attributes associated with the selected image data. The similarity analysis component 642 can also provide a similar pathology finder function wherein a user can upload an image with a pathology or artifacts and request to find similar images with similar pathologies or artifacts. This feature can be used by clinicians to facilitate diagnosing and/or quantifying pathological features and artifacts that they have not encountered before and/or that are otherwise unusual.

The similarity analysis component 642 can further generate similarity comparison reports for two or more images/image data sets that evaluates the similarities and/or differences between the images/image data sets based using one or more similarity scoring metrics and the attributes associated therewith. The similarity analysis component 642 can also find duplicate images/image data sets stored in the image storage endpoints.

The fingerprint component 646 can be configured to generate unique fingerprints for exams, series, and/or individual images that can be used by the system to identify the exams, series and/or images in an anonymized manner. In some embodiments, the fingerprint component 646 can employ a feature extraction network to extract unique features for an image or image data set and generate the fingerprint using the extracted features/feature vectors. Information defining the fingerprint generated for an exam, series or image can further be associated with the image data in the global data index 118. Fingerprint data can also be used by the similarity analysis component 642 to identify duplicate images/image data sets.

FIGS. 7-16C provide example user interfaces UIs illustrating the various features and functionalities of the platform orchestration server 600 described above. The UIs presented in FIGS. 7-16C present example UIs that can be generated and presented by the user interface component 624 in association with access and usage of the web platform employed by the platform orchestration server 600 to provide user with access to the various features and functionalities of the platform orchestration server 600 described above. The FIGS. 7-16C are now described with reference to FIG. 6.

Figure 7:
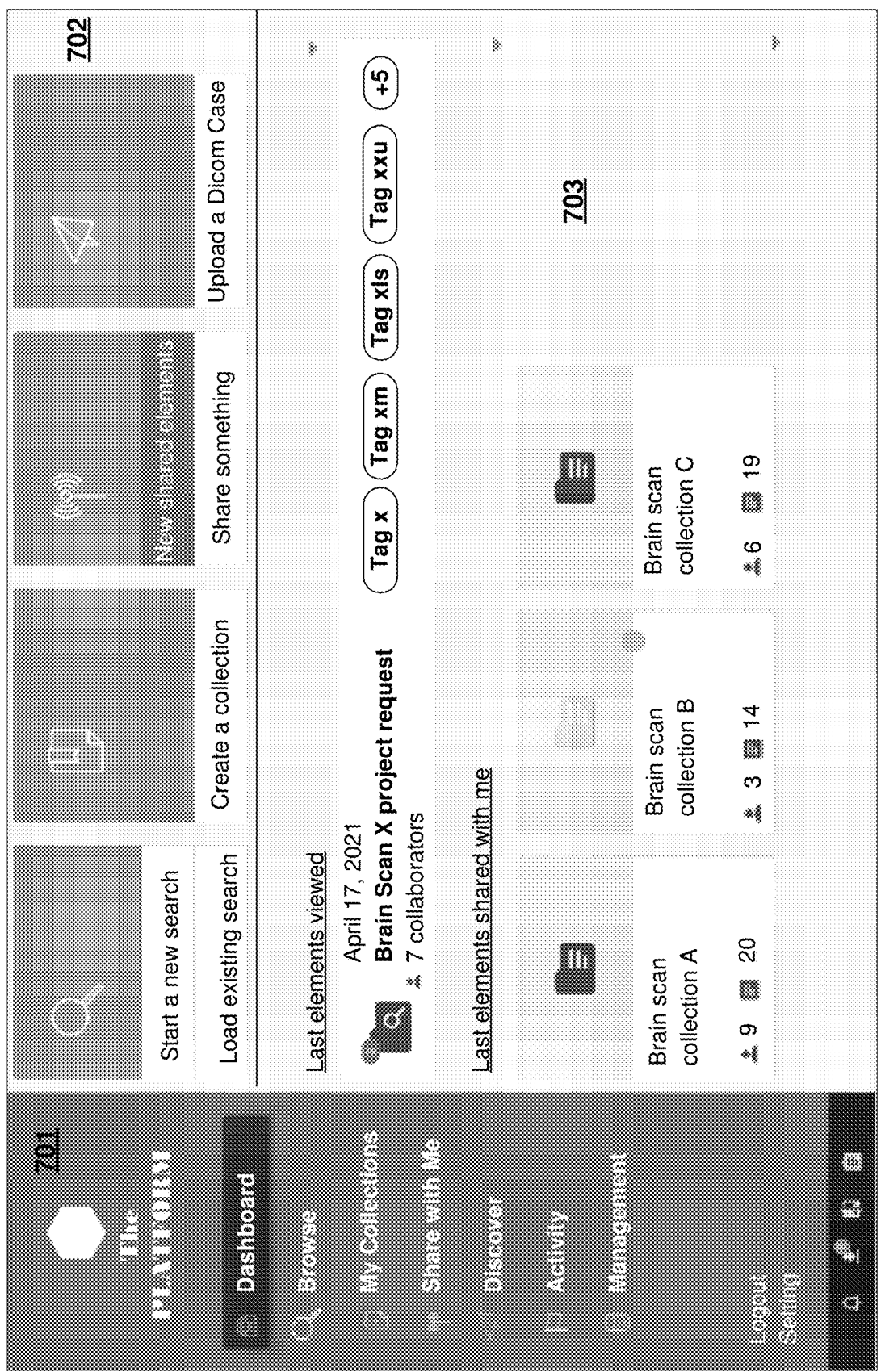
FIG. 7 presents an example dashboard user interface (UI) that facilitates accessing, managing, and sharing anonymized medical image in accordance with one or more embodiments of the disclosed subject matter.

FIG. 7 presents an example dashboard UI 700 that can be generated by the dashboard component 626 to facilitate accessing, managing, and sharing anonymized medical image in accordance with one or more embodiments of the disclosed subject matter. In various embodiments, the dashboard UI 700 can function as a home page for the platform that can be presented to a user upon successful login. In this example implementation, the dashboard UI 700 includes a main side toolbar 701 that includes hyperlinks to the different platform functions and corresponding landing pages/screens, include a "dashboard" page (currently selected), a "Browse" page, a "My Collections" page, a "Share with me" page, a "Discover" page, an "Activity" page, and a "Management" page.

In one or more embodiments, the "Browse" page can provide access to the various search tools and functions provided by the search component 606. The "My Collections" page can present the user with information identifying their previously generated collections and provide tools for generating new collections as facilitated by the collection component 632. The "Share with me" page can present the user with information identifying data (e.g., images, image collections, projects, comments, review, and other data/documents) that have been shared with the user by other users (e.g., as facilitated by the sharing component 658). The "Discover" page can present the user with suggest relevant/recommended information regarding images, image collections, projects and collaborator activity on the platform based on the user preferences. The "Activity" page can present the user with activity information regarding their recent activity on the platform and/or recent activity of other users that the user has become associated with (e.g., as friend, follower, or the like) or has otherwise expressed interest in following their activity. In one or more embodiments, the "Management" page can provide access various additional features and functionalities of the management component, including project creation and management features and functionalities, image data management features and functionalities and the like.

The dashboard UI also include an upper toolbar 702 that provide hyperlinks to additional features and functions of the platform. For example, in the embodiment shown, the upper toolbar 702 includes a search hyperlink for accessing a search page to start a new search or loading an existing search (e.g., as facilitated by the search component 606). The upper toolbar 702 also includes a hyperlink to a collection creation page that provides tools for creating a new collection (e.g., as facilitated by the collection component 632) and a hyperlink to view newly shared elements and/or share elements with others (e.g., as facilitated by the sharing component 658). The upper toolbar 702 also includes a hyperlink to an uploading function via which the user can upload a DICOM case (e.g., any new DICOM data for example) to the platform. Once uploaded, the platform can provide the user with options to view the case, share the case, apply metadata tags and/or annotations to the case, transfer the case to an image storage endpoint 102, request other user feedback on the case, request image processing functions be performed on the case (e.g., by the image processing component 636), request similar medical images, and various additional features and functionalities discussed herein.

The dashboard UI also includes a feed section 703 that provides recent activity information associated with the user account. For example, in the embodiment shown, the feed section 703 provides information regarding the last item viewed by the user and last (e.g., most recent) elements share with the user by other users. In various embodiments, the elements in the feed section 703 can be selectable to open the corresponding element.

Figure 8A:
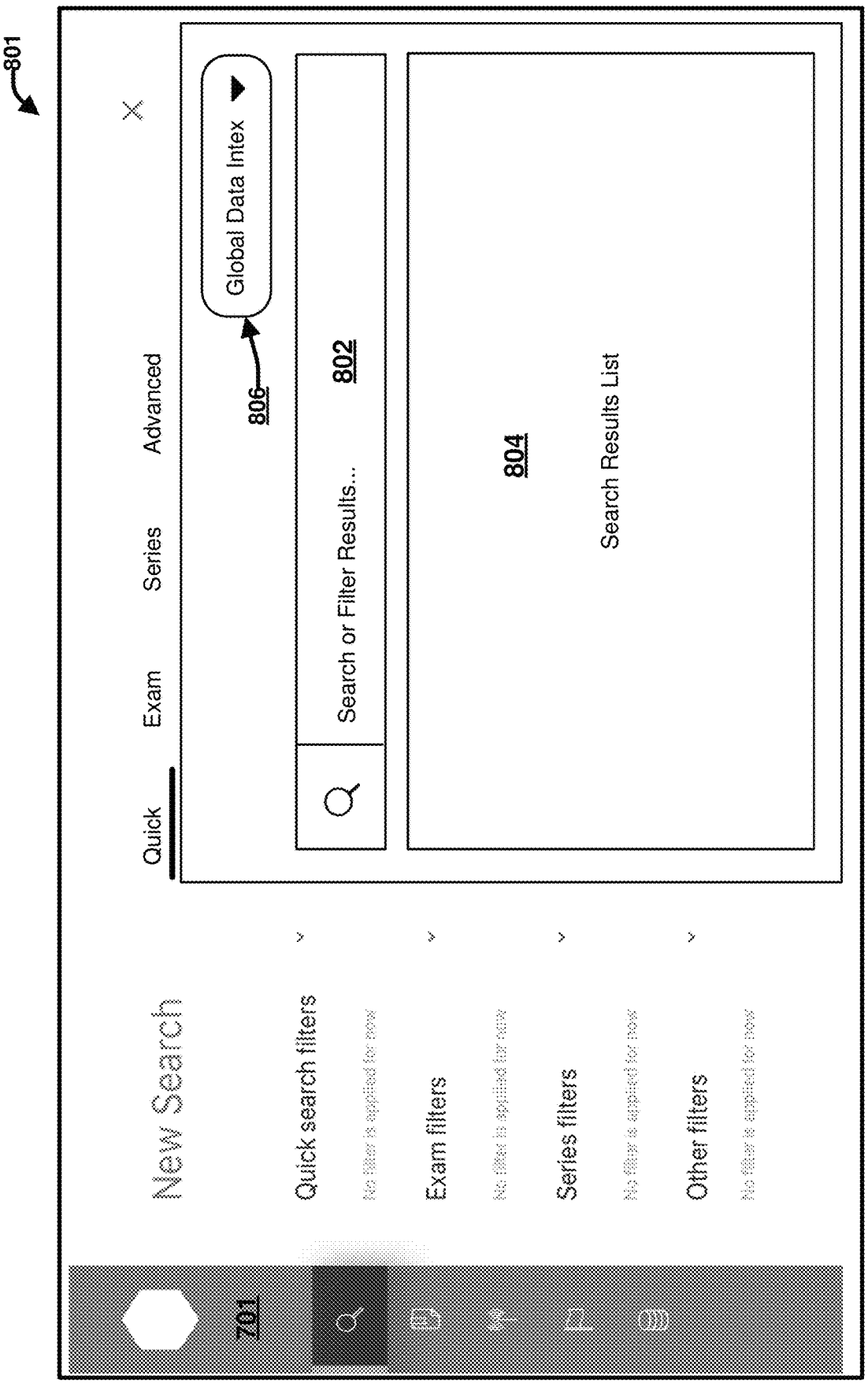

FIGS. 8A-8K present example search function UIs in accordance with one or more embodiments of the disclosed subject matter. FIG. 8A presents one example search UI 801 that can be or correspond to the initial search landing page presented to a user in response to selection of the "Browse" hyperlink from the main side toolbar 701. The search UI provides different search options that can be used to search for a specific type of image data and be presented with a set of results corresponding to the search. These search options include a "Quick" search option, an "Exam" search option, a "Series" search option and an "Advanced" search option.

In the embodiment shown, the "Quick" search option is currently selected. The "Quick" search option can be used to perform a general keyword search or a search using one or more applied keyword search terms and/or selectable pre-defined filters. For example, a user may desire an image of a foot with a hammer toe, and enter a query in the search bar 802 corresponding to such e.g., "foot with hammer toe," and a set of images with a foot with a hammer toe will be presented in the form of a search results list in the results area 804. Filters can be employed to narrow the search (e.g., age of patient, demographic, region of world, particular tow, skin color, infection).

The search UI 801 further allows the user to select the search domain. In particular, the search UI includes a drop-down menu 806 that indicates the current search domain is the entirety of the global data index. In some embodiments, this can be the default domain. In this example, selection of the drop-down menu can present the user with other domain options, such as specific regions, specific databases, specific image storage endpoints, specific categories (e.g., all images, all exams, all series) 102 and the like.

Figure 8B:
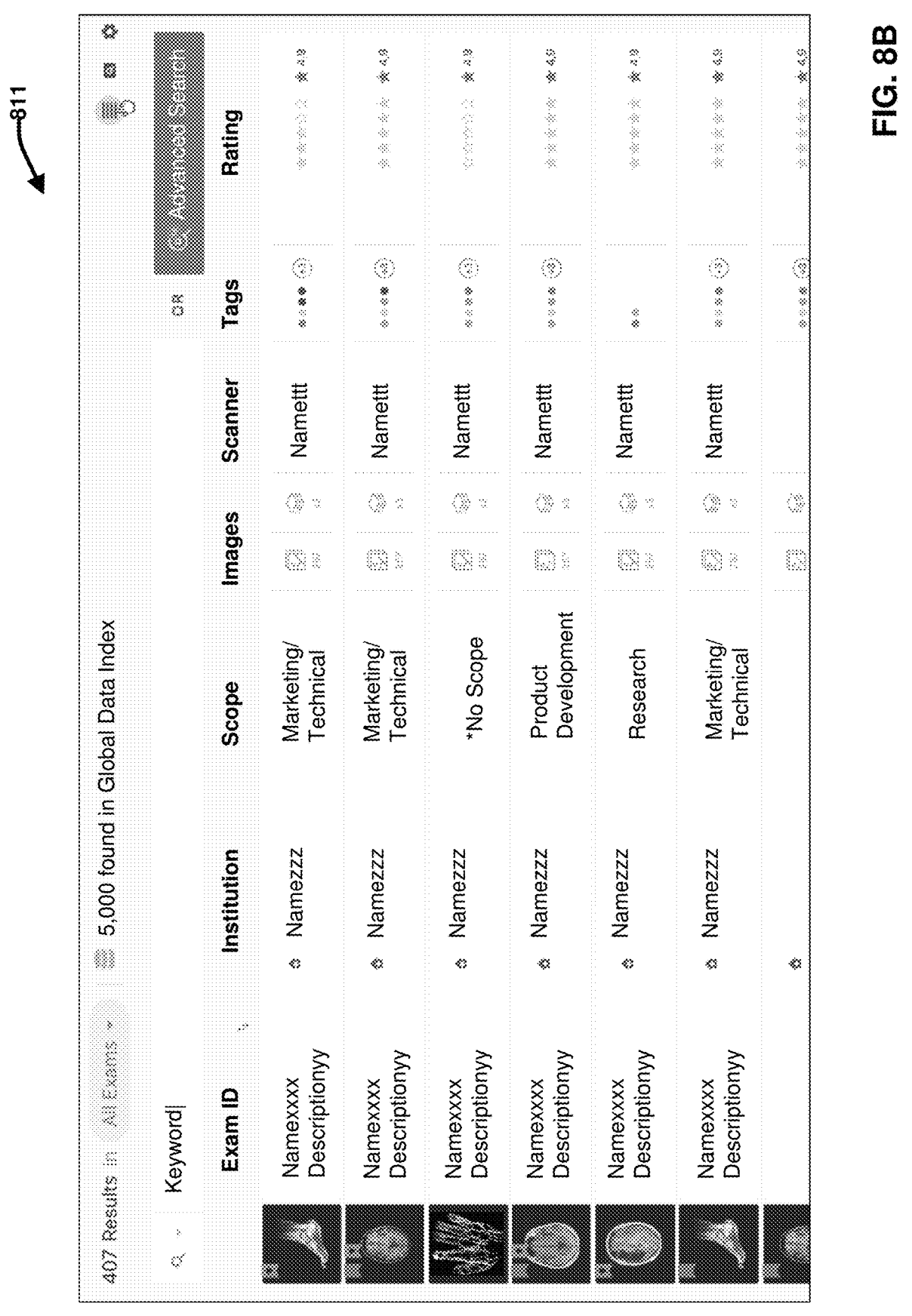

FIG. 8B presents an example search UI 811 that provides search results data generated in response to an exam search using a keyword. It should be appreciated that the various example UI presented herein use terms, values and text descriptions that are merely arbitrary placeholders. The search results data can include a list format of exams found in the selected search domain, which in this case is "All Exams." For example, as indicated at the top of the search UI 811, 407 results were found "All Exams" and 5,000 were found in the global data index. In various embodiments the domain "All Exams" can be or correspond to a restricted domain of all exams associated with a particular organization, all exams associated with a particular region or the like.

The search results data can include high-level information describing the respective datasets which in this example, includes a representative image, the exam ID, the institution where the exam was capture, the scope of usage authorized, information regarding the number of images (e.g., number of series and individual images), the image capture scanner type/manufacture, the number of metadata tags associated therewith, and the average rating for the exam. In various embodiments, the entries in the search results can be selected and interacted with to view additional information about the entry and to perform various actions for the corresponding entry.

FIG. 8C presents an example exam search UI 821 in accordance with one or more embodiments of the disclosed subject matter. The exam search UI 821 provides an example UI that can be presented to the user in response to selection of the "Exam" search option from search UI 801. This exam search UI 821 provides an example UI that can be used to apply detailed search criteria for finding specific exams. In the embodiment shown, the detailed search criteria are divided into two categories, including exam details 808 and anatomy 810. As shown in FIG. 8C, some example exam details search criteria can include (but is not limited to): tag name, modality, patient name (e.g., which can be anonymized), patient ID, exam ID, exam description (can include dropdown list items selectable), exam date, institution, scanner name, manufacturer, operator name, data collection agreement usage (e.g., this is under marketing agreement, a technical agreement, etc.), rating average, patient body mass index (BMI), patient weight, and patient age. The exam details criteria also include an option to restrict the search to exams with clinical stories. In this regard, some exams can be associated with clinical story information that provides additional details and context of the exam. In some embodiments, the platform can provide for receiving user input attaching a clinical story to an exam as a function supported by the rating/review component 652. The anatomy 810 category can provide filters for anatomy parts and can include a drop-down list of anatomy parts and sub-parts for selection.

FIG. 8D presents an example series search UI 831 in accordance with one or more embodiments of the disclosed subject matter. The series search UI 831 provides an example UI that can be presented to the user in response to selection of the "Series" search option from search UI 801. This series search UI 831 provides an example UI that can be used to apply detailed search criteria for finding specific series. In the embodiment shown, the detailed search criteria are divided into four categories, including a general category 814, a geometry category 816, a timing category 818, and an acceleration category 820. The categories and the search filters associated with each of these categories can vary based on series type, which in this example include CT, MR, PET and X-Ray. In the embodiment shown, the MR series type is selected. The series search UI 831 also provides an upper toolbar 812 with additional search filters including series description, average rating, software version and tag name. In various embodiments, exams and individual images can also be filtered or searched by rating (e.g. find me exams, series and/or images with a rating of 4 stars or higher).

Figure 8E:

FIG. 8E presents an example advanced search UI 841 in accordance with one or more embodiments of the disclosed subject matter. The advanced search UI 841 provides an example UI that can be presented to the user in response to selection of the "Advanced" search option from search UI 801 and/or search results UI 811. This advanced search UI 841 provides an example UI that can be used to apply detailed search criteria for finding specific exams, series and/or individual images by building an interactive query. In this regard, the advanced search UI 841 provides an interactive search query building tool via which the user can add one or more search group. Within each search group, the user can select and add numerous filters with specific operators and values. This advanced search options results in building an elastic search query.

Figure 8F:
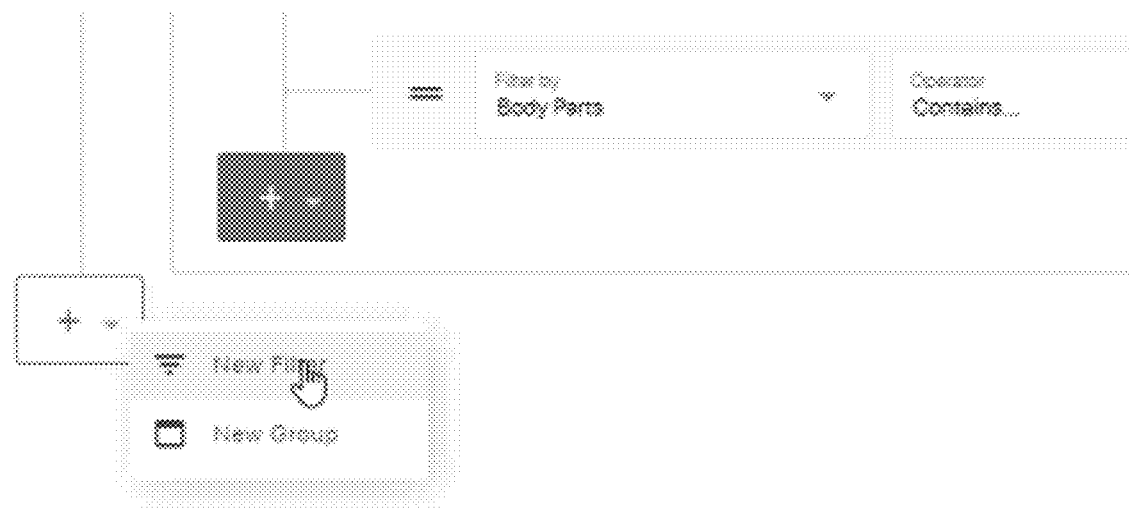
Figure 8G:
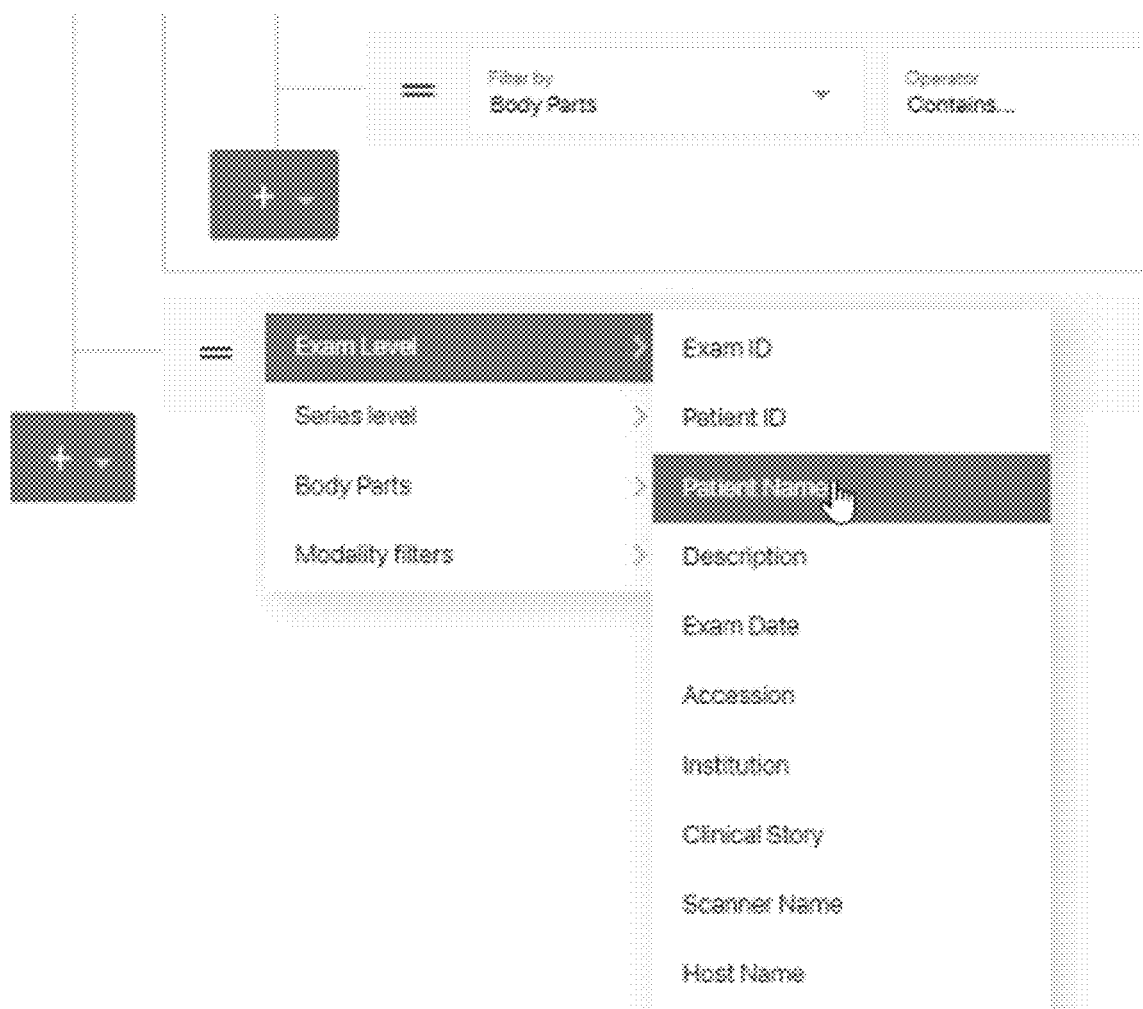
Figure 8H:
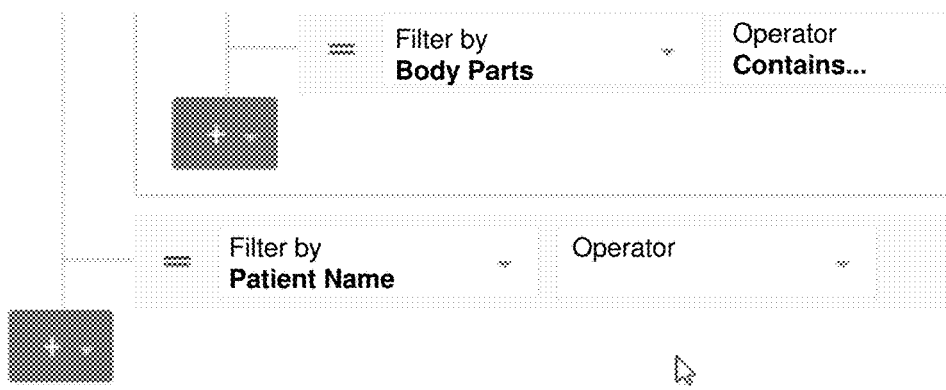
Figure 8I:
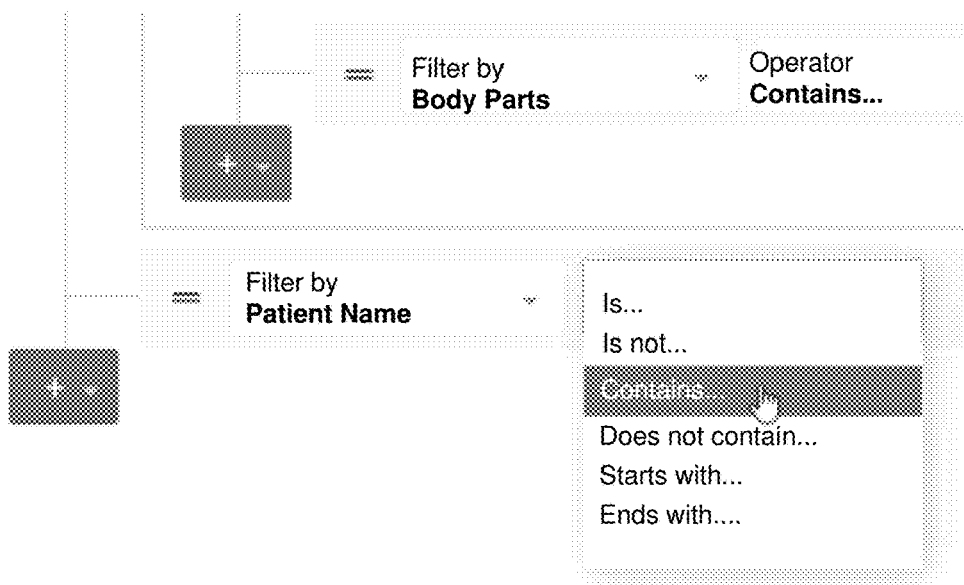
Figure 8J:
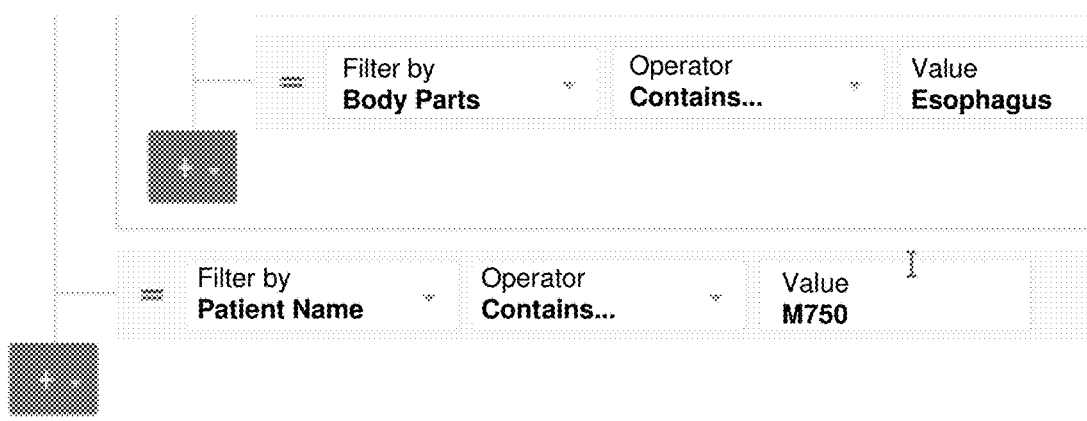
Figure 8K:
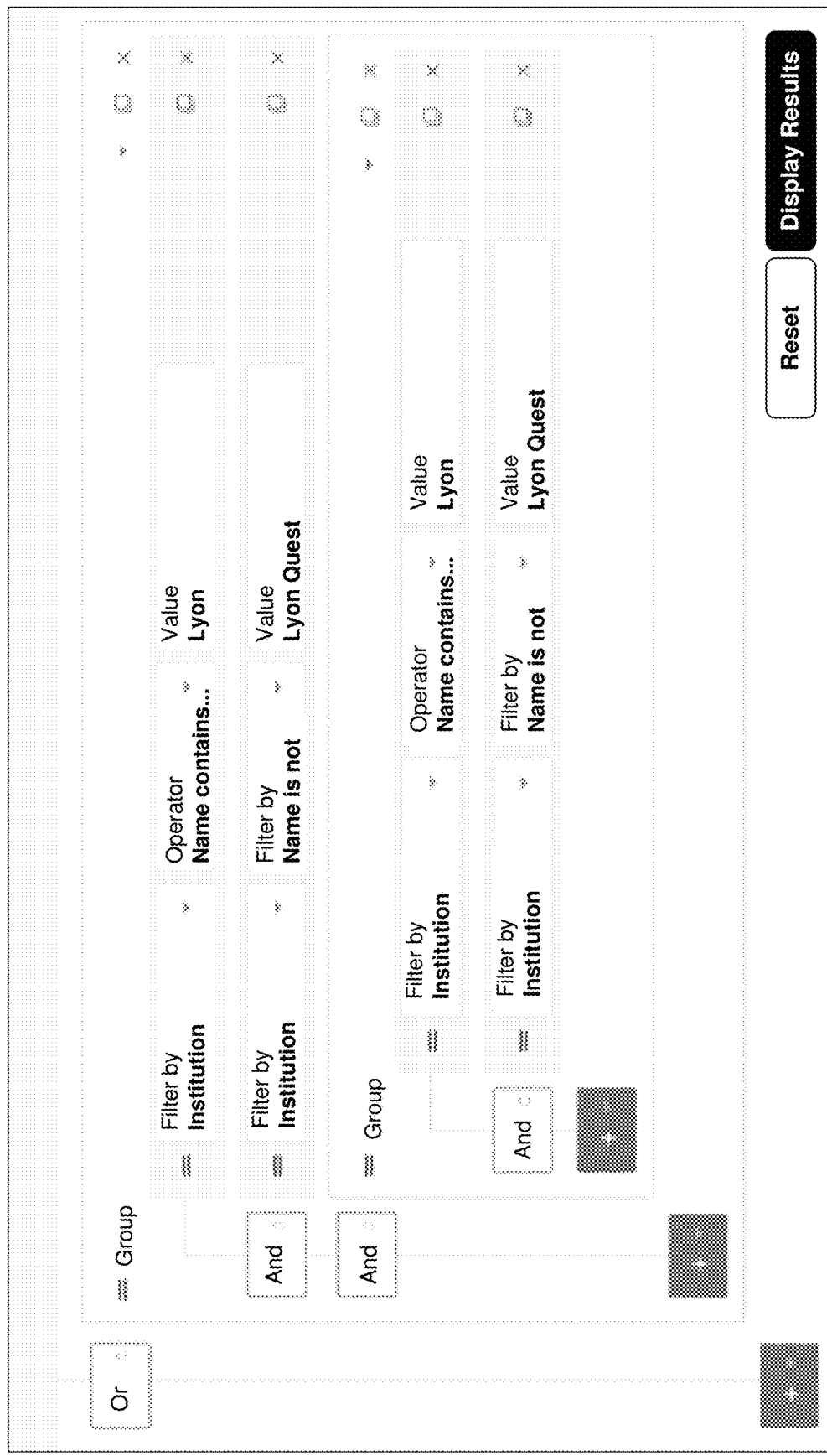

FIGS. 8F-8J demonstrate building an advanced search query using the advance search UI 841. FIG. 8F presents an enlarged view of region 822 of the advanced search UI 841 in association with selecting a new filter or group. FIG. 8G presents different selectable filter criteria that can be presented and applied in association selection of the new filter options shown in FIG. 8F. In this example, the user has selected the filters of patient name for a search at the exam level. FIG. 8H presents the updated advanced search UI 841 in response to selection of the patient name filter option shown in FIG. 8G. FIG. 8I presents a drop-down list of operators that can be applied in response to selection of the operator field in FIG. 8H. FIG. 8J presents the updated advanced search UI 841 in response to selection of the operator "contains" from the operator filed in FIG. 8I and further selection of the value M750 in the value field. FIG. 8K presents another example advanced search UI 851 that was built using the techniques described above.

Figure 9A:

FIGS. 9A-9C provide example search result UIs in accordance with one or more embodiments of the disclosed subject matter. FIG. 9A presents another view of search result UI 811 in association with interaction with one of the exam results referenced herein as the "hand example". In the embodiment shown, interaction with the exam result (e.g., via hovering over, right clicking, etc.), can result in presentation of a preview window 902 for the exam that provides a preview of additional relevant information for the exam. FIG. 9B presents an enlarged view of the preview window 902. In this example, the preview window provides information identifying the exam ID, the scanner name, the exam ID number, the exam date, the exam location (e.g., that is the image storage endpoint 102 where it is located), the scope of usage authorized, the name (e.g., username) of the entity that provided the exam, and the accession number. The preview window 902 also provides a scrollable list of the series included in the exam, with information regarding the number of images in each series and the number of ratings applied. The preview window 902 also provides information indicating the average rating of the exam (which in this example is 4.9 out of 5 stars), and the number of reviewers (which in this example is 347). In the embodiment shown, the user can select the rating star icon to rate the exam. The preview window 902 also include a link to open the exam.

FIG. 9C presents an example exam UI 901 that can be generated and presented in response to selection and opening of an exam. For example, in various embodiments, the exam UI 901 can be presented in response to selection of the open exam link from the preview window 902. The example exam UI provides a series tab for viewing series information for the exam, an exam feed tab for viewing and/or contributing to an exam feed information for the exam, and a clinical story tab for viewing and/or providing a clinical story for the exam. In the embodiment shown, the series tab is selected.

FIGS. 10A-10F present example medical image data viewer UIs in accordance with one or more embodiments of the disclosed subject matter. In various embodiments, example medical image data viewer UIs can be generated and provided by a viewer component 108 accessed via the platform in response to a request to view medical image data. In this regard, the user interface component 624 can connect to a viewer component 108 to access the various imaging tools 112 to facilitate loading and previewing medical image data accessed via the platform. The medical image view UIs provide the user with access to a preview of the medical image as well as the metadata associated therewith.

Figure 10A:
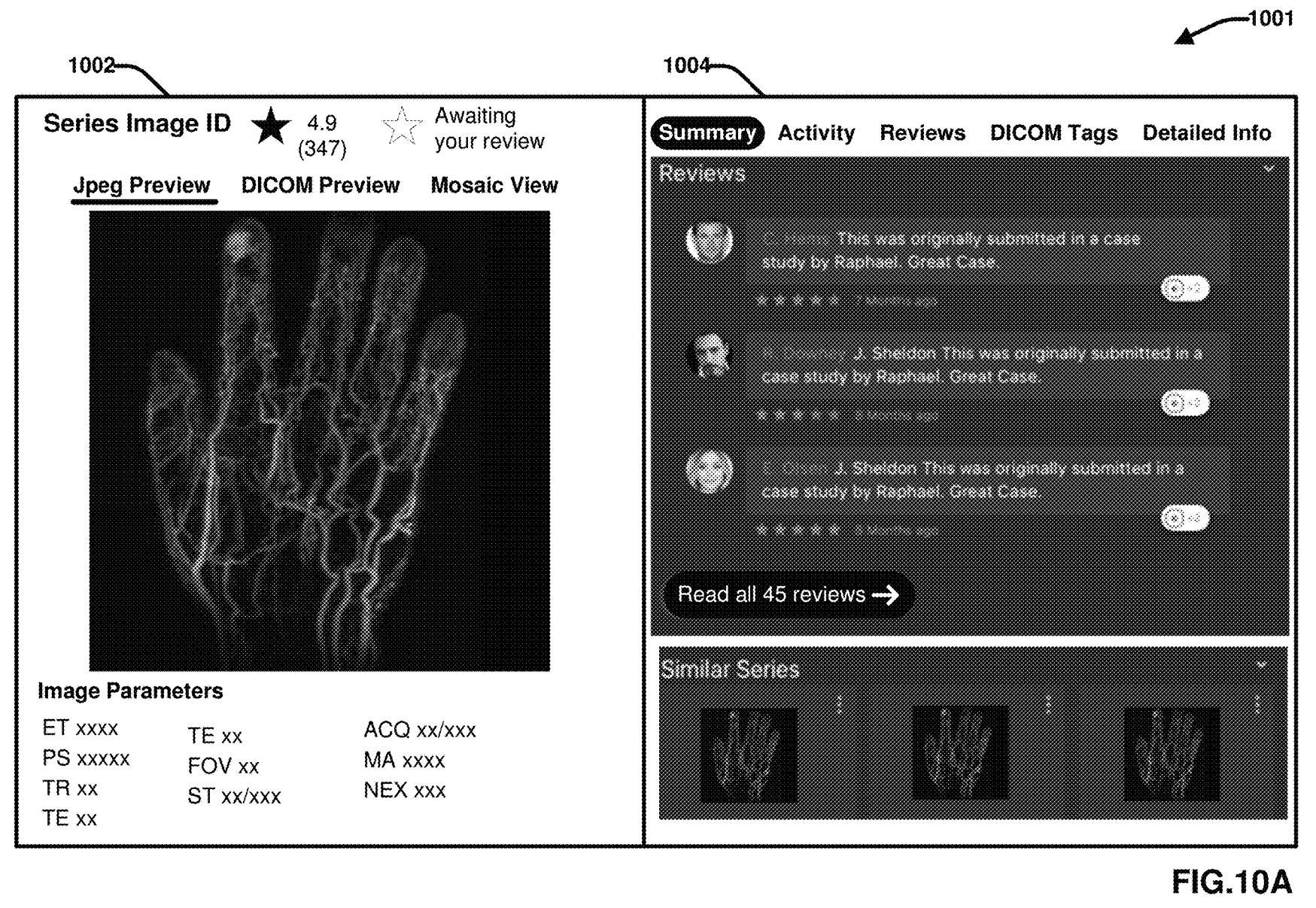

FIG. 10A presents an example viewer UI 1001 that can be generated and presented in response to selection of a particular series for viewing/previewing. For example, in one example implementation, the view UI 1001 can be generated in response to selection of the hand example series from the example exam UI 901 in association with a request to view/preview the series. The viewer UI 1001 includes a preview section 1002 via which a preview of the series image data is presented. In various embodiments, the preview can present a Jpeg image for the series initially.

Figure 10B:
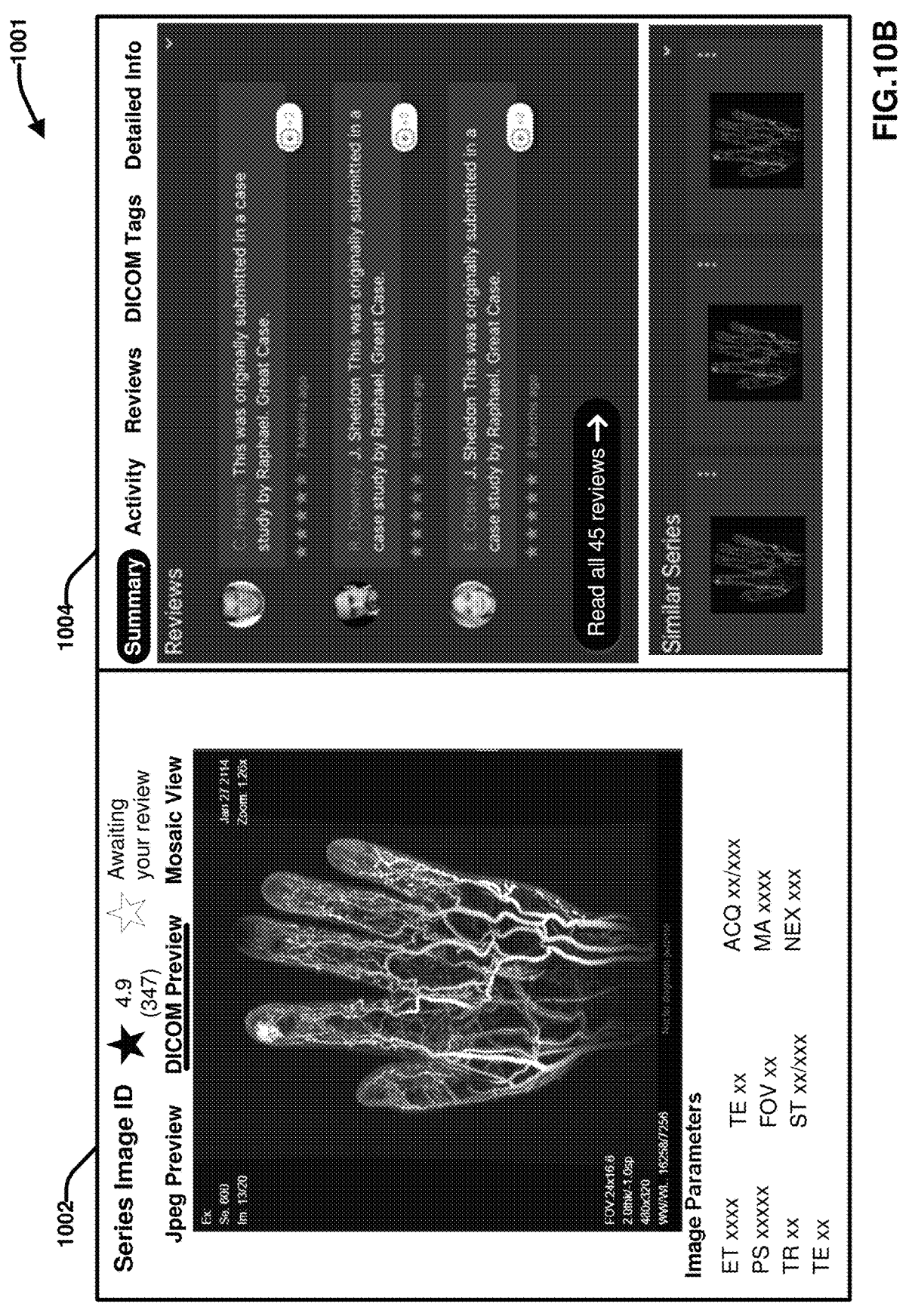

For example, FIG. 10B presents the viewer UI 1001 with the DICOM preview option selected. In various embodiments, selection of the DICOM preview option results in accessing the actual DICOM data at its storage location (e.g., one or more of the image data endpoints 102) and loading the DICOM data by the view application (e.g., the view component 108). In some implementations, the DICOM image can further be interacted with using various imaging tools, such as zooming tools, orientation changing tools, annotation tools and the like.

The viewer UI 1001 further includes an information section 1004 with various tabs that can be selected corresponding to different information categories, including a summary tab, an activity tab, a reviews tab, a DICOM tags tab and a detailed information tab. In the embodiment shown in FIGS. 10A and 10B, the summary tab is selected. The summary tab can provide a summary of various information related to the displayed series image. In this example, the summary section provides a summary of recent user reviews, and similar series information identifying similar series to the selected series.

Figure 10C:
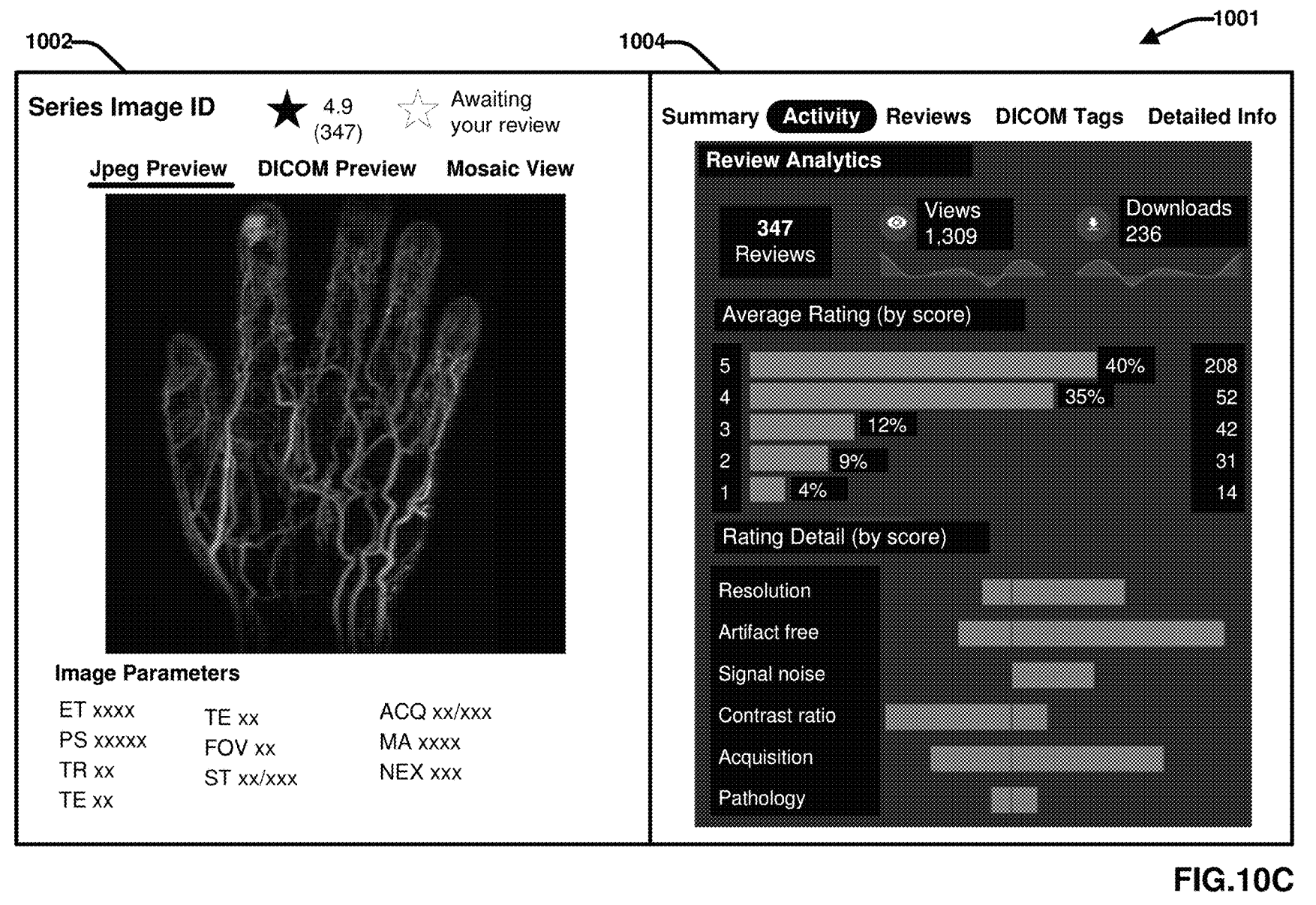

FIG. 10C presents another view of the viewer UI 1001 with the activity tab selected. In this example, the activity tab can provide activity information (e.g., generated by the social activity component 660) regarding aggregated user interaction with the series. For example, the activity information identifies the number of reviews, the number of views, the number of downloads, the average rating broken down by score, and detailed rating information in specific categories.

Figure 10D:
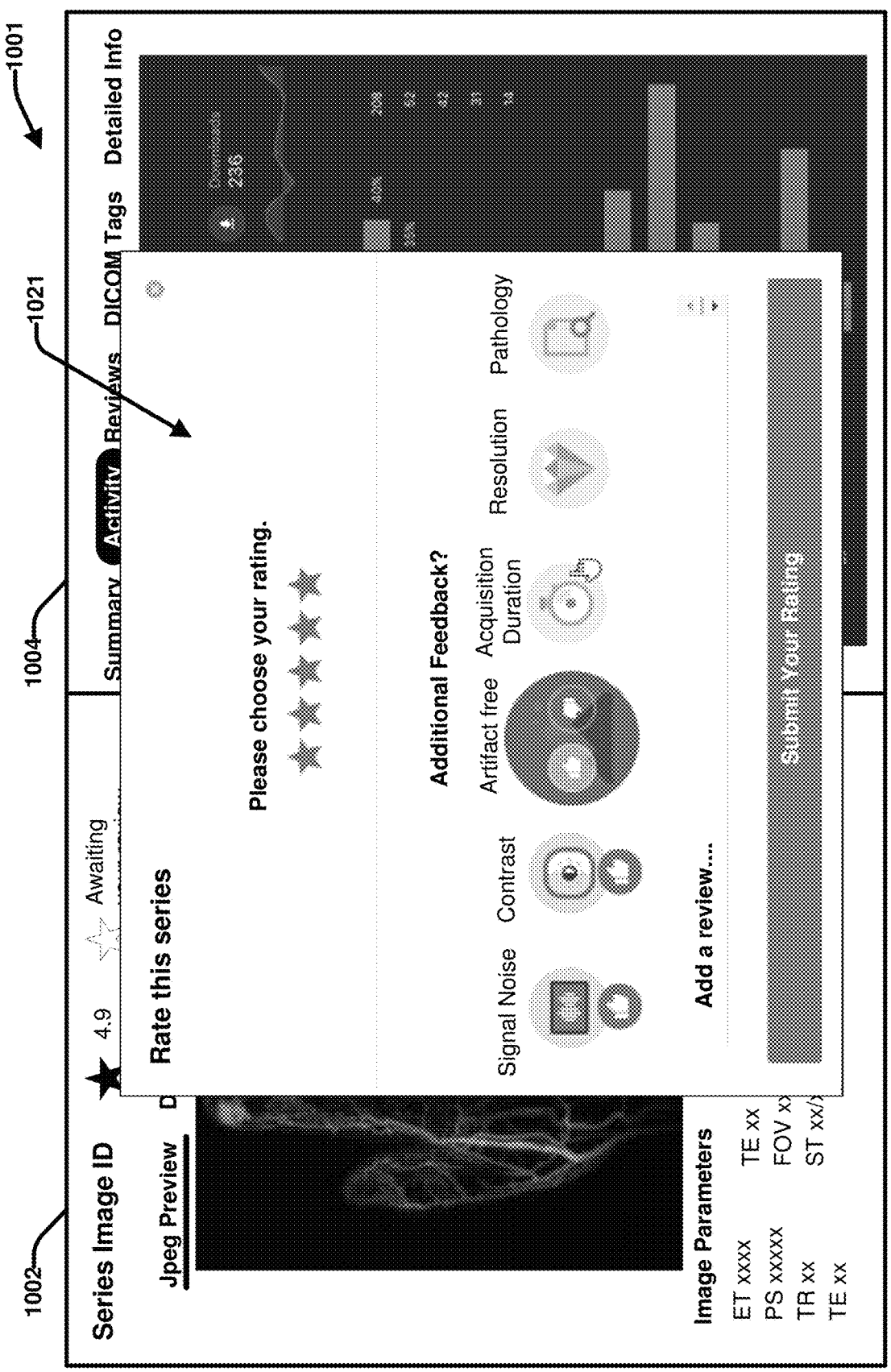

FIG. 10D presents a pop-up window 1021 that provides for receiving user feedback rating the series. In various embodiments, the pop-up window 1021 can be generated and presented in response to selection of the "awaiting review" star displayed in the preview section 1002. As shown in pop-up window 1021, the system provides interactive tools via which the user can rate the series on a five-star level, as well as provide feedback in individual image categories.

Figure 10E:

FIG. 10E presents another view of the viewer UI 1001 with the DICOM tags tab selected. In this example, the DICOM tags tab presents a scrollable list of the DICOM tags applied to the series. The DICOM tags tab further provides a search feature via which the user can search the metadata for specific tags.

FIG. 10F presents another view of the viewer UI 1001 with the detailed information tab selected. In this example, the detailed information tab provides series level details, MR data and information identifying the series location where the series is stored. In this example, the series is stored at three different image storage endpoints.

FIGS. 11A-11D present example interactive features the web platform in with one or more embodiments of the disclosed subject matter.

Figure 11A:
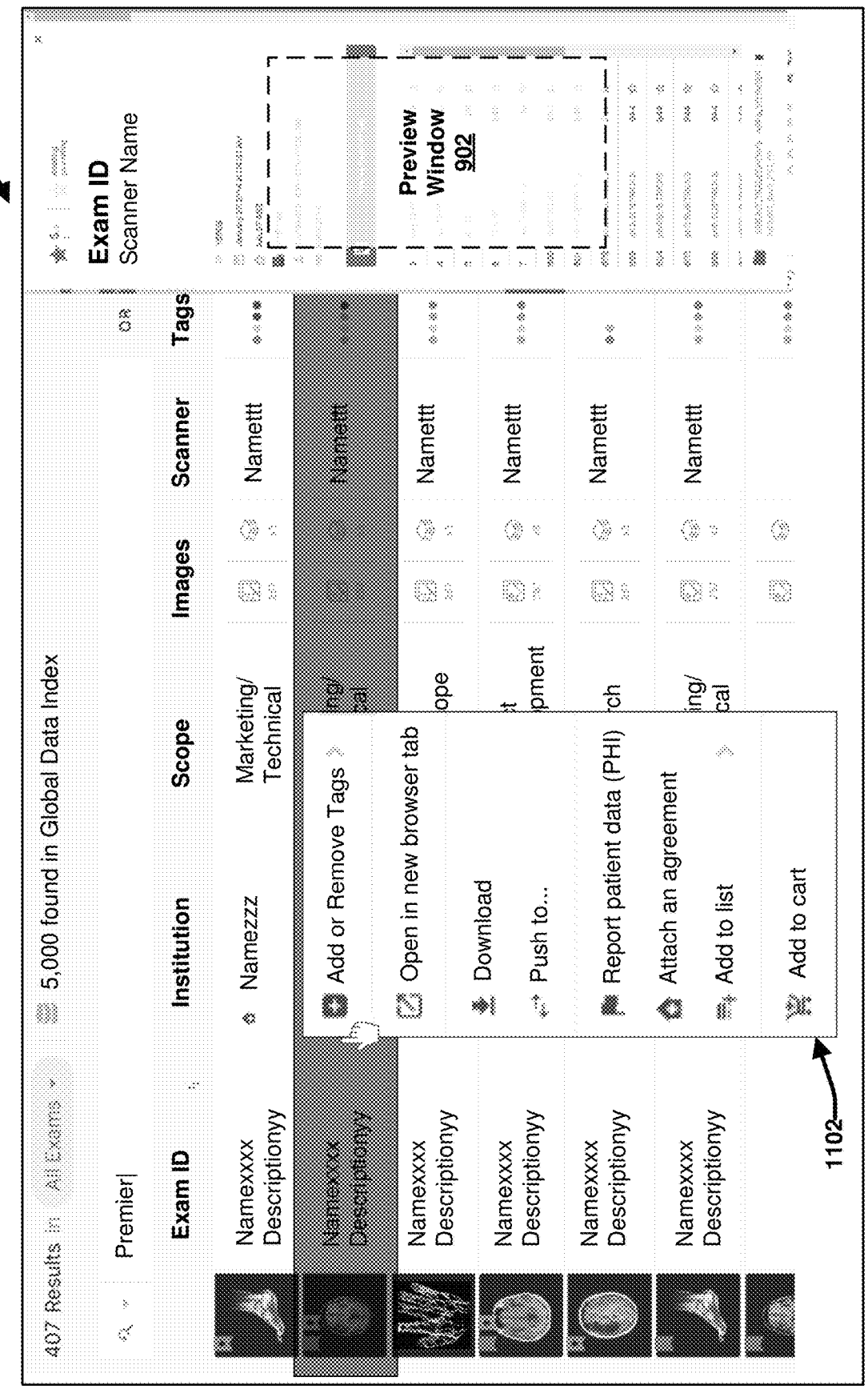
FIGS. 11A-11D present example interactive features the web platform in with one or more embodiments of the disclosed subject matter.

FIG. 11A presents another view of search result UI 811 in association with interaction with one of the exam results. In the embodiment shown, in addition to presentation of the preview window 902, interaction with the exam result (e.g., via hovering over, right clicking, etc.), can result in presentation of an action window 1102 for the exam that provides various actions that can be selected and performed for the exam. In this example, the actions include adding or removing tags, opening the exam in a new browser tab, downloading the exam, pushing the exam to an image data endpoint, reporting PHI, attaching an agreement (e.g., a scope usage agreement), adding the exam to a list (e.g., a collection list, a project list, or the like), and adding the exam to a cart (e.g., that can correspond to saving the exam for downloading in the future).

Figure 11B:
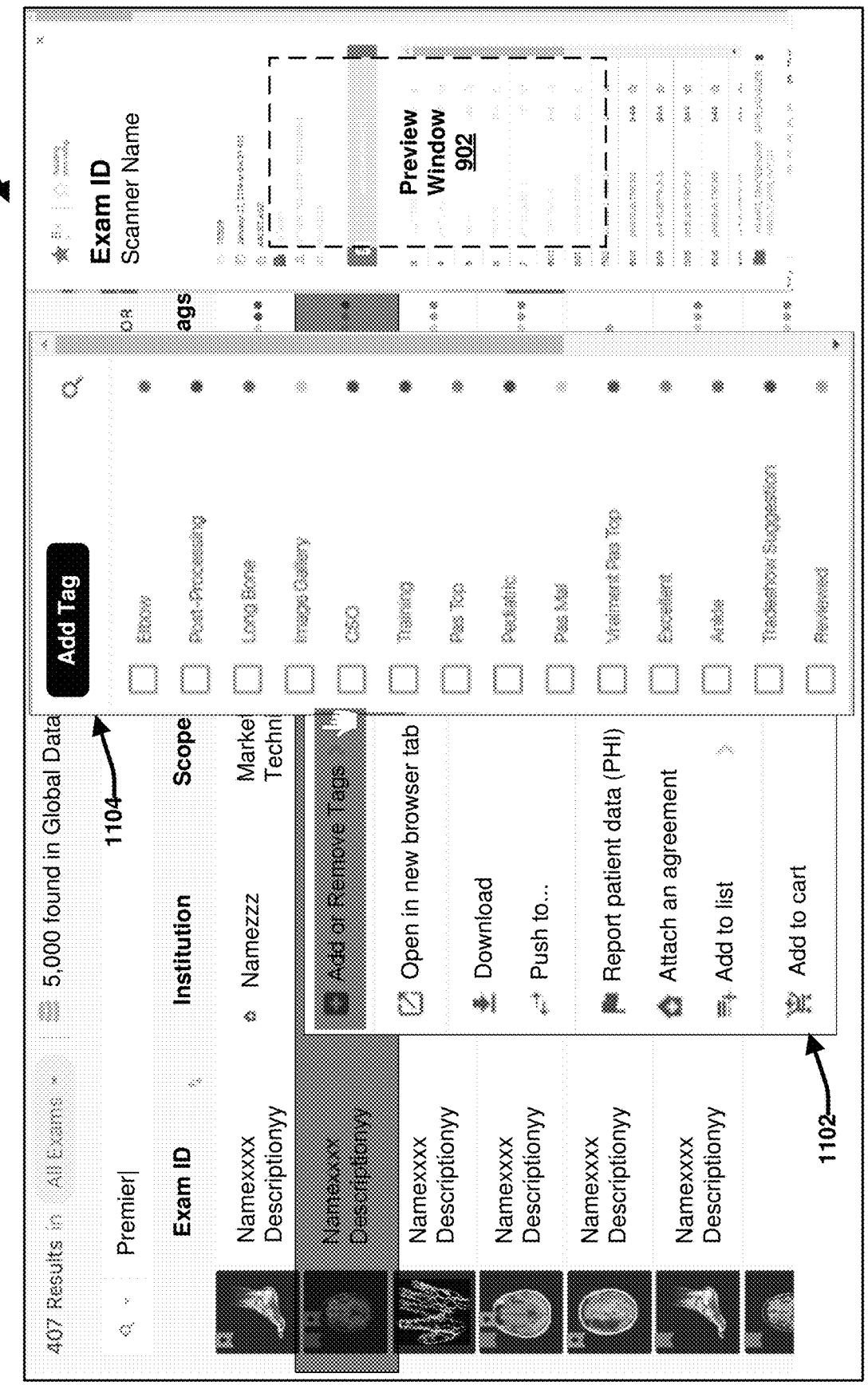

FIG. 11B presents another view of the search result UI 811 in response to selection of the add or remove tags action from the action window 1102. In this example, selection of the add or removes tags action can result in presentation of a tag window 1104 with selectable tag options with predefined tags that can be selected and added to the exam directly from the search result UI 811.

Figure 11C:
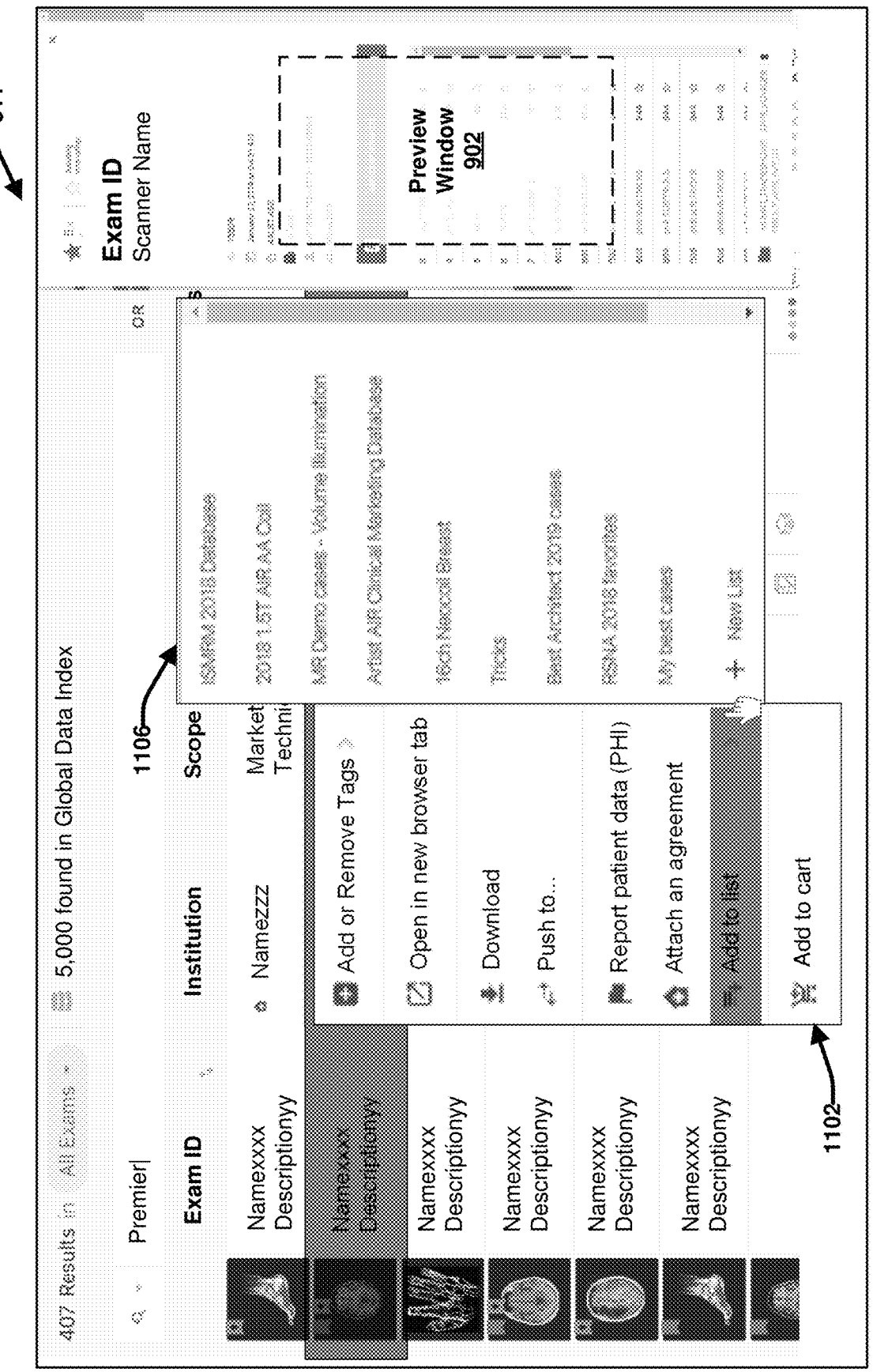

FIG. 11C presents another view of the search result UI 811 in response to selection of the add to list action from the action window 1102. In this example, selection of the add to list action can result in presentation of list window 1106 with selectable list options with previously created lists that be selected for adding the exam to. For example, the previously created lists can include projects that the user is associated with, lists that the user has previously created, and the like. The list window 1106 also provides an option to create a new list for adding the exam to.

Figure 11D:
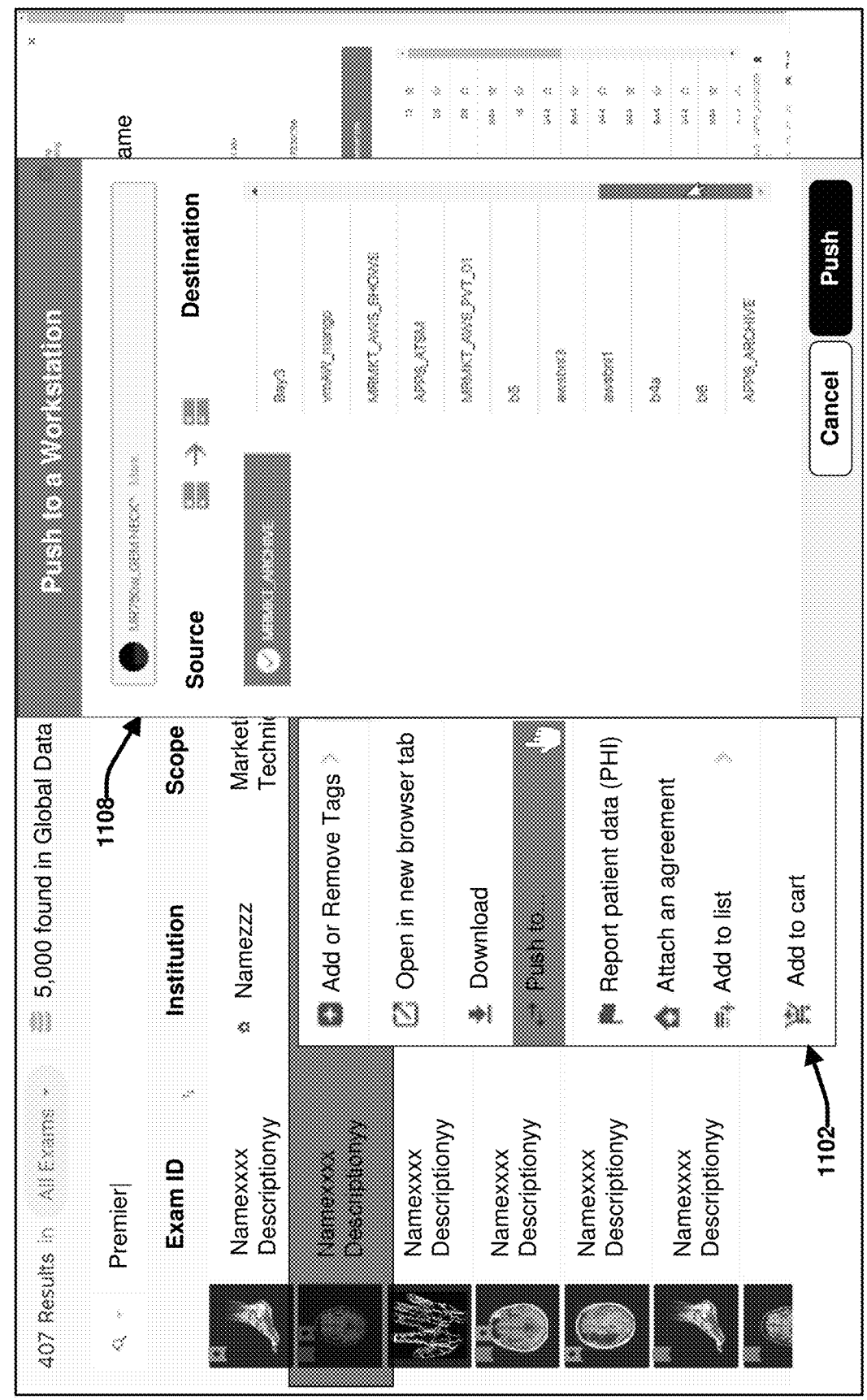

FIG. 11D presents another view of the search result UI 811 in response to selection of the push to' action from the action window 1102. In this example, selection of the push to' action can result in presentation of push to workstation window 1108. The push to workstation window 1108 can provide a transfer function via which the user can select a destination workstation (or another image storage endpoint) via which the user can transfer the exam directly from the search result UI 811. In this example, the workstation window provides the current source of the exam and a scrollable list of destination options for selection. This feature can be used by AI developers for example to transfer an exam directly to an AI development workstation (e.g., via the transfer component 618).

FIG. 12 presents an example exam feed UI 1200 in accordance with one or more embodiments of the disclosed subject matter. Exam feed UI 1200 provides one example of an exam feed that can be generated by the social activity component 660. In this example, the exam feed provides a scrollable list of other users' interaction/activity with the exam.

Figure 13:
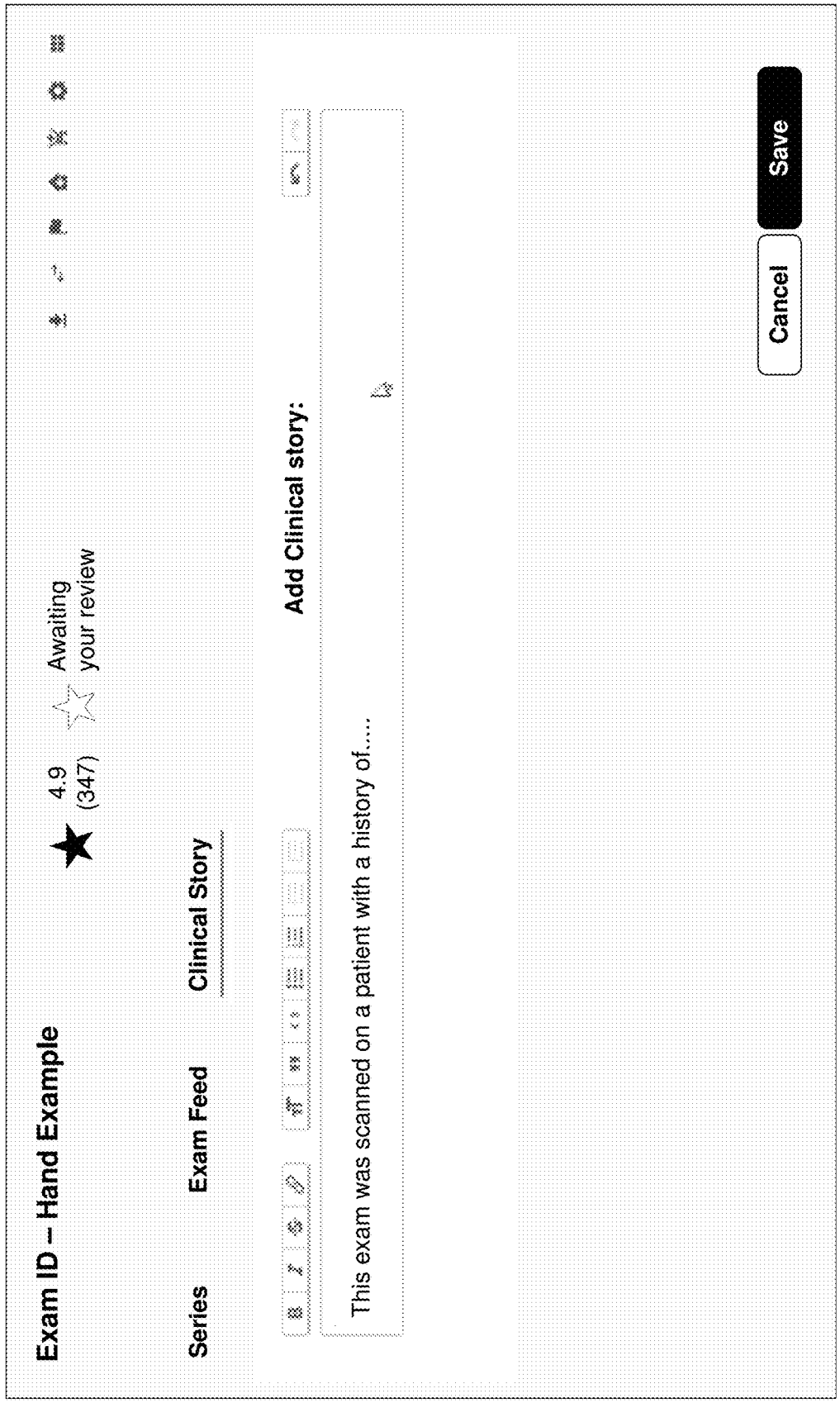
FIG. 13 presents an example clinical story UI in accordance with one or more embodiments of the disclosed subject matter.

FIG. 13 presents an example clinical story UI 1300 in accordance with one or more embodiments of the disclosed subject matter. In this example, a user is currently providing (e.g., typing) clinical story information for applying to the exam. In various embodiments, once added, the clinical story information will appear under the clinical story tab for the exam. The clinical story tab can also be used by multiple users to add to the clinical story and/or to revise the clinical story in a crowd-sourced manner.

Figure 14A:
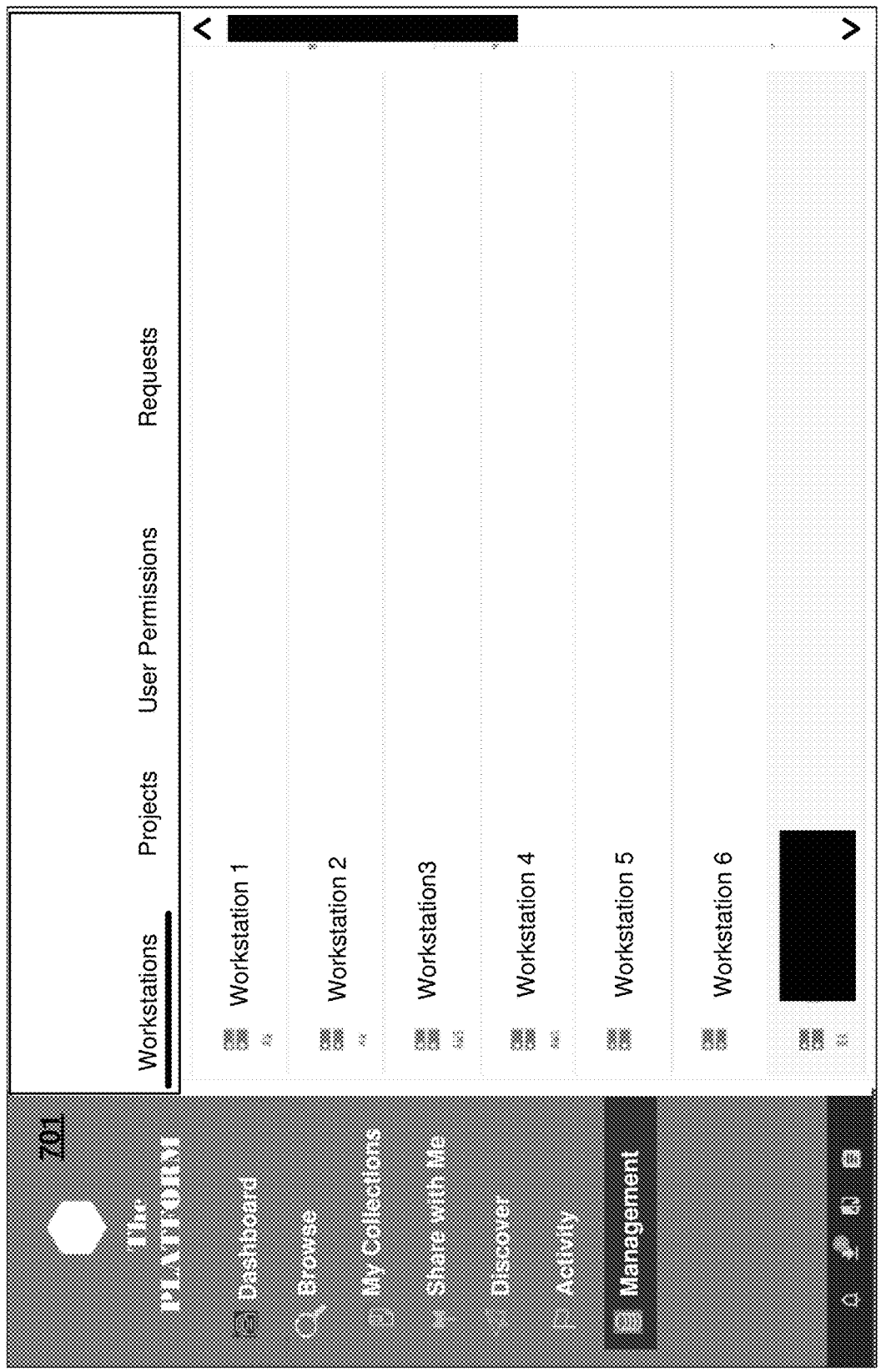
Figure 14B:
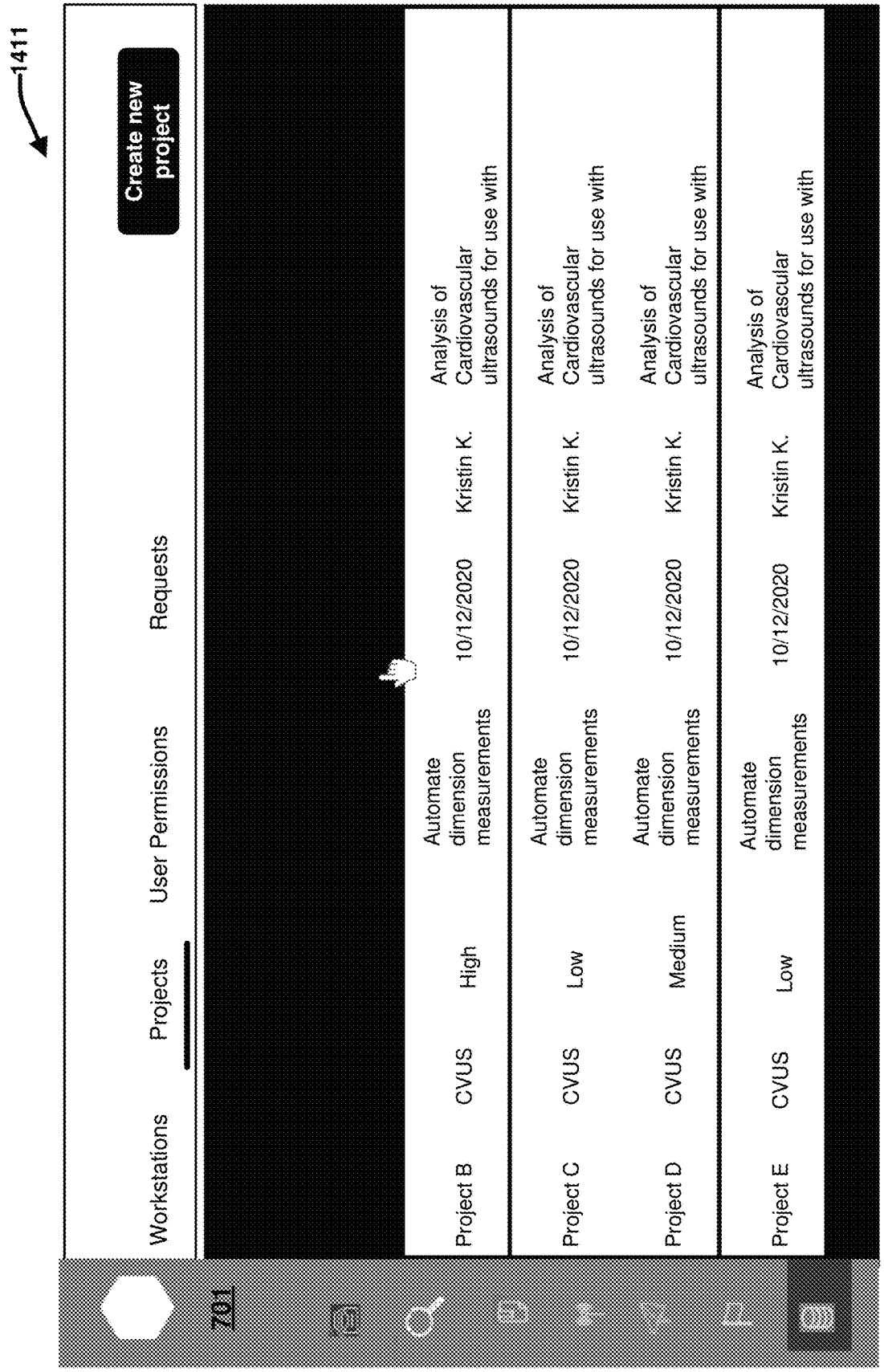

FIGS. 14A-14D presents an example user account management UIs in accordance with one or more embodiments of the disclosed subject matter. In this example, the "Management" page can provide features related to accessing workstations, accessing and creating projects, viewing and applying user permissions, and viewing and performing various requests. In the embodiment shown in FIG. 14A, the workstation tab is selected to present a workstation management UI 1401. FIG. 14B presents an example project management UI 1411 that can be presented in response to selection of the projects tab. The project management UI 1411 can provide a selectable list of the user's current projects and relevant information. In various embodiments, a project can be selected and opened from the list to view information about the project and perform various management actions related to the project. The project management UI 1411 also provides a link to create a new project.

FIG. 14C presents an example request management UI 1421. The request management UI can provide different request categories, including an image request category, an EMR request category, and a user requests category. In the embodiment shown, the images request category is shown and displaying the current image requests associated with this user's account and the current status of the request fulfilment process. In this regard, an image request can include a predefined request for images data satisfying defined criteria that the search component 606 can be configured to fulfil. In this regard, a user can fill out an image request defining criteria of images they need and the search component 606 can be configured to continuously find images until the request is fulfilled. The images request UI further provides a link to create and submit a new request.

FIG. 14D presents example user request features accessed via the user requests tab and correspond user request UI 1431. In this example, the user request tab can provide for creating new request for the user, including submitting a request to remove PHI data from an image/image data set, a request to edit image DICOM data, a request to compare selected image data, a request to find similar images to a selected image, a request to apply one or more image processing functions to an image, and a request to receive feedback on an image. The user requests tab also provides information related to their content and requests made by other users regarding their content.

Figure 15:
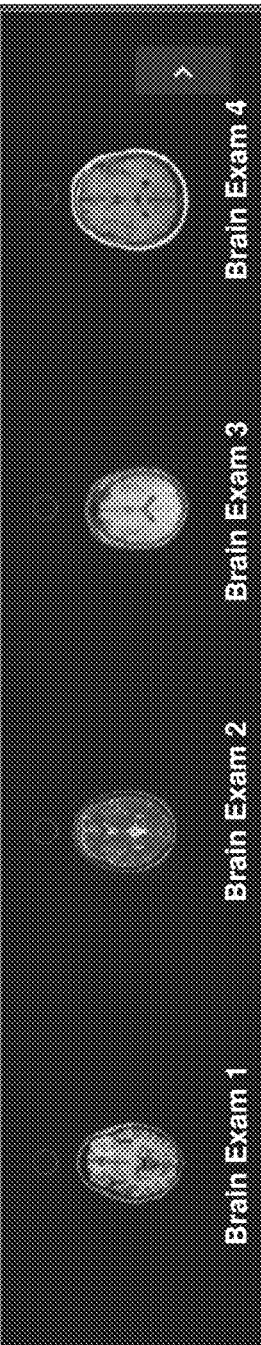
FIG. 15 presents an example UI comparing different brain scans in accordance with one or more embodiments of the disclosed subject matter.

FIG. 15 presents an example compare selection UI 1500 comparing different brain scans in accordance with one or more embodiments of the disclosed subject matter. In various embodiments, this compare selection feature can be accessed via the user requests UI 1431 in association selection of the compare request option. In one or more embodiments, the compare selection feature can allow a user to select two or more exams, series and or images for comparison. In this example, different brain scans have been selected.

Figure 16A:
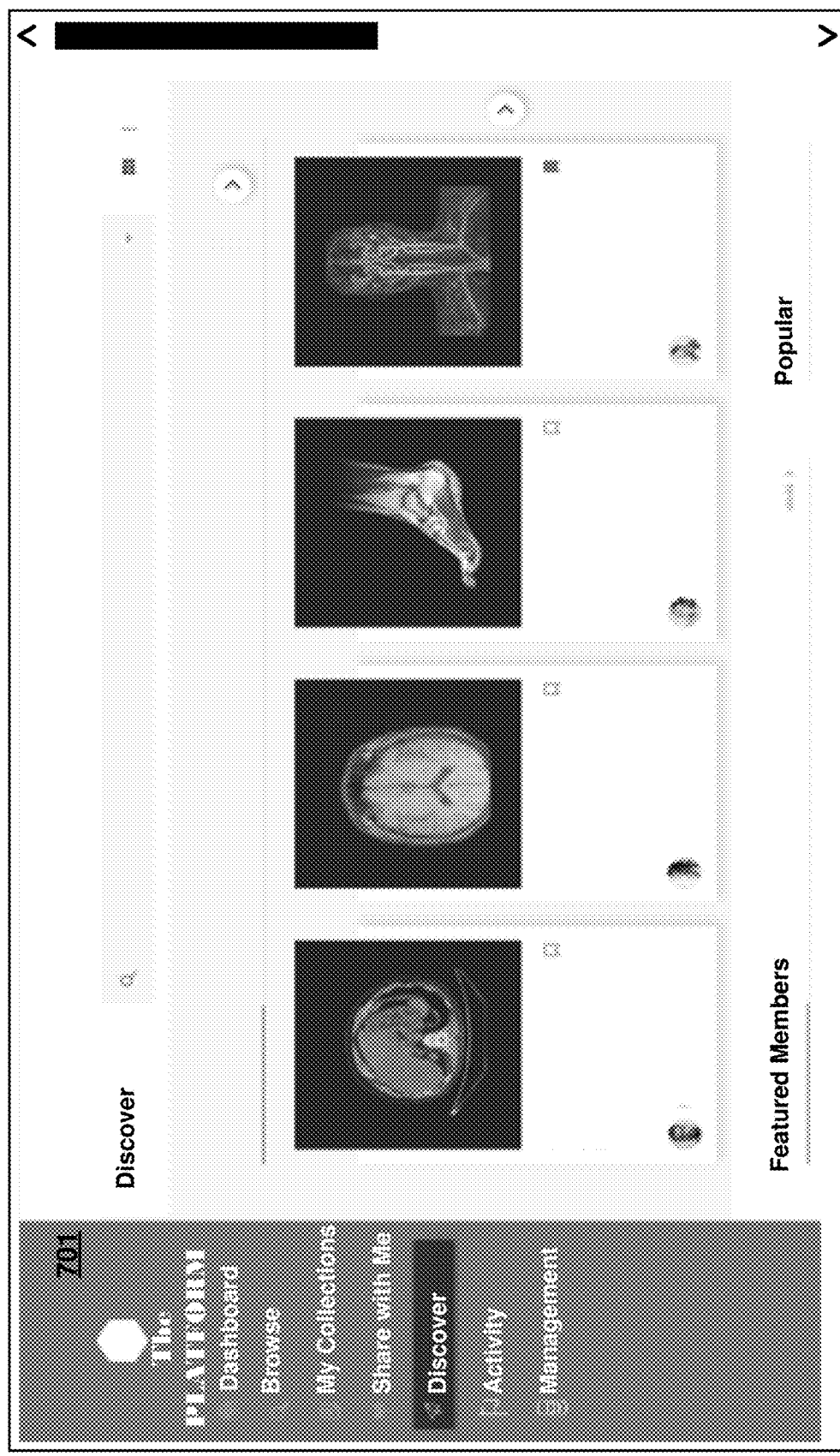
FIGS. 16A-16C present example discover UIs in accordance with one or more embodiments of the disclosed subject matter.
Figure 16B:
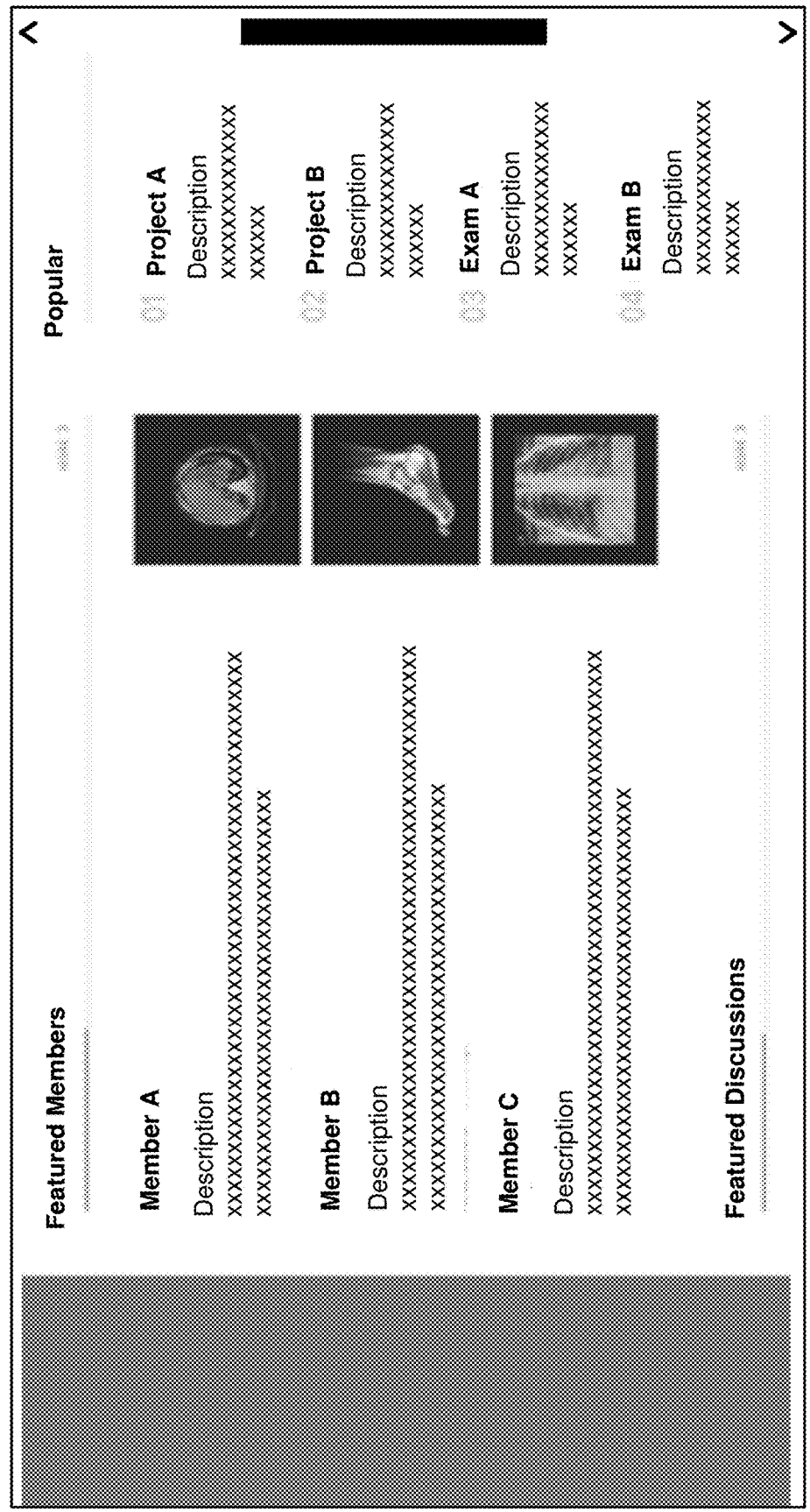
Figure 16C:
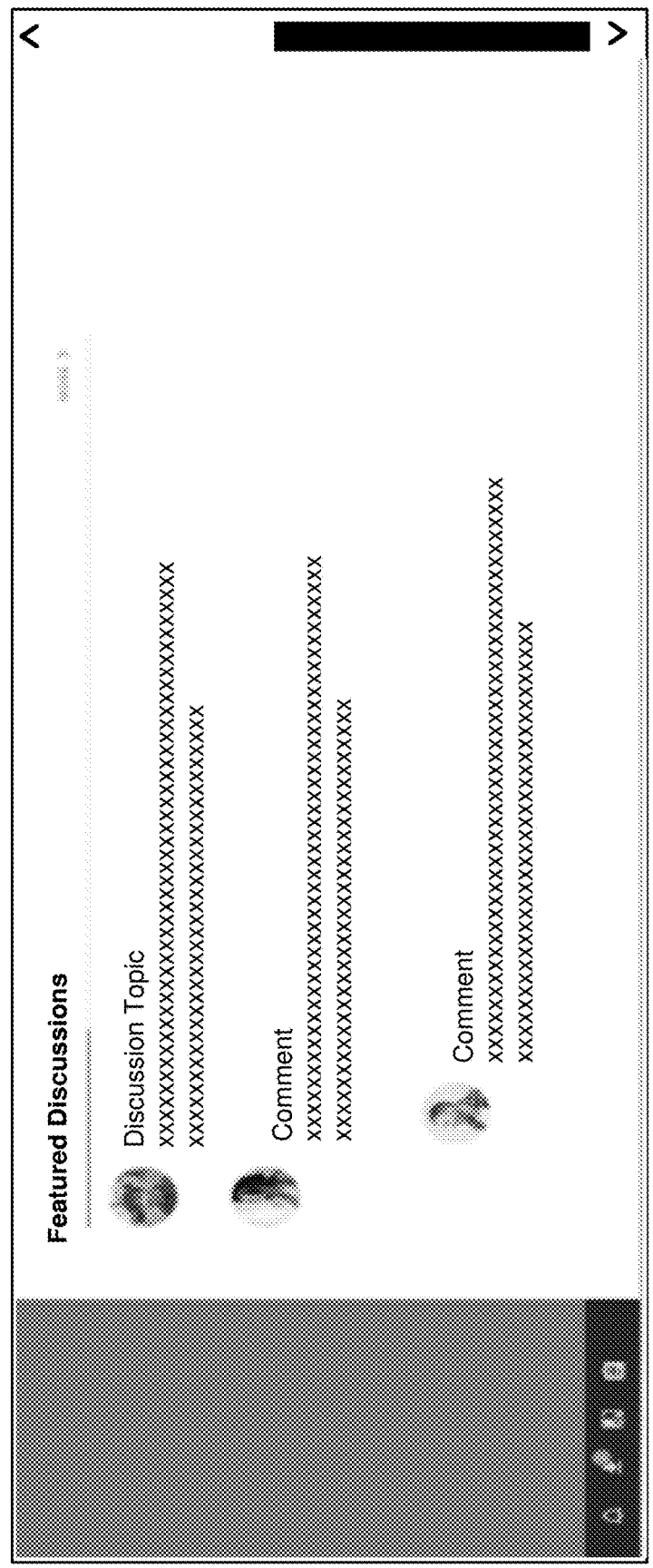

FIGS. 16A-16C present an example discover UI 1600 that can be presented in response to selection of the "Discover" page from the main side menu 701 from the dashboard. In accordance with one or more embodiments of the disclosed subject matter. The example discover UI 1600 present various topics and features that can be tailored to the user's preference and usage history of the platform. FIG. 16A presents an initial view of the scrollable discover UI. This initial view can provide selectable thumbnails of collections, projects, topics, exams and other information categories that can be accessed via the platform. FIG. 16B presents another view of the discover UI 1600 in response to scrolling down. This view includes information regarding featured members and elements popular on the platform. FIG. 16C presents another view of the discover UI 1600 in response to scrolling further down. This view includes information regarding featured discussions between members that the user may be interested in participating in (e.g., determined based on the user's preferences and usage history of the platform).

FIGS. 17A-17D illustrate flow diagrams of example user interaction workflows provided by the platform to search/browse available data, create projects and upload images in accordance with one or more embodiments of the disclosed subject matter.

Figure 17A:
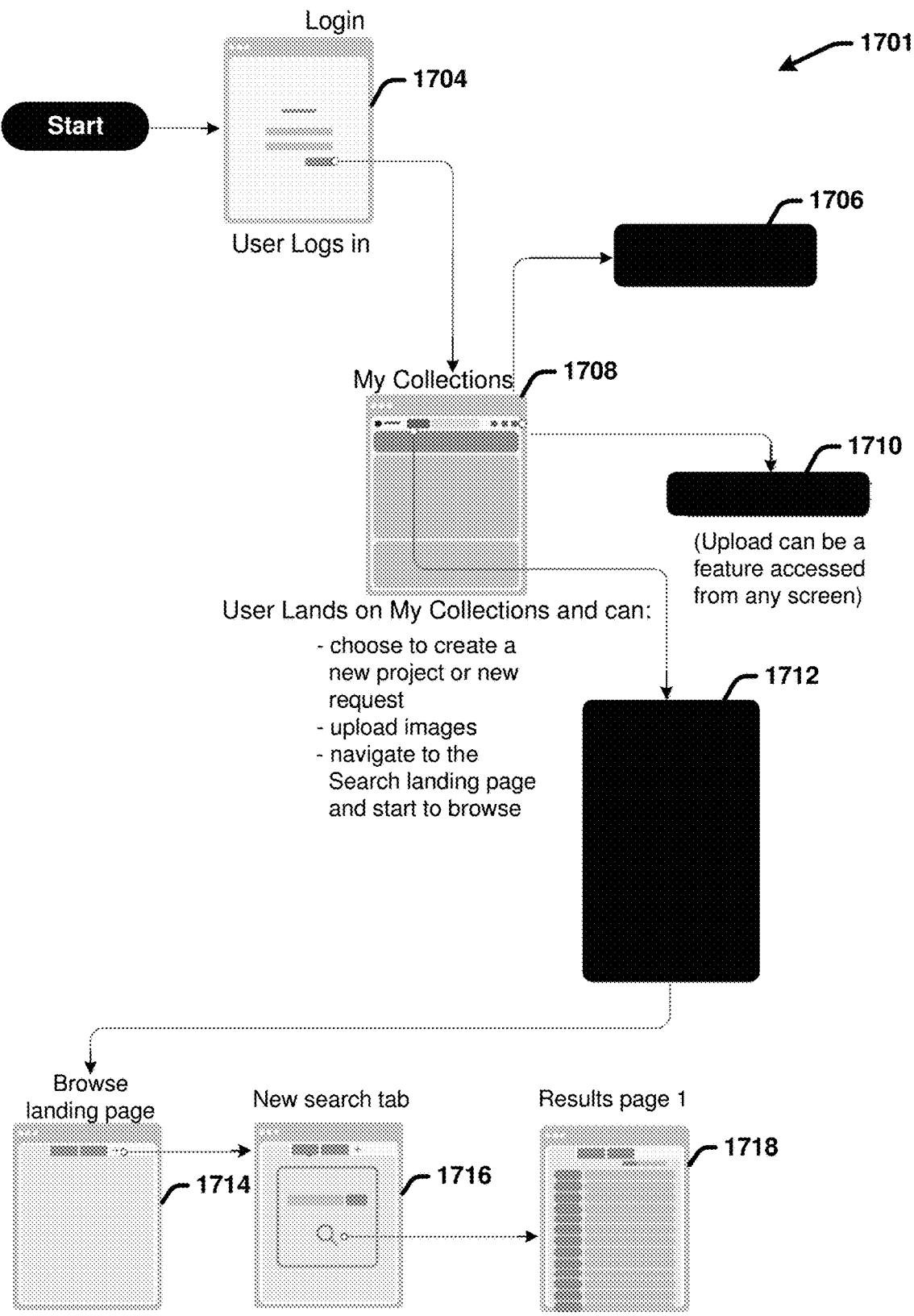
FIGS. 17A-17D illustrate flow diagrams of example user interaction workflows provided by the platform to search/browse available data, create projects and upload images in accordance with one or more embodiments of the disclosed subject matter.

FIG. 17A presents a flow diagram of an example process 1701 for interacting with the platform from the point of initial login. Process 1701 starts initially at 1704 wherein the user logs into their user account with the platform (e.g., via entry of an established username and password or the like). In this example, after successful login, the user can be presented with a "My Collections" landing page that can provide various interactive option that the user can select to perform, including creating a new project 1706, uploading images 1710, and navigating to the browse landing page 1712. In accordance with process 1701, selection of the browse landing page can result in presentation of the browse landing page 1714 that provides search tools for finding image data. For example, in various embodiments, the browse landing page 1714 can be or correspond to search UI 801, series search UI 821 or exam search UI 831. From the browse landing page 1714, the user can the submit a request to perform a new search and enter their desired search criteria in the corresponding search request tab 1716. The user can then be presented with the search results page 1718. For example, in various embodiments, the search results page 1718 can be or correspond to search result UI 811.

Figure 17B:
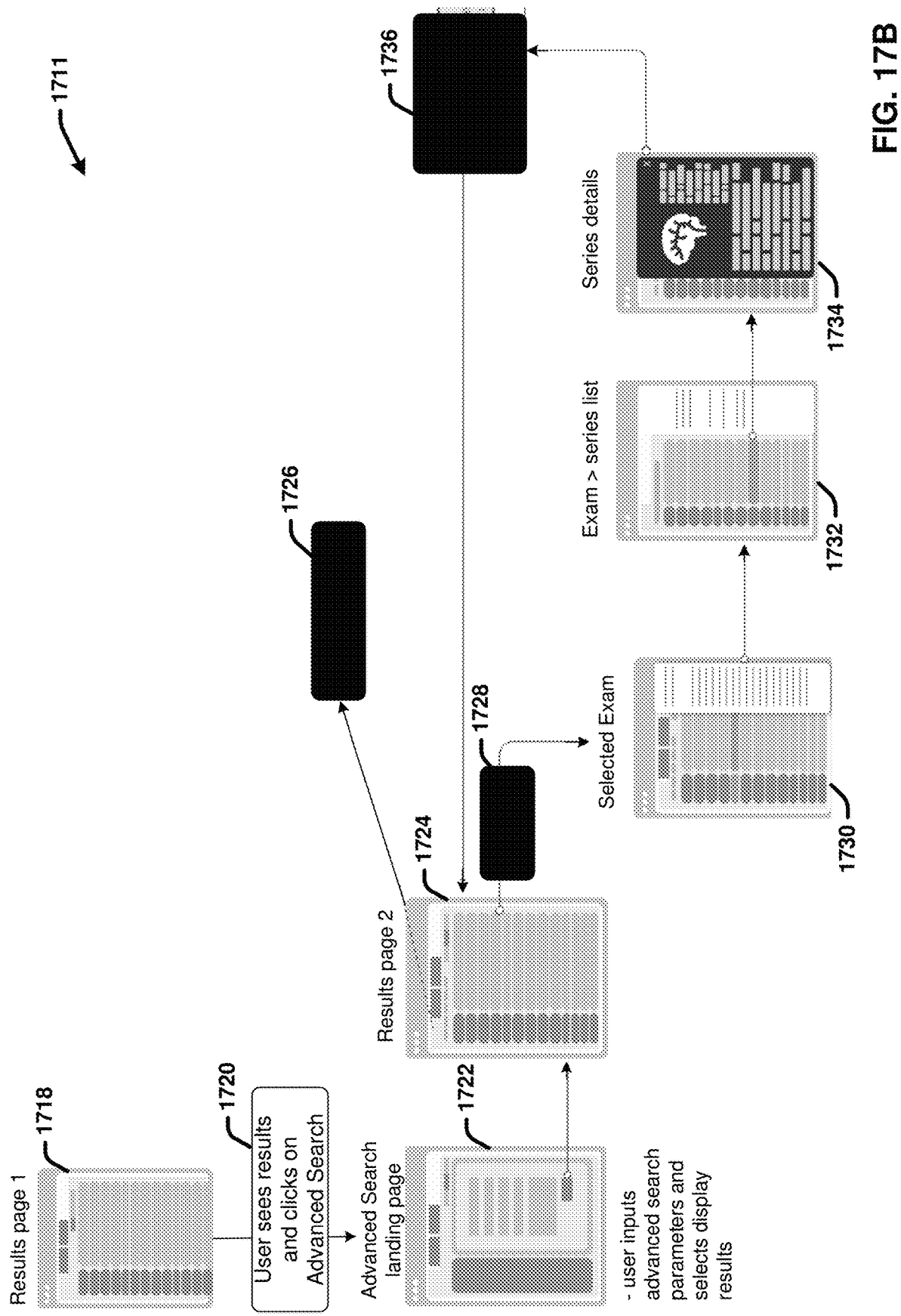

FIG. 17B presents an example process 1711 for further refining a search after landing on the search results page 1718. In this example, at 1720, the user views the initial results and decides to perform an advanced search. The user thus selects the advanced search option resulting in landing on the advanced search landing page. For example, in various embodiments, the advanced search landing page 1722 can be or correspond to the advanced search UI 841. The user can then build an advanced search using the techniques described with reference to FIGS. 8E-8J. In this regard, the user can input the advanced search parameters and selects display results, resulting in presentation of the advanced search results page 1724, referred to as in FIG. 17B as results page 2. From there, the user can perform various actions, including adding the results and/or a selected exam of the results to a project at 1726. At 1728, the user can also view a selected exam, resulting generation of a more detailed view 1730 of the selected exam. For example, in some implementations, the detailed view 1730 can be or correspond to preview view 902. From there the user can open the exam to be presented with a series list 1732. The user can further select a specific series for viewing additional details at 1734 as described with reference to FIGS. 10A-10E (e.g., using a viewer component 108). When the user has finished viewing the series, they can select to go back to the search results page 2 at 1736/

Figure 17C:
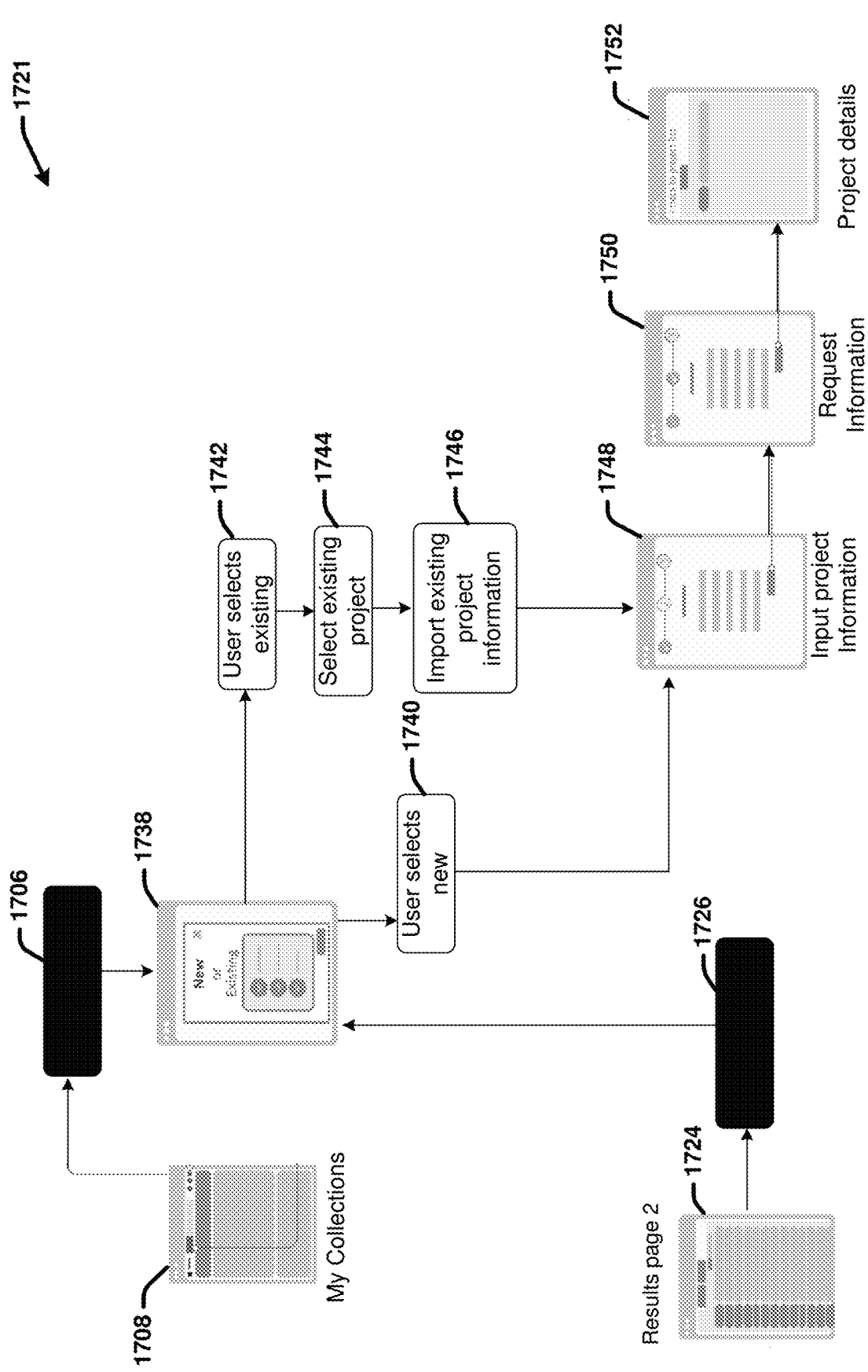

FIG. 17C presents an example process 1721 for adding image data to a project. In one implementation, process 1712 can be initiated from the search results page 1724. With this implementation, at 1726, the user can select to add the search results or a selected exam to a project, resulting in presentation of the project landing page 1738. In another implementation, the user can select the create project option 1706 from the "My Collections" landing page. The create project landing page 1738 can present the user with an option to either create a new project or add to an existing project. In one or more embodiments in which the user selects to create a new project at 1740, the user can be presented with the input project information page 1748. From there, the user can import the search results, a selected exam from the search results, and/or a collection for the project and defined the project information. In another implementation in which the user selects to add to an existing project at 1742, at 1744, the user can select the existing project and at 1746, the system can import the existing project information. At 1750, the user can further fill out any desired requests for the project (e.g., image data fulfilment requests, image processing request, PHI requests, etc.). At 1752, the user can be presented with a project information page summarizing the details of the project, the image data associated with the project and the requests associated with the project.

Figure 17D:
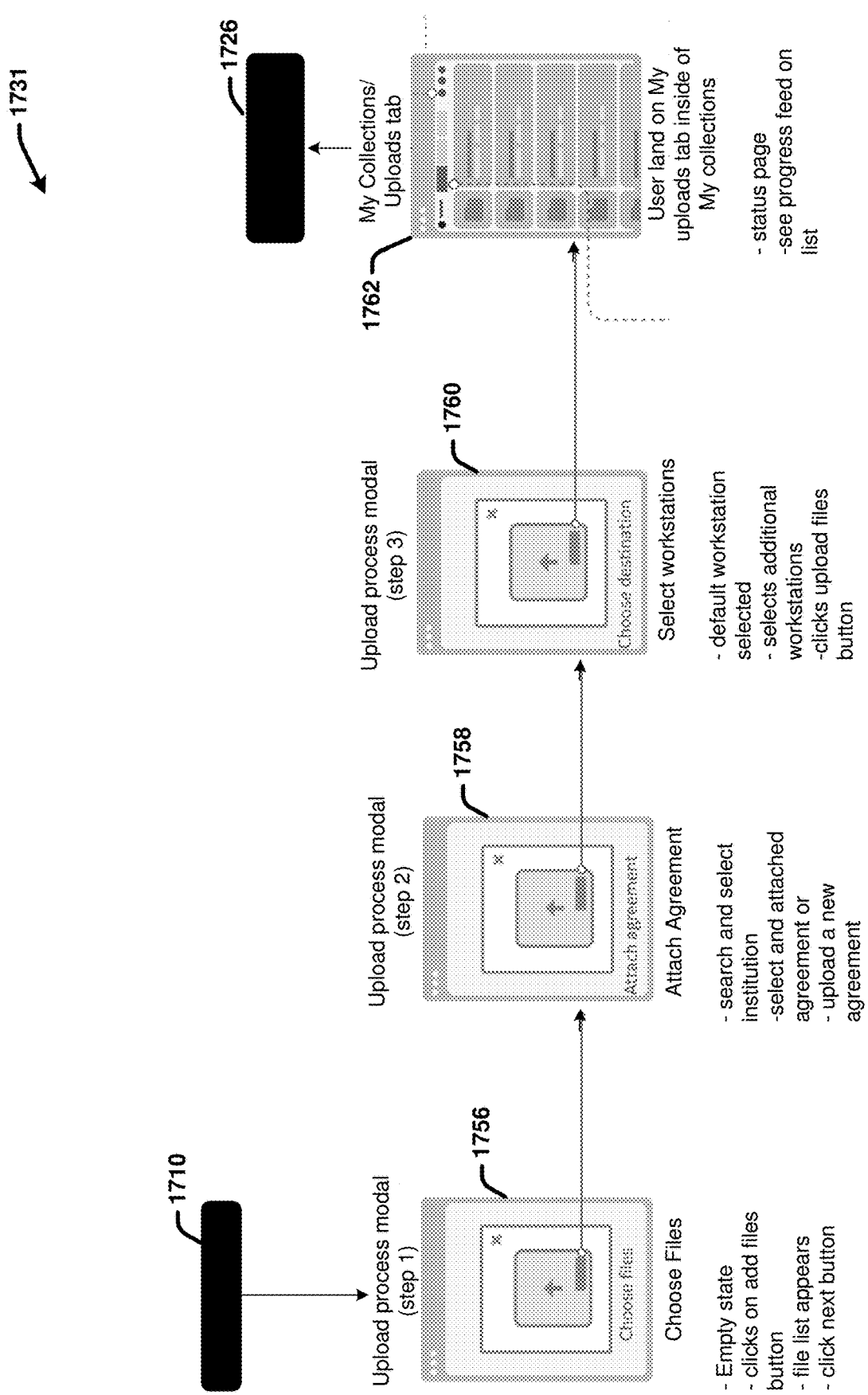

FIG. 17D presents an example process 1731 for uploading images to the platform. Process 1731 can begin at 1710 wherein the user selects a request to upload images (e.g., from the "My Collections" page or another page). At 1756, the user can choose files for uploading. At 1758, the user can attach a scope agreement that restricts the scope of usage of the upload files by other users after they become accessible via the platform following upload. At 1760, the user can select one or more workstations (e.g., image storage endpoints 102) for storing the uploaded files. At 1762, the user can be returned back to the "My Collections" tab and/or a "My upload" page where they can see the progress of the upload. In various embodiment, uploaded image data can be added to the user's collections. One uploaded, the user can optionally add the image data to a project at 1726, view the image data, share the image data, and the like using the various features and functionalities of the platform.

Figure 18:
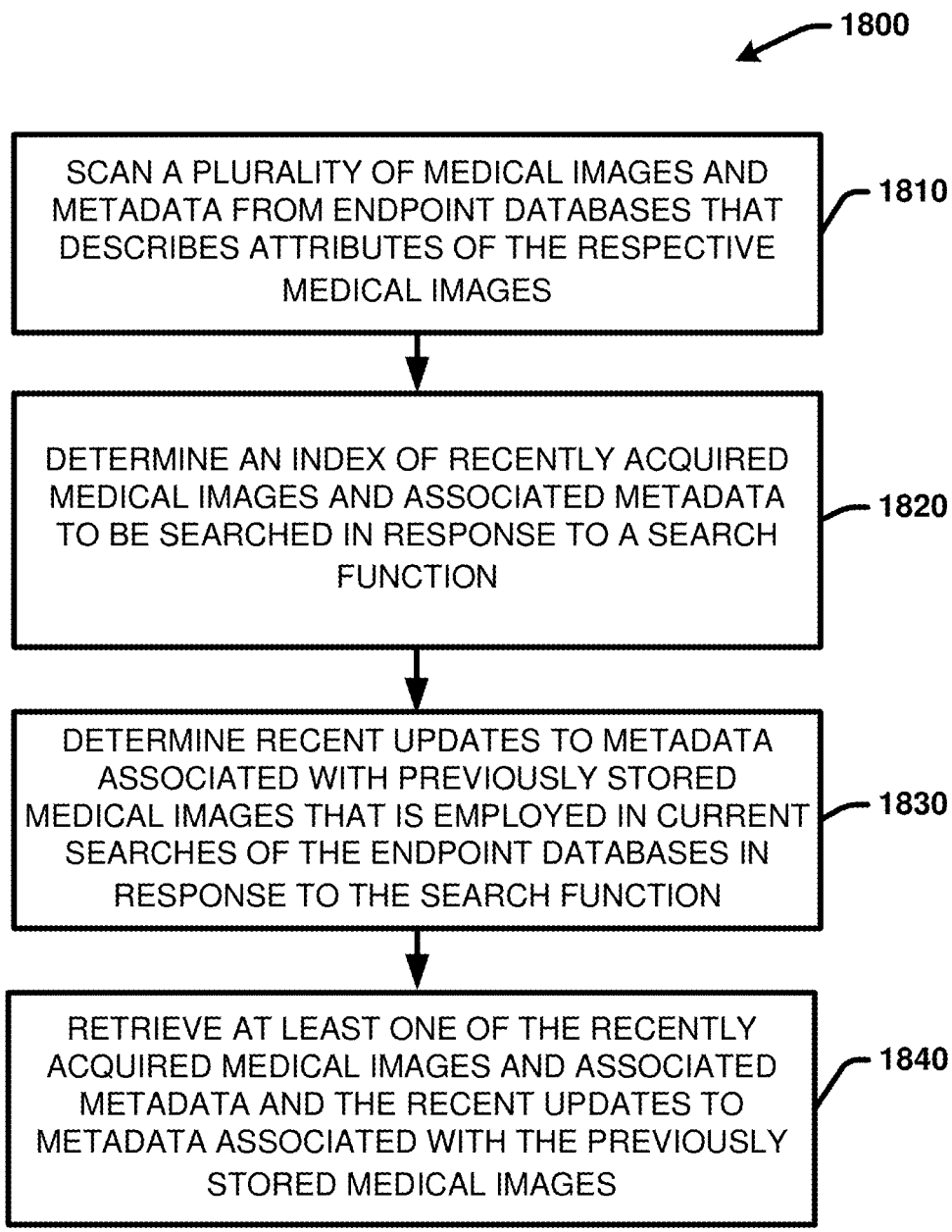
FIG. 18 illustrates a flow diagram of an example method to execute workflow instructions to locate, retrieve, and analyze a medical image and associated metadata in accordance with one or more embodiments of the disclosed subject matter.

FIG. 18 illustrates an example method 1800 to execute to analyze a medical image and associated metadata, in accordance with one or more examples of the disclosed subject matter. At 1810, the method 1800 includes scanning, by a system operatively coupled to a processor, a plurality of medical images and metadata from endpoint databases that describes attributes of the respective medical images. At 1820, the method 1800 includes determining, by the system, an index of recently acquired medical images and associated metadata to be searched in response to a search function. At 1830 the method 1800 includes determining, by the system, recent updates to metadata associated with previously stored medical images that is employed in current searches of the endpoint databases in response to the search function. At 1840, the method 1800 includes retrieving, by the system, at least one of the recently acquired medical images and associated metadata and the recent updates to metadata associated with the previously stored medical images.

Figure 19:
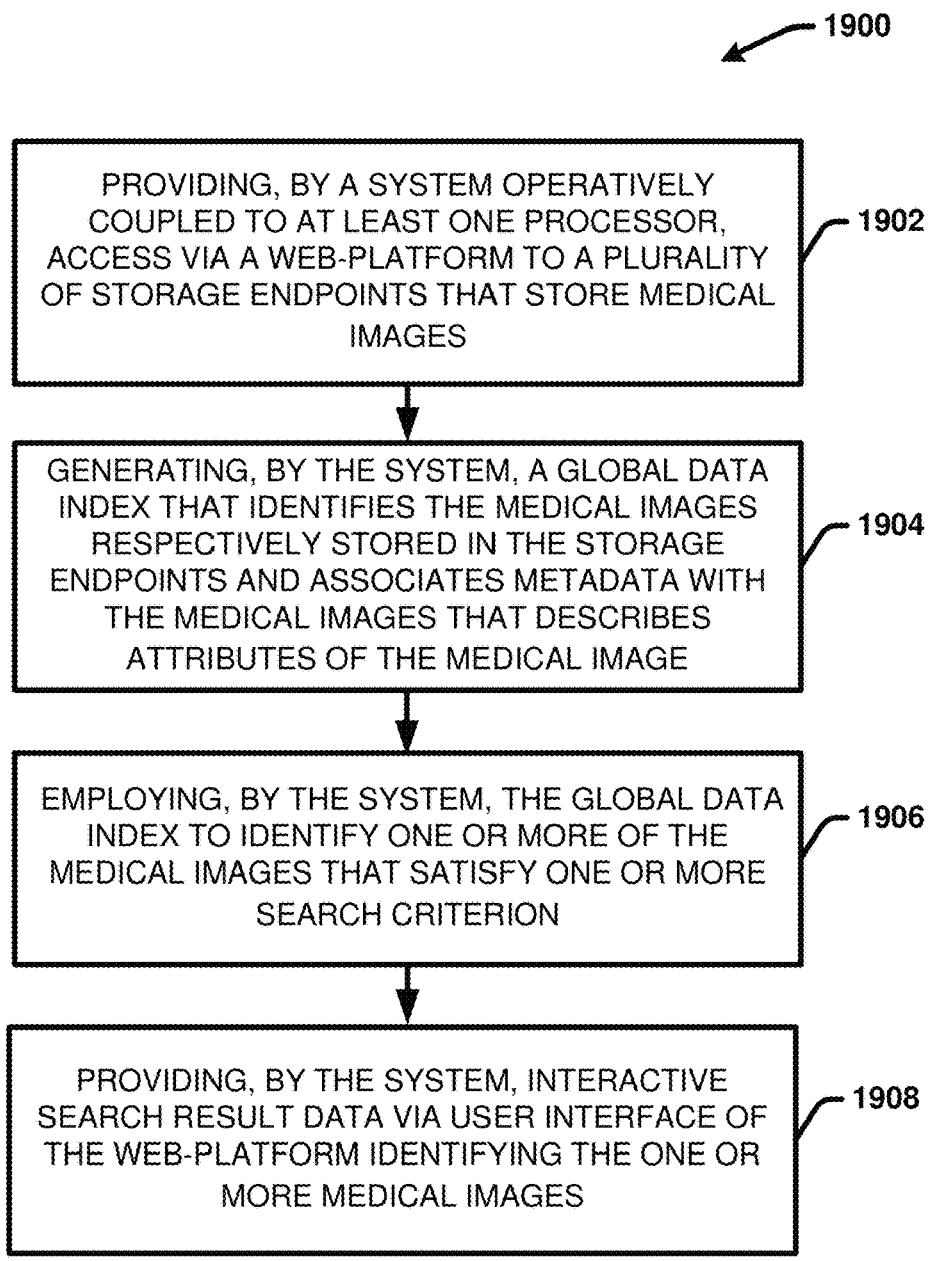
FIG. 19 illustrates a flow diagram of another example method to execute workflow instructions to locate, retrieve, and analyze a medical image and associated metadata in accordance with one or more embodiments of the disclosed subject matter.

FIG. 19 illustrates a flow diagram of another example method to execute workflow instructions to locate, retrieve, and analyze a medical image and associated metadata in accordance with one or more embodiments of the disclosed subject matter. At 1902 the method includes providing, by a system operatively coupled to at least one processor, access via a web-platform to a plurality of storage endpoints that store medical images. At 1904, the method includes generating, by the system, a global data index that identifies the medical images respectively stored in the storage endpoints and associates metadata with the medical images that describes attributes of the medical images. At 1906, the method includes employing, by the system, the global data index to identify one or more of the medical images that satisfy one or more search criterion. At 1908, the method includes providing, by the system, interactive search result data via user interface of the web-platform identifying the one or more medical images.

One or more examples can be a system, a method, and/or a computer program product at any possible technical detail level of integration. The computer program product can include a computer readable storage medium (or media) having computer readable program instructions thereon for causing a processor to carry out one or more aspects of the present examples.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the entity's computer, partly on the entity's computer, as a stand-alone software package, partly on the entity's computer and partly on a remote computer or entirely on the remote computer or server. In the latter scenario, the remote computer can be connected to the entity's computer through any type of network, including a local area network (LAN) or a wide area network (WAN), or the connection can be made to an external computer (for example, through the Internet using an Internet Service Provider). In some examples, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to examples of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various examples of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 20, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 20:
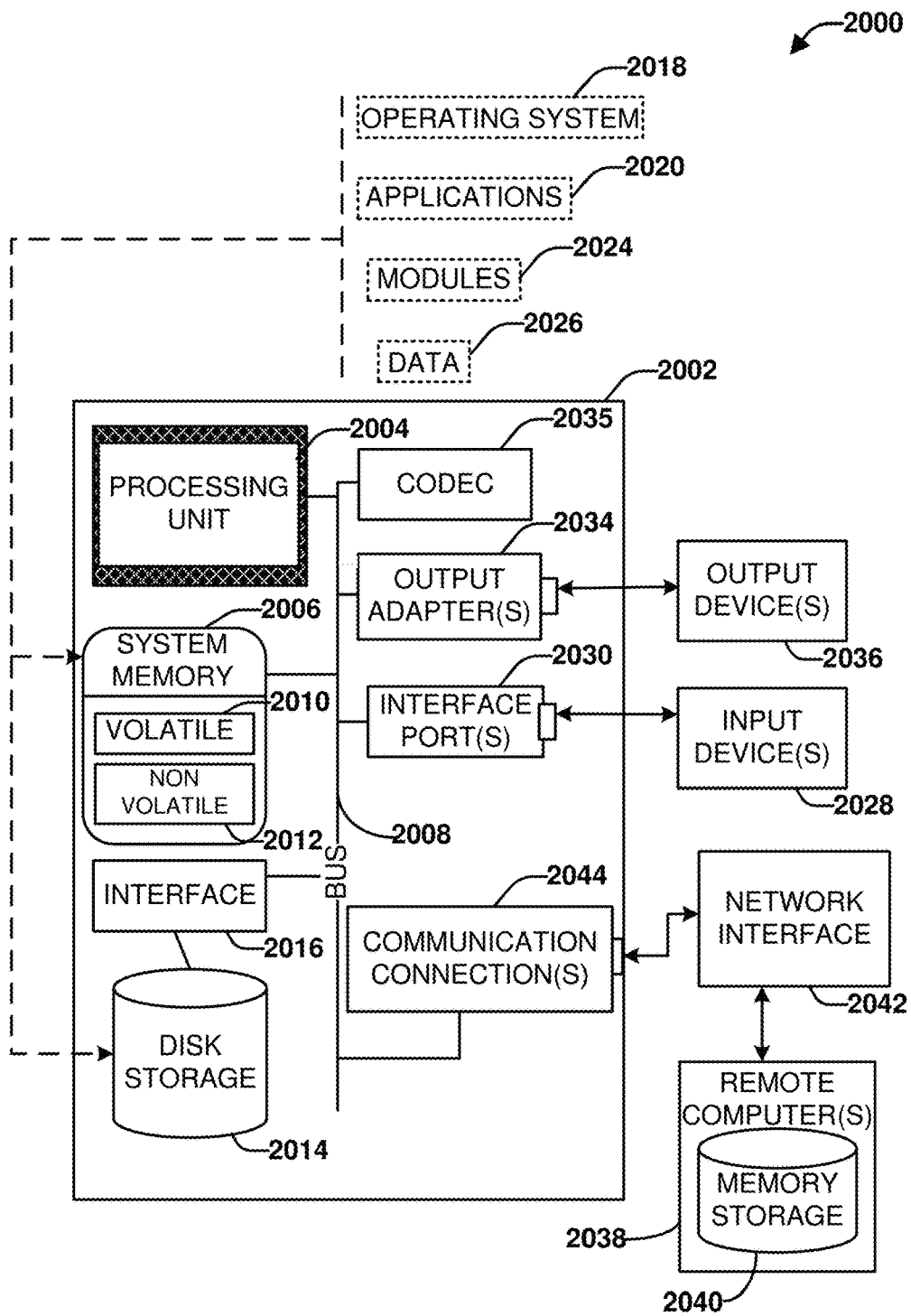
FIG. 20 illustrates a block diagram of an example, non-limiting operating environment in which one or more examples described herein can be facilitated.

With reference to FIG. 20, an example environment 2000 for implementing various aspects of the claimed subject matter includes a computer 2002. The computer 2002 includes a processing unit 2004, a system memory 2006, a codec 2035, and a system bus 2008. The system bus 2008 couples system components including, but not limited to, the system memory 2006 to the processing unit 2004. The processing unit 2004 can be any of various available processors. Dual microprocessors and other multiprocessor architectures also can be employed as the processing unit 2004.

The system bus 2008 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13154), and Small Computer Systems Interface (SCSI).

The system memory 2006 includes volatile memory 2010 and non-volatile memory 2012, which can employ one or more of the disclosed memory architectures, in various examples. The basic input/output system (BIOS), containing the basic routines to transfer information between elements within the computer 2002, such as during start-up, is stored in non-volatile memory 2012. In addition, according to present innovations, codec 2035 can include at least one of an encoder or decoder, wherein the at least one of an encoder or decoder can consist of hardware, software, or a combination of hardware and software. Although, codec 2035 is depicted as a separate component, codec 2035 can be contained within non-volatile memory 2012. By way of illustration, and not limitation, non-volatile memory 2012 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 2012 can employ one or more of the disclosed memory devices, in at least some examples. Moreover, non-volatile memory 2012 can be computer memory (e.g., physically integrated with computer 2002 or a mainboard thereof), or removable memory. Examples of suitable removable memory with which disclosed examples can be implemented can include a secure digital (SD) card, a compact Flash (CF) card, a universal serial bus (USB) memory stick, or the like. Volatile memory 2010 includes random access memory (RAM), which acts as external cache memory, and can also employ one or more disclosed memory devices in various examples. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 2002 can also include removable/non-removable, volatile/non-volatile computer storage medium. FIG. 20 illustrates, for example, disk storage 2014. Disk storage 2014 includes, but is not limited to, devices like a magnetic disk drive, solid state disk (SSD), flash memory card, or memory stick. In addition, disk storage 2014 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 2014 to the system bus 2008, a removable or non-removable interface is typically used, such as interface 2016. It is appreciated that disk storage 2014 can store information related to an entity. Such information might be stored at or provided to a server or to an application running on an entity device. In one example, the entity can be notified (e.g., by way of output device(s) 2036) of the types of information that are stored to disk storage 2014 or transmitted to the server or application. The entity can be provided the opportunity to opt-in or opt-out of having such information collected or shared with the server or application (e.g., by way of input from input device(s) 2028).

It is to be appreciated that FIG. 20 describes software that acts as an intermediary between entities and the basic computer resources described in the suitable operating environment 2000. Such software includes an operating system 2018. Operating system 2018, which can be stored on disk storage 2014, acts to control and allocate resources of the computer system 2002. Applications 2020 take advantage of the management of resources by operating system 2018 through program modules 2024, and program data 2026, such as the boot/shutdown transaction table and the like, stored either in system memory 2006 or on disk storage 2014. It is to be appreciated that the claimed subject matter can be implemented with various operating systems or combinations of operating systems.

An entity enters commands or information into the computer 2002 through input device(s) 2028. Input devices 2028 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 2004 through the system bus 2008 via interface port(s) 2030. Interface port(s) 2030 include, for example, a serial port, a parallel port, a game port, and a universal serial bus (USB). Output device(s) 2036 use some of the same type of ports as input device(s) 2028. Thus, for example, a USB port can be used to provide input to computer 2002 and to output information from computer 2002 to an output device 2036. Output adapter 2034 is provided to illustrate that there are some output devices 2036 like monitors, speakers, and printers, among other output devices 2036, which require special adapters. The output adapters 2034 include, by way of illustration and not limitation, video and sound cards that provide a means of connection between the output device 2036 and the system bus 2008. It should be noted that other devices or systems of devices provide both input and output capabilities such as remote computer(s) 2038.

Computer 2002 can operate in a networked environment using logical connections to one or more remote computers, such as remote computer(s) 2038. The remote computer(s) 2038 can be a personal computer, a server, a router, a network PC, a workstation, a microprocessor based appliance, a peer device, a smart phone, a tablet, or other network node, and typically includes many of the elements described relative to computer 2002. For purposes of brevity, only a memory storage device 2040 is illustrated with remote computer(s) 2038. Remote computer(s) 2038 is logically connected to computer 2002 through a network interface 2042 and then connected via communication connection(s) 2044. Network interface 2042 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 2044 refers to the hardware/software employed to connect the network interface 2042 to the bus 2008. While communication connection 2044 is shown for illustrative clarity inside computer 2002, it can also be external to computer 2002. The hardware/software necessary for connection to the network interface 2042 includes, for exemplary purposes only, internal and external technologies such as, modems including regular telephone grade modems, cable modems and DSL modems, ISDN adapters, and wired and wireless Ethernet cards, hubs, and routers.

The illustrated aspects of the disclosure may also be practiced in distributed computing environments where certain tasks are performed by remote processing devices that are linked through a communications network. In a distributed computing environment, program modules can be located in both local and remote memory storage devices.

Figure 21:
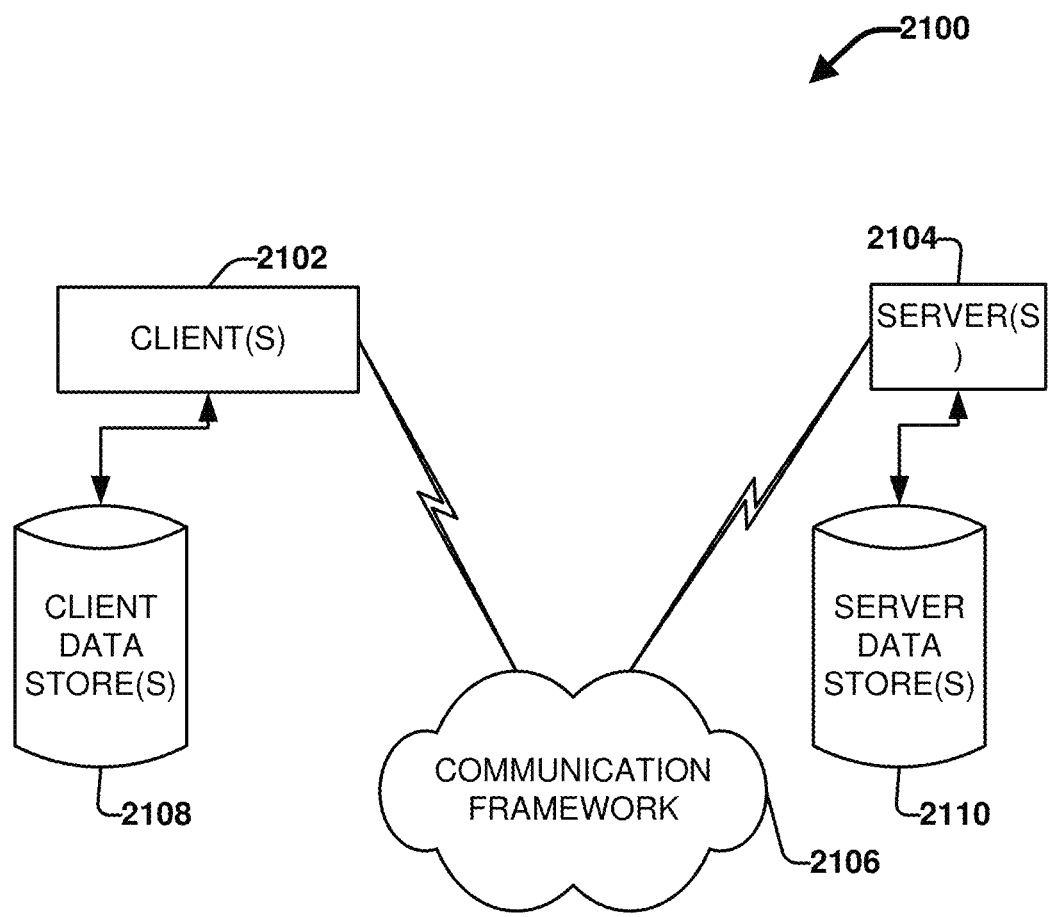
FIG. 21 illustrates a block diagram of another example, non-limiting operating environment in which one or more examples described herein can be facilitated.

Referring to FIG. 21, there is illustrated a schematic block diagram of a computing environment 2100 in accordance with this disclosure in which the subject systems (e.g., systems 1800, 2200, 2400 and the like), methods and computer readable media can be deployed. The computing environment 2100 includes one or more client(s) 2102 (e.g., laptops, smart phones, PDAs, media players, computers, portable electronic devices, tablets, and the like). The client(s) 2102 can be hardware and/or software (e.g., threads, processes, computing devices). The computing environment 2100 also includes one or more server(s) 2104. The server(s) 2104 can also be hardware or hardware in combination with software (e.g., threads, processes, computing devices). The servers 2104 can house threads to perform transformations by employing aspects of this disclosure, for example. In various examples, one or more components, devices, systems, or subsystems of system 1800, 2200 and 2400, can be deployed as hardware and/or software at a client 2102 and/or as hardware and/or software deployed at a server 2104. One possible communication between a client 2102 and a server 2104 can be in the form of a data packet transmitted between two or more computer processes wherein the data packet may include healthcare related data, training data, AI models, input data for the AI models and the like. The data packet can include a metadata, e.g., associated contextual information, for example. The computing environment 2100 includes a communication framework 2106 (e.g., a global communication network such as the Internet, or mobile network(s)) that can be employed to facilitate communications between the client(s) 2102 and the server(s) 2104.

Communications can be facilitated via a wired (including optical fiber) and/or wireless technology. The client(s) 2102 include or are operatively connected to one or more client data store(s) 2108 that can be employed to store information local to the client(s) 2102 (e.g., associated contextual information). Similarly, the server(s) 2104 are operatively include or are operatively connected to one or more server data store(s) 2110 that can be employed to store information local to the servers 2104.

In one example, a client 2102 can transfer an encoded file, in accordance with the disclosed subject matter, to server 2104. Server 2104 can store the file, decode the file, or transmit the file to another client 2102. It is to be appreciated, that a client 2102 can also transfer uncompressed file to a server 2104 and server 2104 can compress the file in accordance with the disclosed subject matter. Likewise, server 2104 can encode video information and transmit the information via communication framework 2106 to one or more clients 2102.

Figure 22:
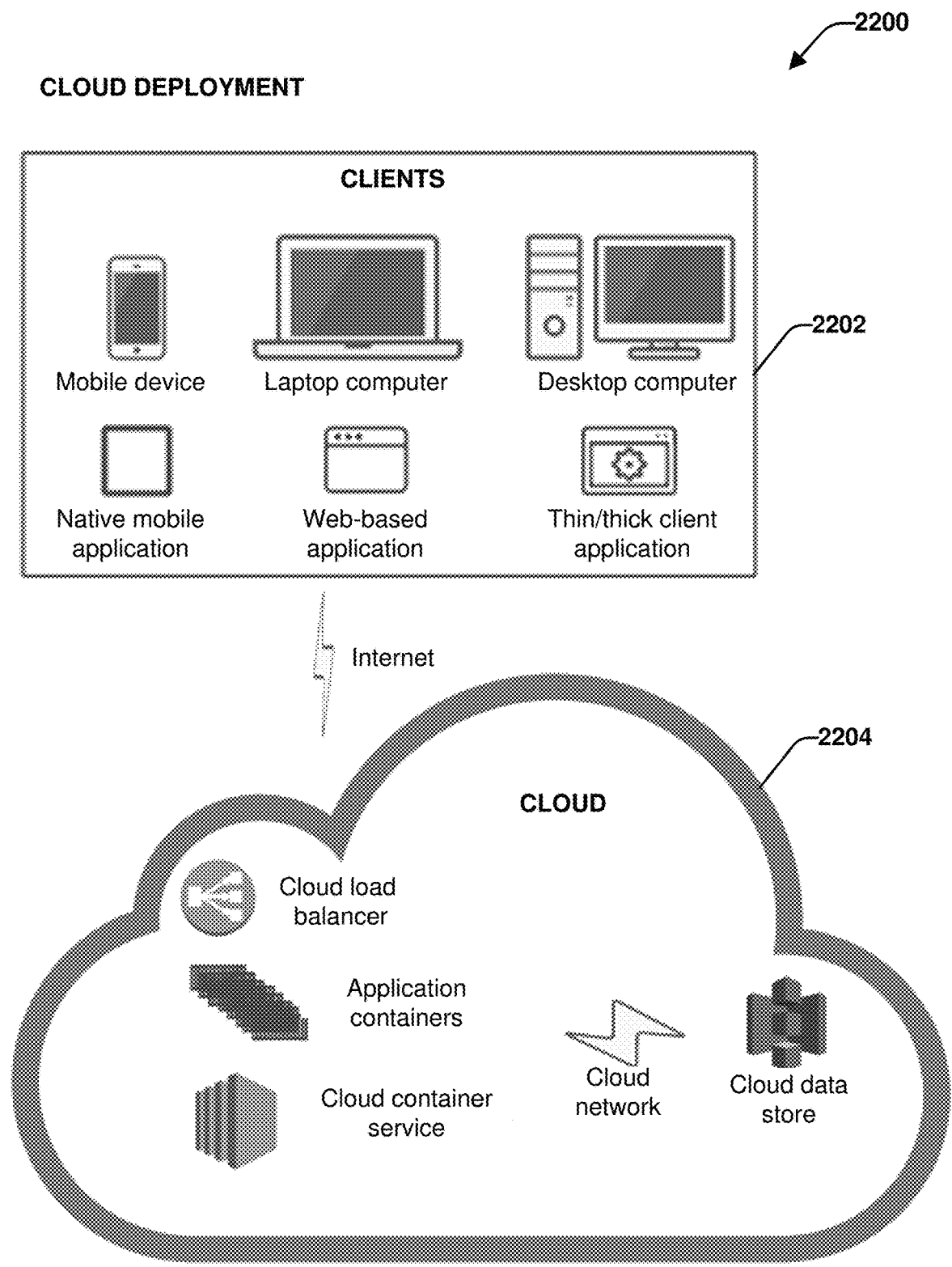
FIG. 22 illustrates a block diagram of another example, non-limiting operating environment in which one or more examples described herein can be facilitated.

FIG. 22 illustrates a schematic block diagram of another example computing environment 2200 in accordance with this disclosure in which the subject systems (e.g., system 100), methods and computer readable media can be deployed. The computing environment 2200 includes a cloud deployment architecture consisting of one or more clients 2202 that can be communicatively coupled to a system cloud 2204 via a network (e.g., the Internet). The system cloud 2204 can include a cloud load balances, one or more application container, one or more cloud service containers, a cloud data store, and a cloud network that communicatively couples the one or more cloud components to the cloud data store. In accordance with the cloud deployment architecture, the clients 2202 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject platform orchestration server 116 and/or platform orchestration server 600 deployed in the system cloud 2204. In various implementations, the one or more components of system 100 and/or platform orchestration server 600 can be distributed between the clients 2202 and the system cloud 2204.

Figure 23:
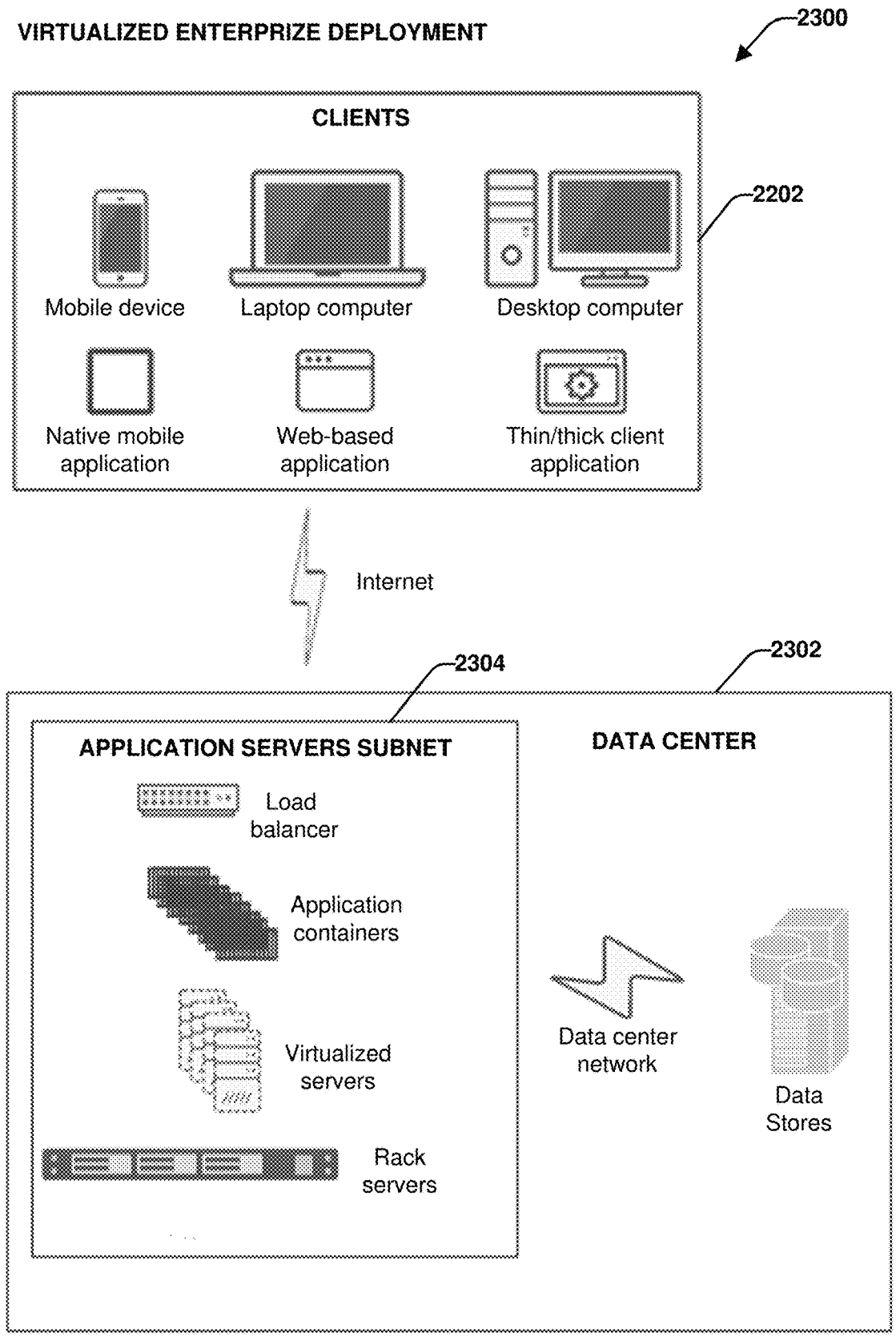
FIG. 23 illustrates a block diagram of another example, non-limiting operating environment in which one or more examples described herein can be facilitated.

FIG. 23 illustrates a schematic block diagram of another example computing environment 2300 in accordance with this disclosure in which the subject systems (e.g., system 100), methods and computer readable media can be deployed. The computing environment 2300 includes a virtualized enterprise deployment consisting of one or more clients 2202 that can be communicatively coupled to a remote data center 2302 via a network (e.g., the Internet). The remote data center 2302 can include an application servers subnet 2304 which can provide a load balancer, one or more application containers, one or more virtualized servers and one or more rack servers. The data center 2302 can also include one or more data stores that can be communicatively coupled to the application servers subnet 2304 via a data center network. In accordance with the virtualized enterprise deployment, the clients 2202 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject platform orchestration server 116 and/or platform orchestration server 600 deployed in the data center 2202 and application servers subnet 2304. In various implementations, the one or more components of system 100 and/or platform orchestration server 600 can be distributed between the clients 2202 and the application servers subnet 2304 and the data center 2302.

Figure 24:
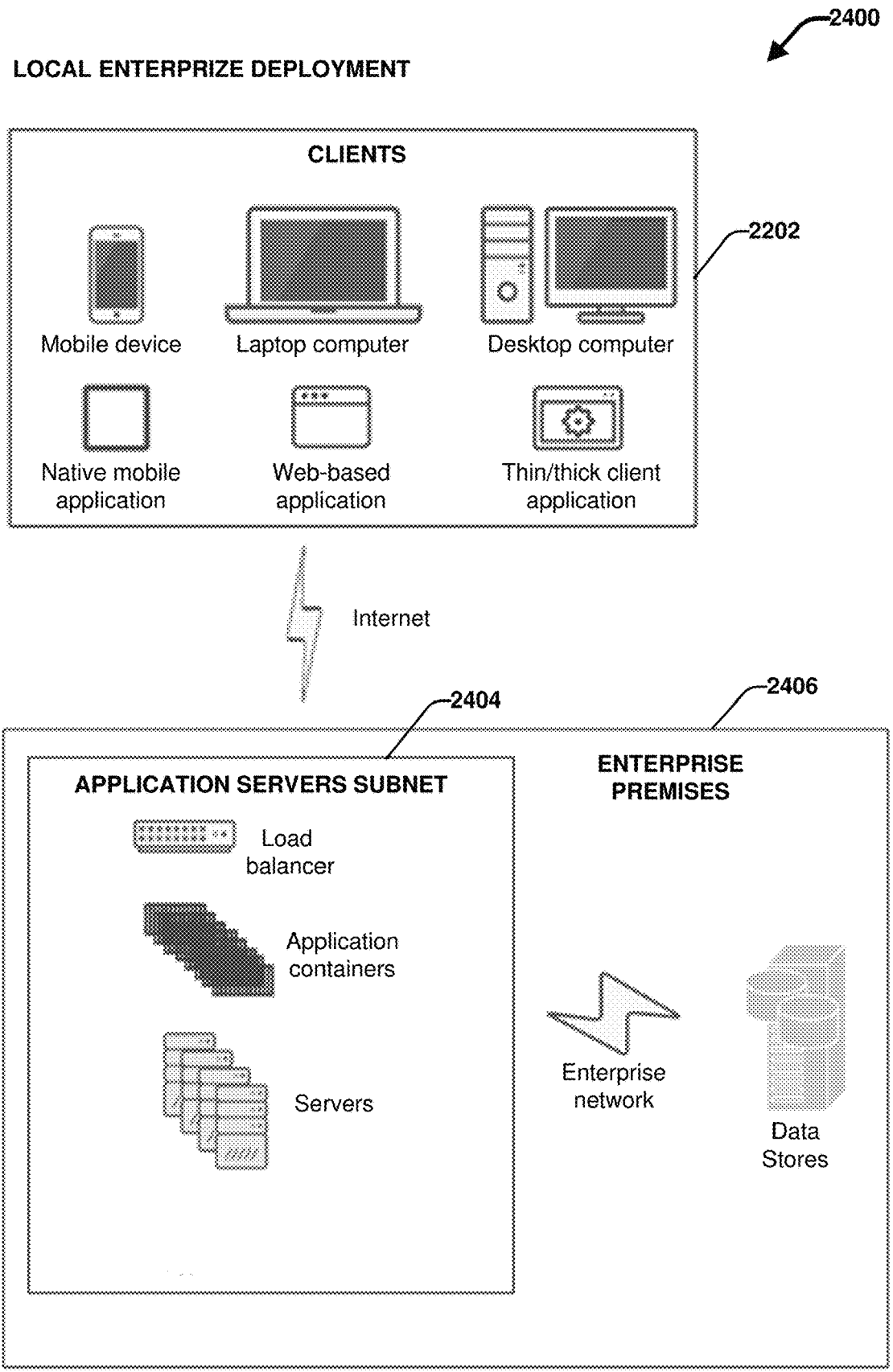
FIG. 24 illustrates a block diagram of another example, non-limiting operating environment in which one or more examples described herein can be facilitated.

FIG. 24 illustrates a schematic block diagram of another example computing environment 2400 in accordance with this disclosure in which the subject systems (e.g., system 100), methods and computer readable media can be deployed. The computing environment 2400 includes a local enterprise deployment consisting of one or more clients 2202 that can be communicatively coupled to an application servers subnet 2404 via a network (e.g., the Internet). In accordance with this example, the application servers subnet 2404 can be provided at the enterprise premises 2402 (e.g., as opposed to a remote data center 2402). The application servers subnet 2404 can include a load balancer, one or more application containers and one or more servers. The application servers subnet 2404 can be communicatively coupled to one or more data stores provided at the enterprise premises 2402 via an enterprise network. Similar to the cloud and virtualized enterprise deployments, the clients 2202 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject platform orchestration server 116 and/or platform orchestration server 600 deployed at the enterprise premises 2402 and the application servers subnet 2404. In various implementations, the one or more components of system 100 and/or orchestration server 600 can be distributed between the clients 2202 and the application servers subnet 2404 and the enterprise premises 2402.

Figure 25:
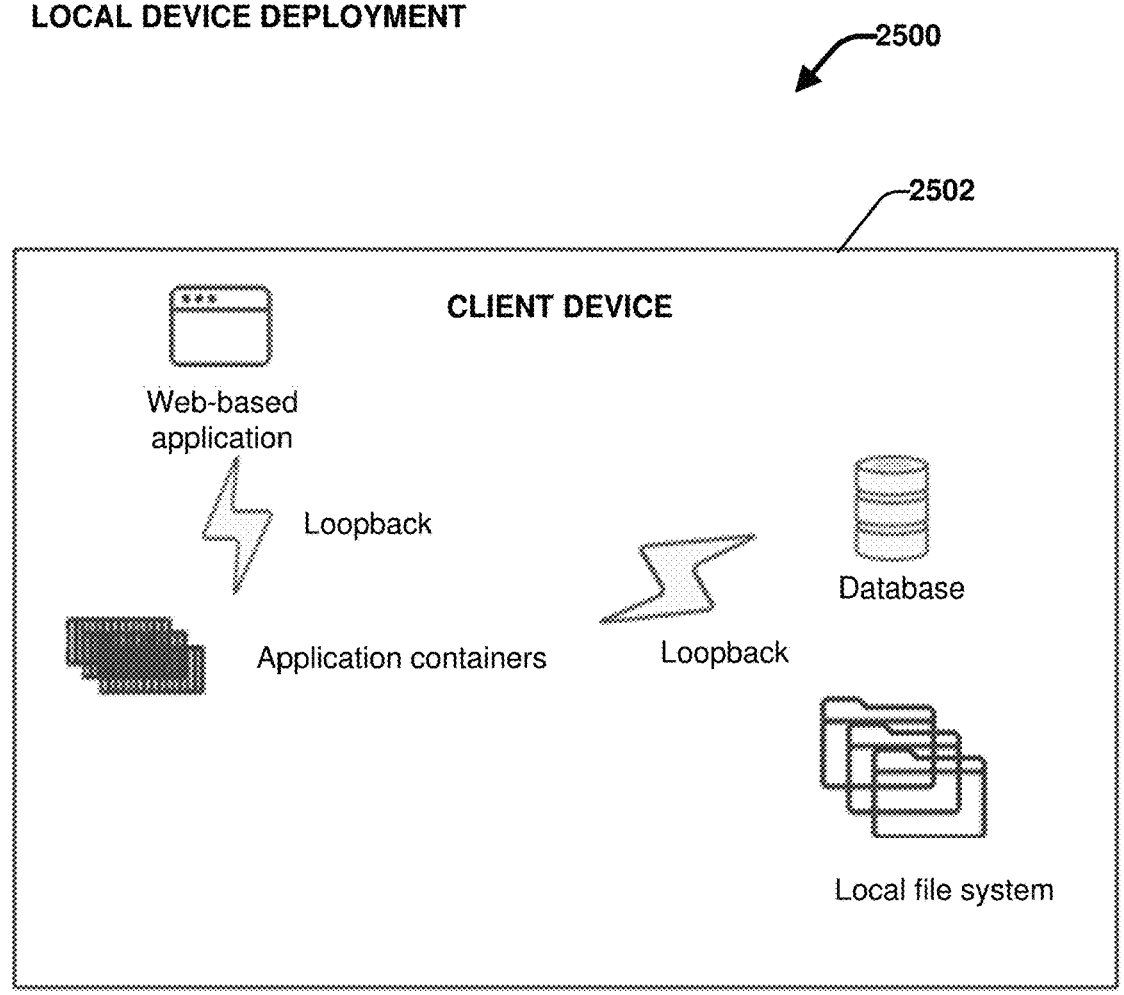
FIG. 25 illustrates a block diagram of another example, non-limiting operating environment in which one or more examples described herein can be facilitated.

FIG. 25 illustrates a schematic block diagram of another example computing environment 2500 in accordance with this disclosure in which the subject system (e.g., system 100), methods and computer readable media can be deployed. The computing environment 2500 includes a local device deployment in which all of the components of system 100 and/or platform orchestration server 600 are provided at a single client device 2502. With this implementation, the client device 2502 can include a web-based application which can be communicatively coupled via a loopback to one or more application containers. The one or more application containers can be communicatively coupled via a loopback to one or more databases and/or one or more local file systems.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "subsystem" "platform," "layer," "gateway," "interface," "service," "application," "device," and the like, can refer to and/or can include one or more computer-related entities or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various examples have been presented for purposes of illustration, but are not intended to be exhaustive or limited to the examples disclosed. Many modifications and variations can be apparent to those of ordinary skill in the art without departing from the scope and spirit of the described examples. The terminology used herein was chosen to best explain the principles of the examples, the practical application or technical improvement over technologies found in the marketplace, or to enable others of ordinary skill in the art to understand the examples disclosed herein.

What is claimed is:

1. A system, comprising:
   memory that stores computer executable instructions associated with a web platform that facilitates accessing, viewing and managing medical image data; and
   a processor that executes the computer executable instructions stored in the memory, wherein the computer executable instructions cause the processor to:
   scan endpoint databases as accessed via one or more networks to identify updates to local metadata associated with medical images as stored at the endpoint databases;
   update index metadata associated with the medical images in a global index to reflect the updates based on identification thereof by the processor, the global index comprising index information identifying the medical images, the index metadata, the endpoint databases where the medical images are respectively stored or a combination thereof, wherein the global index provides an anonymized representation of the medical images and enables flagging one or more of the medical images that include protected health information, and wherein the global index employs a unique identifier for each of the medical images in accordance with a defined naming ontology, wherein the processor performs an action comprising removing the one or more of the medical images flagged for including the protected health information from the global index;
   employ the global index to identify one or more of the medical images that satisfy one or more search criteria and generate search result data identifying the one or more medical images; and
   provide access to the global index and the search result data via the web platform.

2. The system of claim 1, wherein the computer executable instructions further cause the processor to:
   enable a plurality of users to view the medical images and the index metadata via the web platform; and
   enable the plurality of users to apply additional updates to the index metadata via the web platform, and wherein the processor further updates the global index to reflect the additional updates.

3. The system of claim 2, wherein the index metadata comprises metadata tags and wherein the additional updates comprise metadata tag updates based on user input editing the metadata tags and applying new metadata tags, and wherein the processor aggregates metadata tag updates for a same medical image or set of medical images in the global index as applied by different users over time.

4. The system of claim 1, wherein the computer executable instructions further cause the processor to further comprise:
   enable a plurality of users to view the medical images and the index metadata via the web platform; and
   enable the plurality of users to provide feedback information regarding an assessment of the medical images and the index metadata, and wherein the processor adds the feedback information to the global index.

5. The system of claim 4, wherein the computer executable instructions further cause the processor to:
   generate rating information for one or more of the medical images based on aggregated feedback received for the one or more medical images, and wherein the processor adds the rating information to the global index.

6. The system of claim 4, wherein the feedback information relates to a quality or a usefulness of the medical images or the index metadata.

7. The system of claim 1, wherein the computer executable instructions further cause the processor to:
   enable one or more users to create a project via the web platform with criteria of project medical image data related to the project, and wherein based on creation of the project, the processor employs the global index to identify and retrieve one or more of the medical images that satisfy the criteria.

8. The system of claim 1, wherein the computer executable instructions further cause the processor to:
   enable one or more users to perform data exchange actions via the web platform related to the one or more medical images identified in the search result data, the data exchange actions comprising transferring the one or more medical images from respective endpoint databases where they are stored to one or more selected systems or devices.

9. The system of claim 8, wherein the data exchange actions further comprise a purchase action for purchasing the one or more medical images based on the one or more medical images being associated with a usage agreement requiring purchase thereof.

10. A method, comprising:
scanning, by a system operatively coupled to a processor, endpoint databases as accessed via one or more networks to identify updates to local metadata associated with medical images as stored at the endpoint databases;
updating, by the system based on identification of the updates as a result of the scanning, index metadata associated with the medical images to reflect the updates, a global index comprising index information identifying medical images, the index metadata, and the endpoint databases where the medical images are respectively stored, wherein the global index provides an anonymized representation of the medical images and enables flagging one or more of the medical images that include protected health information, and wherein the global index employs a unique identifier for each of the medical images in accordance with a defined naming ontology, wherein the processor performs an action comprising removing the one or more of the medical images flagged for including the protected health information from the global index;
employing, by the system, the global index to identify one or more of the medical images that satisfy one or more search criteria; generating, by the system, search result data identifying the one or more medical images;
and providing, by the system, a plurality of users access to the global index and the search result data via a web platform.

11. The method of claim 10, further comprising: receiving, by the system, additional updates to the index metadata as provided by one or more users of the plurality of users via the web platform; and updating, by the system, the index metadata to reflect the additional updates.

12. The method of claim 11, wherein the index metadata comprises metadata tags and wherein the additional updates comprise metadata tag updates based on user input editing the metadata tags and applying new metadata tags, and wherein the updating comprises aggregating metadata tag updates for a same medical image or set of medical images in the global index as applied by different users over time.

13. The method of claim 10, further comprising: receiving, by the system via the web platform, feedback information regarding an assessment of a medical image included in the global index and associated index metadata for the medical image; and
adding, by the system, and the feedback information to the global index.

14. The method of claim 13, further comprising: generating, by the system, rating information for the medical image based on aggregated feedback received for the medical image; and adding, by the system, the rating information to the global index.

15. The method of claim 13, wherein the feedback information relates to a quality or a usefulness of the medical images or the metadata.

16. The method of claim 10, wherein the web platform comprises a project component that enables one or more users to create a project via the web platform with criteria of project medical image data related to the project, and wherein based on creation of the project, the method further comprises:
identifying, by the system, one or more target medical images of the medical images that satisfy the criteria using the global index; and
providing, by the system, the one or more users access to the one or more target medical images via the web platform.

17. The method of claim 10, wherein the web platform comprises an exchange management function that enables one or more users to control data exchange actions via the web platform related to the one or more medical images identified in the search result data, the data exchange actions comprising transferring, by the system, the one or more medical images from respective endpoint databases where they are stored to one or more selected systems or devices.

18. The method of claim 17, wherein the data exchange actions further comprise a purchase action that enables purchasing the one or more medical images based on the one or more medical images being associated with a usage agreement requiring purchase thereof.

19. A non-transitory machine-readable storage medium, comprising executable instructions associated with a web platform that facilitates accessing, viewing and managing medical image data, wherein when executed by a processor, the executable instructions cause the processor to:
scan endpoint databases as accessed via one or more networks to identify updates to local metadata associated with medical images as stored at the endpoint databases;
update as a result of the scanning, index metadata associated with the medical images to reflect the updates, a global index comprising index information identifying medical images, the index metadata, and the endpoint databases where the medical images are respectively stored; employ the global index to identify one or more of the medical images that satisfy one or more search criteria, wherein the global index provides an anonymized representation of the medical images and enables flagging one or more of the medical images that include protected health information, and wherein the global index employs a unique identifier for each of the medical images in accordance with a defined naming ontology, wherein the processor performs an action comprising removing the one or more of the medical images flagged for including the protected health information from the global index;
generate search result data identifying the one or more medical images; and
provide a plurality of users access to the global index and the search result data via the web platform.

20. The non-transitory machine-readable storage medium of claim 19, wherein the executable instructions further cause the processor to:
receive additional updates to the index metadata as provided by one or more users of the plurality of users via the web platform; and update the index metadata to reflect the additional updates.

* * * * *